(12) United States Patent
Mustaev et al.

(10) Patent No.: US 9,221,759 B2
(45) Date of Patent: Dec. 29, 2015

(54) FLUOROPHORE CHELATED LANTHANIDE LUMINESCENT PROBES WITH IMPROVED QUANTUM EFFICIENCY

(75) Inventors: Arkady Mustaev, New York, NY (US); Maxim Kozlov, New York, NY (US); Salvatore Marras, Roselle Park, NJ (US); Lev Krasnoperov, North Caldwell, NJ (US); Laura Wirpsza, Ocean City, NJ (US); Shyamala Pillai, Piscataway, NJ (US)

(73) Assignees: Rutgers, the State University of New Jersey, New Brunswick, NJ (US); New Jersey Institute of Technology, Newark, NJ (US)

( * ) Notice: Subject to any disclaimer, the term of this patent is extended or adjusted under 35 U.S.C. 154(b) by 178 days.

(21) Appl. No.: 13/522,043

(22) PCT Filed: Jan. 13, 2011

(86) PCT No.: PCT/US2011/021105
§ 371 (c)(1),
(2), (4) Date: Nov. 1, 2012

(87) PCT Pub. No.: WO2011/088193
PCT Pub. Date: Jul. 21, 2011

(65) Prior Publication Data
US 2013/0202536 A1  Aug. 8, 2013

Related U.S. Application Data

(60) Provisional application No. 61/294,735, filed on Jan. 13, 2010, provisional application No. 61/360,288, filed on Jun. 30, 2010.

(51) Int. Cl.
| | | |
|---|---|---|
| *C07D 215/227* | (2006.01) | |
| *C07D 215/38* | (2006.01) | |
| *A61K 49/00* | (2006.01) | |
| *C12Q 1/68* | (2006.01) | |
| *C07D 215/233* | (2006.01) | |
| *C07D 257/02* | (2006.01) | |
| *C07H 21/00* | (2006.01) | |
| *C07K 14/00* | (2006.01) | |

(52) U.S. Cl.
CPC ........ *C07D 215/227* (2013.01); *C07D 215/233* (2013.01); *C07D 215/38* (2013.01); *C07D 257/02* (2013.01); *C07H 21/00* (2013.01); *C07K 14/00* (2013.01); *C12Q 1/6816* (2013.01)

(58) Field of Classification Search
CPC . A61K 31/02; A61K 31/105; A61K 31/4704; C07D 215/233; C07D 215/157; C07D 215/33
USPC ............ 424/9.6, 130.1; 546/5, 82, 83, 86, 90, 546/157
See application file for complete search history.

(56) References Cited

U.S. PATENT DOCUMENTS

| | | | |
|---|---|---|---|
| 4,522,811 | A | 6/1985 | Eppstein et al. |
| 5,112,954 | A * | 5/1992 | Abrams et al. ............. 530/391.9 |
| 5,145,772 | A | 9/1992 | Voyta et al. |
| 5,179,096 | A | 1/1993 | Gentilini et al. |
| 5,220,000 | A | 6/1993 | Theodoropulos |
| 5,430,138 | A | 7/1995 | Urdea et al. |
| 5,437,977 | A | 8/1995 | Segev |
| 5,530,101 | A | 6/1996 | Queen et al. |
| 5,585,089 | A | 12/1996 | Queen et al. |
| 5,597,909 | A | 1/1997 | Urdea et al. |
| 5,622,821 | A | 4/1997 | Selvin et al. |
| 5,639,615 | A | 6/1997 | Selvin et al. |
| 5,693,761 | A | 12/1997 | Queen et al. |
| 5,693,762 | A | 12/1997 | Queen et al. |
| 5,798,230 | A | 8/1998 | Bornkamm et al. |
| 5,925,517 | A | 7/1999 | Tyagi et al. |
| 6,037,130 | A | 3/2000 | Tyagi et al. |
| 6,150,097 | A | 11/2000 | Tyagi et al. |
| 6,407,213 | B1 | 6/2002 | Carter et al. |
| 6,461,817 | B1 | 10/2002 | Alland et al. |
| 6,631,283 | B2 | 10/2003 | Storrie et al. |
| 6,740,756 | B1 | 5/2004 | Chan et al. |
| 2002/0058793 | A1 | 5/2002 | Uray et al. |
| 2003/0232333 | A1 | 12/2003 | Ladner et al. |

(Continued)

FOREIGN PATENT DOCUMENTS

| | | |
|---|---|---|
| EP | 239400 | 8/1994 |
| JP | 52-83382 | 7/1977 |

(Continued)

OTHER PUBLICATIONS

Yang Chen et al. Sensitization Luminescent Terbium Nanoparticles: Preparation and Time-Resoloved Fluorescence Assay for DNA, Anal. Chem. 2007, 79, 960-965.*
Paul R. Selvin et al., Synthesis of 7-amino-4-trifluoromethyl-2-(1H)-quinolinone and its use as an antenna molecule for luminescent europium polyaminocarboxylates chelates, Journal of Photochemistry and Photobiology A: Chemistry 135, 27-32, 2000.*
Bird et al., "Single-chain antigen-binding proteins," Science, (1988) vol. 242, pp. 423-426 (Abstract only).
Boerner et al., "Production of antigen-specific human monoclonal antibodies from in vitro-primed human splenocytes," J. Immunol., (1991) vol. 147 pp. 86-95 (abstract only).
Boshell et al., "Indirect immunofluorescence as a supplementary test for confirming HIV-1 infection: the experience of the National Institute of Health, 1993-2000," Biomedica, (2002) vol. 22, pp. 30-38 (Abstract only).

(Continued)

*Primary Examiner* — Michael G Hartley
*Assistant Examiner* — Jagadishwar Samala
(74) *Attorney, Agent, or Firm* — Fox Rothschild LLP; Gerard P. Norton; Robert N. Henrie, II

(57) ABSTRACT

The invention relates to novel luminescent compositions of matter containing a fluorophore, synthetic methods for making the compositions, macromolecular conjugates of the compositions, and the use of the compositions in various methods of detection. The invention also provides kits containing the compositions and their conjugates for use in the methods of detection.

23 Claims, 12 Drawing Sheets

(56) References Cited

U.S. PATENT DOCUMENTS

| | | | |
|---|---|---|---|
| 2005/0026813 A1 | 2/2005 | Olstein et al. | |
| 2005/0085413 A1 | 4/2005 | Jin et al. | |
| 2010/0178251 A1* | 7/2010 | Mustaev | 424/9.6 |

FOREIGN PATENT DOCUMENTS

| | | |
|---|---|---|
| WO | 90/07861 | 7/1990 |
| WO | 9303772 A1 | 3/1993 |
| WO | 2008/019403 | 2/2008 |

OTHER PUBLICATIONS

Chen et al., "Synthesis of 7-amino-4-trifluoromethyi-2-(1H)-quinolinone and its use as an antenna molecule for luminscent europium polyaminocarboxylates chelates," J Photochemistry and Photobiology A: Chemistry, (2000) vol. 135, pp. 27-32.

Gac-Breton et al., "Norfloxacin-Poly(L-Lysine Citramide Imide) Conjugates and Structure-dependence of the Drug Release," J. Drug Targeting, (2004) vol. 12 (5); pp. 297-307.

Ge et al., "New 9- or 10-dentate luminscent lanthanide chelates," Bioconjugate Chem, (2008) vol. 19, pp. 1105-1111.

Green et al., "Development of ERK Activity Sensor, an in vitro, FRET-based sensor of Extracellular Regulated Kinase activity," BMC Chem. Biol., (2005) vol. 5, p. 1.

Gudgin-Dickson et al., "Ultrasensitive bioanalytical assays using time-resolved fluorescence detection," Pharmac. Ther., (1995) vol. 66, pp. 207-235.

Hemmila et al., "Progress in lanthanides as luminescent probes," J. Fluoresc., (2005) vol. 15, pp. 529-542 (Abstract only).

Hoogenboom et al., "Antibody phage display technology and its applications," Immunotechnology, (1998) vol. 4, pp. 1-20 (Abstract only).

Hoogenboom et al., "Natural and designer binding sites made by phage display technology," Immunol Today, (2000) vol. 2, pp. 371-378 (Abstract only).

Huang et al., "Construction of representative immunoglobulin variable region cDNA libraries from human peripheral blood lymphocytes without in vitro stimulation," J. Immunol. Methods (1991), vol. 141, pp. 227-236 (Abstract only).

Huston et al., "Protein engineering of antibody binding sites: recovery of specific activity in an anti-digoxin single-chain Fv analogue produced in *Escherichia coli*," Proc. Natl. Acad. Sci. USA, (1988) vol. 85, pp. 5879-5883.

Krasnoperov et al., "Luminscent probes for ultrasensitive detection of nucleic acid," Bioconjugate Chem, (Jan. 19, 2010) vol. 21, pp. 319-327.

Nogrady, T., "Medicinal Chemistry A Biochemical Approach," Oxford University Press, New York, pp. 388-392 (Book description only).

Ozaki et al., "Sensitization of Europium(III) Luminescence by DTPA Derivatives," Chem. Lett., (2000) pp. 312-313.

Persson et al., "Generation of diverse high-affinity human monoclonal antibodies by repertoire cloning," Proc. Nat. Acad. Sci. USA, (1991) vol. 88, pp. 2432-2436.

Qu et al., "Carbohydrates engineered at antibody constant domains can be used for site-specific conjugation of drugs and chelates," J. Immunol. Meth., (1998) vol. 213, pp. 131-144 (Abstract only).

Riechmann et al., "Reshaping human antibodies for therapy," Nature, (1988) vol. 332, pp. 323-327.

Rieutord et al., "Fiuoroquinolones as sensitizers of lanthanide fluorescence: application to the liquid chromatographic determination of ciprofloxacin using terbium," Analytica Chimica Acta, Elsevier, Amsterdam, NL (May 20, 1994) vol. 290, pp. 215-225.

Sambrook, J. et al., "Molecular Cloning: A Laboratory Manual," Cold Spring Harbor Laboratory Press, (1989) Cold Spring Harbor, N.Y. (Desription only).

Selvin et al., "Principles and biophysical applications of lanthanide-based probes," Ann. Rev. Biophys. Biomol. Structure, (2002) vol. 31, pp. 275-302 (Abstract only).

Selvin, "Crystal Structure and Spectroscopic Characterization of Luminescent Europium Chelate", Inorg. Chem. (1996), vol. 35, pp. 700-705.

Tak et al., "Synthesis, characterization, electrochemistry and kinetics of CTDNA binding of a bis ciprofloxacin borate copper (II) complex," Transition Metal Chemistry (Oct. 1, 2002); vol. 27(7) pp. 741-747.

Tardif et al., "Presence of Host ICAM-1 in Human Immunodeficiency Virus Type 1 Virions Increases Productive Infection of CD4+ T Lymphocytes by Favoring Cytosolic Delivery of Viral Material," J. Virol., (2003) vol. 77, pp. 12299-12309.

Tempest et al., "Reshaping a human monoclonal antibody to inhibit respiratory syncytial virus infectin in vivo," Biotechnology, (1991) vol. 9, pp. 266-271 (Abstract only).

Tyagi et al., "Molecular beacons: hybridization probes for detection of nucleic acids in homogeneous solutions," Nonradioactive Analysis of Biomolecules, second edition (Kessler, C., Ed.), (2000) pp. 606-616, Springer Verlag, Berlin, Germany (Abstract only).

Vaughan et al., "Human Antibodies with Sub-nanomolar Affinities Isolated from a Large Non-immunized Phage Display Library," Nature Biotechnology, (1996) vol. 14, pp. 309-314 (Abstract only).

Verhoeyen et al., "Reshaping human antibodies: grafting an antilysozyme activity," Science, (1988) vol. 239, pp. 1534-1536 (Abstract only).

Von Ahsen, et al., "Assay concordance between SPA and TR-FRET in high-throughput screening," J Biomol. Screen, (2006) vol. 11, pp. 606-616.

Ward et al., "Binding activities of a repertoire of single immunoglobulin variable domains secreted from *Escherichia coli*," Nature, (1989) vol. 341, pp. 544-546 (Abstract only).

Xiao et al., "Rationally designed, polymeric, extended metal-ciprofloxacin complexes," Chemistry—A European Journal (Nov. 4, 2005); vol. 11 (22), pp. 6673-6686.

Zhang et al., "Time-resolved Forster resonance energy transfer assays for the binding of nucleotide and protein substrates to p38alpha protein kinase," Anal Biochem., (2005) vol. 343, pp. 76-83.

\* cited by examiner

A

B

A

B

FLUOROPHORE CHELATED LANTHANIDE LUMINESCENT PROBES WITH IMPROVED QUANTUM EFFICIENCY

CROSS-REFERENCE TO RELATED APPLICATIONS

This application is the U.S. National Phase of International Patent Application Ser. No. PCT/US11/21105, filed on Jan. 13, 2011, which claims priority under 35 U.S.C. §119(e) to U.S. Provisional Application Ser. Nos. 61/294,735, filed on Jan. 13, 2010, and 61/360,288, filed on Jun. 30, 2010, all of which are hereby incorporated by reference in their entireties for all purposes. This application is also related to U.S. patent application Ser. No. 12/377,199, which was filed on Feb. 11, 2009, which is the U.S. National Phase Application of International Application Ser. No. PCT/US07/75761, which was filed Aug. 11, 2007, which claims priority under 35 U.S.C. §119(e) to U.S. Provisional Application Ser. Nos. 60/822,219, which was filed on Aug. 11, 2006, and 60/822,235, which was filed on Aug. 12, 2006, the disclosures of which are incorporated herein by reference.

FIELD OF THE INVENTION

The present invention relates to new luminescent probes that can be used for ultrasensitive detection of biopolymers as well as for invasive and non-invasive determination of the composition of multicomponent mixtures employing highly luminescent lanthanide and ruthenium ion based tracers, a method for non-invasive determination of the composition of multicomponent mixtures, not limited to optically transparent materials, employing sensitive luminescent lanthanide and ruthenium ion based tracers, new materials useful in the method, and new methods to prepare the compounds.

BACKGROUND OF THE INVENTION

Luminescent lanthanide chelates have become a primary focus of investigation due to their highly unusual spectral properties (Gudgin-Dickson et al. (1995) Pharmac. Ther. 66:207-235; Selvin, P. R. (2002) Annu. Rev. Biophys. Biomol. Strutt. 31:275-302; and Hemmila et al. (2005) J. Fluoresc. 15:529-542). These molecules have been used in wide variety of biochemical assays, including, for example, medical diagnostics, drug discovery, and as imaging tools in cell biological applications. Luminescent lanthanide chelates are especially useful as non-isotopic alternatives to conventional organic fluorophores in the applications where high background fluorescence is an issue. The unusual spectral (i.e., sharply spiked peaks) and temporal (i.e., long lasting emissions) properties of the luminescent lanthanide chelates can allow for (i) ultra-high sensitivity of detection (ii) facile, simultaneous monitoring of several analytes in the same sample mixture, and (iii) more information to be obtained from a given individual analyte in a sample.

A lanthanide probe can contain, for example, an organic fluorophore and a caged, or chelated lanthanide. The fluorophore moiety acts as an antenna, or sensitizer, which absorbs the energy of the excitation light and transfers it to the lanthanide in a radiation-less fashion. The antenna is required to "pump," or activate the metal, since the absorbance of the lanthanide moiety is very low. The antenna-to-lanthanide energy transfer occurs only over a short distance (on the order of a few angstroms), which generally requires that the two moieties be tethered together.

Temporal and spectral gating enables unusually sensitive detection of lanthanide emission even in samples containing significant short-lived auto-fluorescence (e.g., biological specimens or tissues). These compounds are therefore potentially useful in a wide variety of technical and biological tasks, such as tracing analysis, immunoanalysis, tissue-specific imaging, and detection of single molecules in living cells.

Development of new luminescent probes is challenging, since the transfer of energy from the antenna to the lanthanide is complex (a process not yet well understood) and very sensitive to subtle structural variations in the fluorophore. Another challenge is the necessity of combining three functional units within the same reporting probe: an antenna, a chelated lanthanide, and a cross-linking group (for attachment to the biomolecule of interest). This requires a complex synthetic strategy, eventually leading to compounds whose size often exceeds 1,000 Da.

Two commonly used classes of lanthanide chelates are diethylenetriaminepentaacetic acid (DTPA) and tetraethylenetetraminohexaacetic acid (TTHA). These chelates attach to 7-amino quinolones, which are known as DTPA and/or TTHA-cs124 derivatives. The advantage of these classes of compounds is their high quantum yield, high solubility in water, and the possibility of introducing chemical modifications in the fluorophore to spectrally optimize the transfer of energy to the lanthanide, and to enable the attachment of a cross-linking group. A number of methods for the conjugation of these chelates to biomolecules have been suggested. One of them is to use the dianhydride form of DTPA, in which one of the anhydrides modifies the amino group of the chromophore, while the other anhydride reacts with amino group of the biomolecule. Even though this approach is technically simple, it raises concerns about the side reactions (modification of other nucleophilic groups) due to the high reactivity of anhydrides. The second approach takes advantage of the conjugation of one of the DTPA anhydride groups with the cs124 moiety, followed by reaction of the remaining anhydride with the diamine. The unmodified amino group of the resulted adduct can then be converted to an amino-reactive isothiocyano or thiol-reactive groups. This mode of attachment of the cross-linking group weakens the retention of the lanthanide within the chelate by eliminating one ligating carboxylate, and it also reduces the brightness of the lanthanide (30 to 1,000%) due to the quenching effect of the additional coordinated water molecule. These factors restrict in vivo applications where high concentration of metal scavengers is an issue (e.g., intracellular imaging). Analogous derivatives of the fluorophore coumarine have been suggested and used in biophysical studies. However, compared to their quinolone counterparts, they are less bright and do not support terbium (Tb) luminescence.

The unique photon emission properties of lanthanide-based probes render them suitable for a wide variety of applications that require ultrasensitive detection of biomolecules. Progress in this field depends on the availability of efficient probes. The complexity of energy pathways in luminescent lanthanide chelates is not fully understood, leaving much room for improvement in their applications as labels for probes. The development of more efficient probes is highly desirable, because new more challenging applications have arisen (e.g., for the detection of rare pathogens in environmental samples and detection of single molecules in cells).

SUMMARY OF THE INVENTION

Provided herein is a composition of matter, which includes: (i) a fluorophore of Formula (I) or Formula (II); and (ii) a chelating moiety covalently joined, optionally through a first linker, to the fluorophore, wherein Formula (I) is:

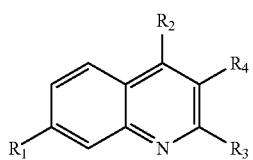

and wherein:
R₁ is the site of a covalent attachment, optionally through a linker, of the sensitizer moiety to the chelating moiety;
$R_2$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene, or alkoxylene moieties are optionally further substituted with from 1-4 halogen atoms;
$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene, or alkoxylene moieties are optionally further substituted with from 1-4 halogen atoms;
$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, alkylarene, or alkoxylene moieties are optionally further substituted with from 1-4 halogen atoms;
wherein $R_2$, $R_3$, or $R_4$ optionally further contain a crosslinking group selected from the group consisting of isothiocyanate, haloacetate, haloacetamide, nitrogen mustard, epoxide, maleimide, disulfide, activated ester, imidate, azide, acetylenic derivatives, aldehydes, sulfonyl chlorides, acylazides, and acylhydrazides;

and wherein Formula (II) is:

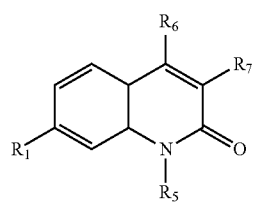

and wherein:
R₁ is the site of a covalent attachment, optionally through a linker, of the sensitizer moiety to the chelating moiety;
$R_5$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;
$R_6$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;
$R_7$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;
wherein $R_5$, $R_6$, or $R_7$ optionally further contain a crosslinking group selected from the group consisting of isothiocyanate, haloacetate, haloacetamide, nitrogen mustard, epoxide, maleimide, disulfide, activated ester, imidate, azide, acetylenic derivatives, aldehydes, sulfonyl chlorides, acylazides, and acylhydrazides.

In some embodiments, the composition of matter can contain a chelating moiety including EDTA, DTPA, TTHA, DOTA, TAGA, DOTP, DTPA-BMA, DO2P, and HP-DO3A.

In embodiments where the composition of matter is a luminescent composition or luminescent chelate, the composition can further contain a metal ion chelated to the chelating moiety. The chelated metal ion can be a lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV).

In other embodiments, the compositions of matter can be conjugated to a macromolecule. The macromolecule can be a polypeptide (e.g., an antigen or antigen-binding fragment there, or a polypeptide ligand for a cellular receptor), or a nucleic acid (e.g., DNA or RNA).

Also provided herein are pharmaceutical compositions containing any of the compositions of matter described herein and a pharmaceutically acceptable carrier.

Featured herein is an in vitro method of detecting a target with a probe. The method includes the steps of: (a) contacting a sample with a luminescent probe compositions, which includes a targeting-probe moiety having an affinity for a target, the targeting-probe moiety covalently conjugated to a luminescent chelate composition comprising: (i) a fluorophore of Formula (I) or Formula (II); and (ii) a chelating moiety covalently joined, optionally through a first linker, to the fluorophore; and (b) detecting a signal produced from the luminescent probe composition.

Also featured herein is an in vivo method of detecting a target with a probe. The method includes the steps of: delivering to a subject a luminescent probe composition comprising a target-probe moiety having an affinity for a target, the targeting-probe moiety covalently conjugated to a luminescent chelate composition comprising: (i) the fluorophore of Formula (I) or Formula (II); and (ii) a chelating moiety covalently joined, optionally through a first linker, to the fluorophore; and detecting a signal produced from the luminescent probe composition.

Provided herein is a luminescently labeled hairpin-forming oligonucleotide consisting of (a) the luminescent chelate composition comprising: (i) a fluorophore of Formula (I) or Formula (II); and (ii) a chelating moiety covalently joined, optionally through a first linker, to the fluorophore;
wherein the $R_1$ chelating moiety is selected from the group consisting of EDTA, DTPA, TTHA, DOTA, TAGA, DOTP, DTPA-BMA, DO2P, and HP-DO3A; and
wherein the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV);
the luminescent composition covalently conjugated to a hairpin-forming oligonucleotide; and
(b) a quencher moiety capable of quenching the fluorescence of the fluorophore or the luminescence of the lanthanide moiety, wherein the quencher moiety is covalently conjugated to the hairpin-forming oligonucleotide;
the oligonucleotide having a closed conformation including a single-stranded loop and a stem duplex formed by complementary 3' and 5' arms, wherein the quencher moiety is in a quenching relationship to at least one of the lanthanide moiety or the fluorophore; wherein, when excited at the maximum excitation wavelength of the fluorophore, emission at the maximum emission wavelength of the fluorophore is substantially suppressed relative to the unquenched magnitude and emission at the maximum emission wavelength of the fluorophore; and
the oligonucleotide having an open conformation, not including the stem duplex, in which the quencher moiety is not in a quenching relationship with the lanthanide or the fluorophore; wherein, when excited at the maximum excitation wavelength of one or both of the first and second sensitizer moieties, the luminescence of the lanthanide moiety increases due to fluorescence resonance energy transfer from the fluorophore.

Also featured herein is a reagent kit for nucleic acid amplification for nucleic acid amplification including ingredients for a nucleic acid amplification, a detector probe that is an oligonucleotide according to any of the conjugated oligonucleotides described herein, and instructions for carrying out the amplification reaction.

The invention also features a reagent kit for an amplification reaction including ingredients for an amplification reaction that includes at least one primer (e.g., any of the luminescently labeled hairpin-forming oligonucleotide conjugates described herein), ingredients for the amplification assay and instructions for carrying out the amplification assay. Nucleic acid amplification can be polymerase chain reaction (PCR), strand displacement amplification (SDA), transcription-mediated amplification (TMA), ligase chain reaction (LCR), nucleic acid sequence based amplification (NASBA), rolling circle amplification, loop-mediated isothermal amplification (LAMP), or amplification of RNA by an RNA-directed RNA polymerase.

Also featured herein is a detection assay which includes the steps of adding to a sample that can optionally contain a target strand at least one detector probe that is any luminescently labeled hairpin-forming oligonucleotide conjugate described herein and detecting luminescence emission from the at least one detector probe's luminescent chelate moiety. Nucleic acid amplification can be polymerase chain reaction (PCR), strand displacement amplification (SDA), transcription-mediated amplification (TMA), ligase chain reaction (LCR), nucleic acid sequence based amplification (NASBA), rolling circle amplification, loop-mediated isothermal amplification (LAMP), or amplification of RNA by an RNA-directed RNA polymerase.

Also provided is an amplification assay that includes the steps of adding to a sample that can optionally contain a target strand the reagents to perform any amplification reaction described herein at least one of any of the luminescently labeled hairpin-forming oligonucleotide conjugates described herein, and detecting luminescence and/or fluorescence emission from the luminescent chelate moiety of the at least one of any of the luminescently labeled hairpin-forming oligonucleotide conjugates described herein.

Also provided herein is a method for detecting an analyte in a sample including the steps of contacting a sample containing the analyte with a luminescent chelate composition to specifically bind the anlayte to form a luminescent-analyte complex, illuminating the sample with excitation radiation, and detecting emission radiation of at least one luminescent-analyte complex, wherein the luminescent chelate composition includes any fluorophore and chelating moiety described herein.

The details of one or more embodiments of the invention are set forth in the accompanying drawings and the description below. Other features, objects, and advantages of the invention will be apparent from the description and drawings, and from the claims. All cited patents, patent applications, and references are incorporated by reference in their entireties for all purposes.

In case of conflict, the present specification, including definitions, will control. In addition, the materials, methods, and examples are illustrative only and not intended to be limiting.

DETAILED DESCRIPTION OF THE INVENTION

Figure 1:
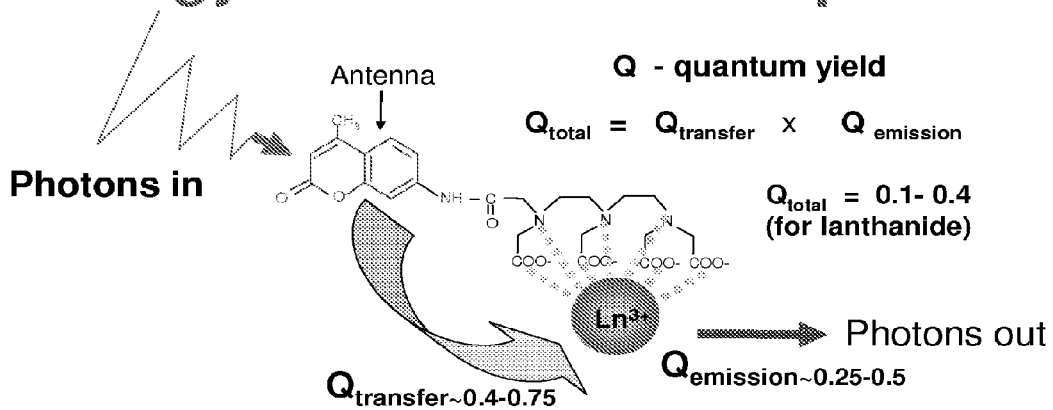
FIG. 1 is a schematic description of energy flow in a lanthanide probe.

Featured herein are compositions of matter and macromolecular conjugates of the compositions, as well as methods of synthesis and use for the compositions and their conjugates. Various aspects of the invention are described below.

Definitions

The term "subject" refers to a member of the class Mammalia. Examples of mammals include, without limitation, humans, primates (e.g., chimpanzees, monkeys, baboons), rodents (e.g., mice, rats, rabbits, guinea pigs, horses, livestock, dogs, cats, sheep, and cows). In certain preferred embodiments, the "subject" is a human (e.g., a human patient).

As used herein, "macromolecule" refers to a molecule with a large molecular mass, composed of much larger numbers (hundreds or thousands) of atoms than ordinary molecules. Some macromolecules are individual entities that cannot be subdivided without losing their identity (e.g., certain proteins, certain nucleic acids). Others (e.g., polymers) are multiples of a repeating building block (monomer) in chains or networks (e.g., plastics, cellulose). Examples of such macromolecules include, but are not limited to, polypeptides (protein complexes), nucleic acids (e.g., DNA and RNA), polymers (e.g., polystyrene, polyethylene, cellulose (i.e., sugar polymers)). The term macromolecule also refers to complexes of two or more polypeptides or nucleic acids (e.g., a protein dimer, or a double-stranded DNA molecule).

As used herein, the term "probe" refers to a molecule that constitutes one member of a binding pair, wherein the other member of the binding pair is the "target" of the probe. The molecule can be a small molecule (e.g., a compound), a macromolecule (e.g., an antibody, a nucleic acid; see above). For example, where the probe is an antibody, the target is the antigen (e.g., the antigen containing the epitope) that the antibody specifically recognizes. Where the probe is a ligand, the target is the cognate receptor the ligand specifically binds to (e.g., Epidermal Growth Factor (EGF) ligand binding to EGF-Receptor). Where the probe is a nucleic acid (e.g., a DNA probe), the target is a complementary nucleic acid sequence to the nucleic acid probe. Where the probe is a polypeptide, the polypeptide can be of any length or function. Where the probe is a compound, the target can be, e.g., a receptor (e.g., a steroid or hormone receptor (e.g., the estrogen receptor) or a enzyme target (e.g., a kinase) where the compound binds to or inhibits the enzyme target. The polypeptide can also be a polypeptide that is encoded or expressed in any species or biological organism (e.g., a bacterial protein, a viral protein, an insect protein, a nematode protein, a mammalian protein, a human protein). The polypeptide can also be naturally produced by an organism or can be made synthetically (e.g., by automated chemical synthesis).

As used herein, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, pharmaceutically acceptable derivatives of a composition for use in any of the in vivo methods described herein include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" carbon chains, if not specified, contain from 1 to 20 (e.g., 1, 2, 3, 4, 5, 6, 7, 8, 9, 10, 11, 12, 13, 14, 15, 16, 17, 18, 19, or 20; 1-5, 1-6, 1-10, 10-15, 15-20) carbons and are straight, cyclic, or branched. Alkenyl carbon chains of from 2 to 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbons, in certain embodiments, contain 1 to 8 (e.g., 1, 2, 3, 4, 5, 6, 7, or 8) double bonds and alkenyl carbon chains of 2 to 16 (e.g., 2, 3, 4, 5, 6, 7, 8, 9, 10, 11, 12, 13, 14, 15, or 16) carbons, in certain embodiments, contain 1 to 5 (e.g., 1, 2, 3, 4, or 5) double bonds. Alkynyl carbon chains of from 2 to 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbons, in certain embodiments, contain 1 to 8 triple bonds, and the alkynyl carbon chains of 2 to 16 (e.g., 2, 3, 4, 5, 6, 7, 8, 9, 10, 11, 12, 13, 14, 15, or 16) carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons (e.g., 1, 2, 3, 4, 5, or 6). As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 (e.g., 3, 4, 5, 6, 7, 8, 9, or 10; 3-5, 3-6, 3-8, 5-10) carbon atoms, in other embodiments of 3 to 6 (e.g., 3, 4, 5, or 6) carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 (e.g., 3, 4, 5, 6, 7, 8, 9 or 10; 3-5, 3-7, 5-10) carbon atoms, with cycloalkenyl groups, in further embodiments, containing 4 to 7 (e.g., 4, 5, 6, or 7) carbon atoms and cycloalkynyl groups, in further embodiments, containing 8 to 10 (e.g., 8, 9 or 10) carbon atoms. The ring systems of the cycloalkyl, cycloalkenyl and cycloalkynyl groups may be composed of one ring or two or more rings which may be joined together in a fused, bridged or Spiro-connected fashion. "Cycloalk(en)(yn)yl" refers to a cycloalkyl group containing at least one double bond and at least one triple bond.

As used herein, "aryl" or "arene" refers to aromatic monocyclic or multicyclic groups containing from 6 to 19 (e.g., 6, 7, 8, 9, 10, 11, 12, 13, 14, 15, 16, 17, 18, or 19; 6-8, 6-10, 6-12, 6-15, 10-15, 15-19) carbon atoms. Aryl groups include, but are not limited to groups such as unsubstituted or substituted fluorenyl, unsubstituted or substituted phenyl, and unsubstituted or substituted naphthyl.

As used herein, "alkyoxylene" refers to a "alkyl," "alkenyl" and "alkynyl" carbon chains as described above bonded through another substituent through an oxygen atom.

As used herein, "heteroaryl" refers to a monocyclic or multicyclic aromatic ring system, in certain embodiments, of about 5 to about 15 (e.g., 5, 6, 7, 8, 9, 10, 11, 12, 13, 14, or 15; 5-7, 5-9, 5-10, 10-12, 10-15) members where one or more, in one embodiment 1 to 3 (e.g., 1, 2, or 3), of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl. As used herein, "heterocyclyl" refers to a monocyclic or multicyclic non-aromatic ring system, in one embodiment of 3 to 10 (e.g., 3, 4, 5, 6, 7, 8, 9, or 10) members, in another embodiment of 4 to 7 (e.g., 4, 5, 6, or 7) members, in a further embodiment of 5 to 6 members, where one or more, in certain embodiments, 1 to 3 (e.g., 1, 2, or 3), of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above. As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide. As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "alkenylene" refers to a straight, branched or cyclic, in one embodiment straight or branched, divalent aliphatic hydrocarbon group, in certain embodiments having from 2 to about 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbon atoms and at least one double bond, in other embodiments 1 to 12 (e.g., 1, 2, 3, 4, 5, 6, 7, 8, 9, 10, 11, or 12; 1-5, 2-6, 2-10, or 10-12) carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 (e.g., 2, 3, 4, 5, or 6) carbons. In certain embodiments, alkenylene groups are lower alkenylene, including alkenylene of 3 to 4 carbon atoms. As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH2-. The term "lower alkynylene" refers to alkynylene groups having 2 to 6 (e.g., 2, 3, 4, 5, or 6) carbons. In certain embodiments, alkynylene groups are lower alkynylene, including alkynylene of 3 to 4 carbon atoms. As used herein, "alk(en)(yn)ylene" refers to a straight, branched or cyclic, in certain embodiments straight or branched, divalent aliphatic hydrocarbon group, in one embodiment having from 2 to about 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbon atoms and at least one triple bond, and at least one double bond; in another embodiment 1 to 12 (e.g., 1, 2, 3, 4, 5, 6, 7, 8, 9, 10, 11, or 12; 1-5, 2-6, 2-10, or 10-12) carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C=C—(CH2)n-C≡C—, where n is 1 or 2. The term "lower alk(en)(yn)ylene" refers to alk(en)(yn)ylene groups having up to 6 (e.g., 1, 2, 3, 4, 5, or 6) carbons. In certain embodiments, alk(en)(yn)ylene groups have about 4 (e.g., 1, 2, 3, or 4) carbon atoms.

As used herein, "cycloalkylene" refers to a divalent saturated mono- or multicyclic ring system, in certain embodiments of 3 to 10 (e.g., 3, 4, 5, 6, 7, 8, 9, or 10; 3-5, 3-6, 3-10, or 6-10) carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 (e.g., 5, 6, 7, 8, 9, 10, 11, 12, 13, 14, or 15; 5-8, 5-10, 8-12, or 10-15) atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring. As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from Q1.

As used herein, isothiocyanate (ITC) refers to a —N=C=S moiety.

Where the number of any given substituent is not specified (e.g., haloalkyl), there may be one or more substituents present. For example, "haloalkyl" may include one or more of the same or different halogens. As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11: 942-944).

As used herein, "aptamer" refers to oligonucleic acid or peptide molecules that bind to a specific target molecule. "Nucleic acid aptamers" are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. "Peptide aptamers" are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range).

The Compositions of Matter

The present invention provides new approaches for the introduction of cross-linking groups into DTPA and/or TTHA cs124 chelates by modification of the chromophore moiety. It has been found that the synthesized luminescent probes of the invention are more resistant to EDTA challenge than previously described DTPA-cs124-based probes, and that these new probes are highly luminescent. Some of these compounds were validated as luminescent labels by including them in molecular beacon probes, which are widely used for DNA and RNA detection. The resulting detection sensitivity of these molecular beacons is between 0.5 to 1 pM, which is the best ever reported for non-amplified DNA detection systems. In certain embodiments, these compounds are used to efficiently label streptavidin, a protein commonly used in detection assays (see Example 10 below). Additional results demonstrate the high performance of new probes in biochemical detection tests.

In another aspect the present invention provides novel probes having novel organic fluorophores (antennas). In addition, the probes of the invention may have novel chelating groups, such as, for example EDTA, DTPA, TTHA, DOTA, TAGA, DOTP, DTPA-MBA, DO2P, and HP-DO3A.

The compositions and conjugates of the compositions provided herein are useful in any of the methods provided herein. In one embodiment, the compositions or conjugates thereof may be used in detection assay in vitro. In a related embodiment, the compositions and conjugates thereof may be used for diagnostic or detection methods in vivo.

In one embodiment, the compositions for use in the conjugates and methods provided herein include a compound of Formula (A):

Y-A-L  (A)

wherein
Y is a chelating group;
A is an organic fluorophore; and
L is an organic group capable of coupling to biopolymers.

In certain embodiments, Y is a chelating group comprising EDTA, DTPA, TTHA, DOTA, TAGA, DOTP, DTPA-MBA, DO2P, or HP-DO3A.

In certain embodiments, A is an unsubstituted or substituted organic fluorophore comprising 7-amino-2(1H)-quinolone or 7-aminoquinoline.

In certain embodiments L is a linking group comprising —$CH_2C(=O)NH(CH_2)_6$—X, where X is an isothiocyanate, isocyanate, haloacetate, epoxide, maleimde, disulfide, activated ester, imidate, azide or acetylenic derivative.

The Y chelating groups have been named by recognized abbreviations which correspond to full chemical names as set forth in the following Table 1.

TABLE 1

Representative Chelating Groups

| Abbreviation | Chemical Name |
| --- | --- |
| EDTA | Ethylenediaminetetraacetic acid |
| DTPA | Diethylenetriamine pentacetic acid |
| TTHA | Triethylenetetramine hexacetic acid |
| DOTA | Tetraazacyclododecane tetraacetic acid (tetracaroxymethyltetraazacyclododecane) |
| TAGA | |
| DOTP | Tetraphosphonatomethyltetraazacyclododecane |
| DTPA-BMA | Bismethylcarbamoylmethyltriscarboxymethyltriazapentane |
| DO2P | Tetraazacyclododecane dimethanephosphonic acid |
| HP-DO3A | Hydroxypropyltetraazacyclododecane triacetic acid |

Figure 12:
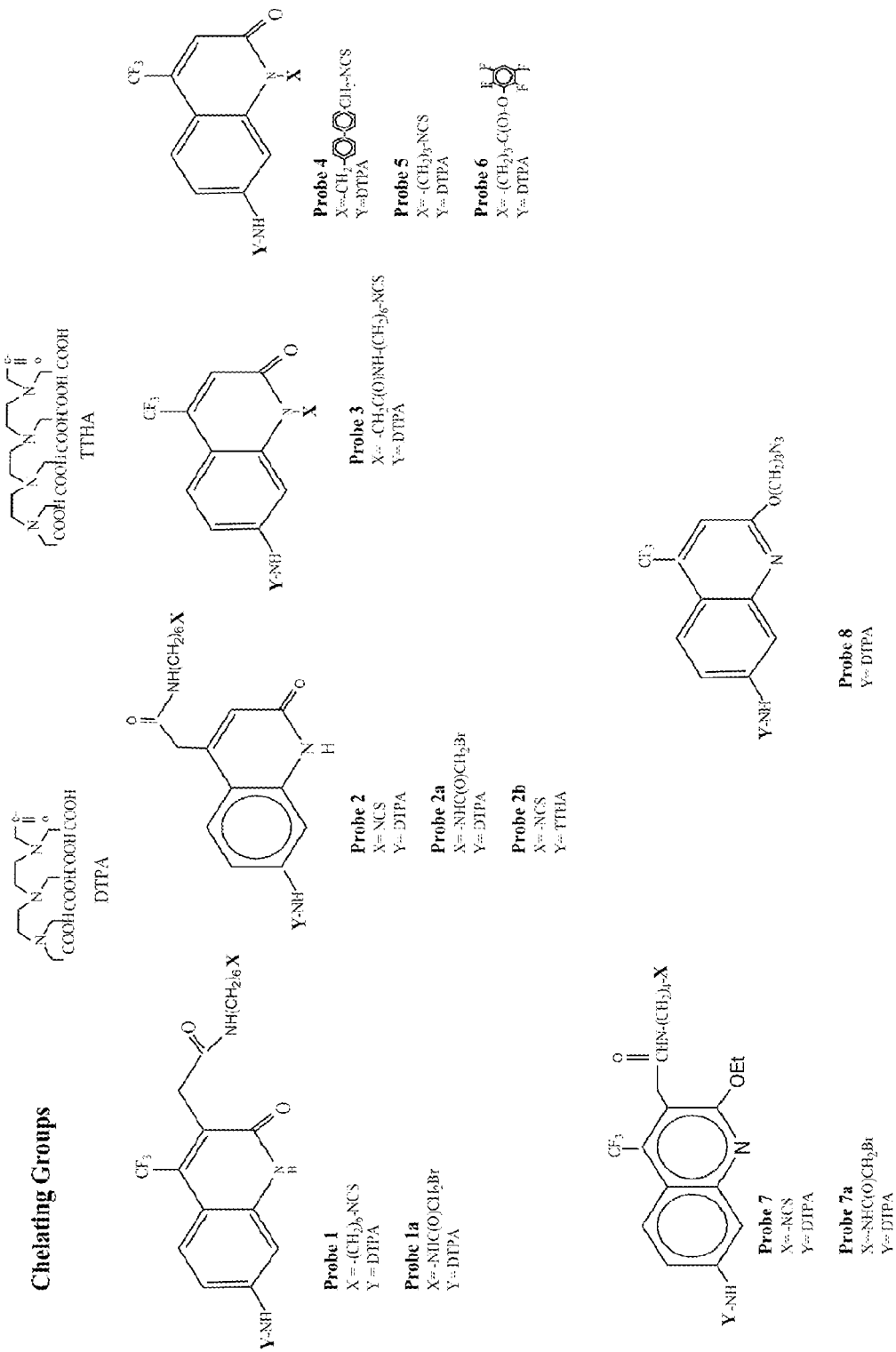
FIG. 12 is a depiction of the chemical structures of several of the fluorophores described herein.

Representative probes of the instant invention are displayed in FIG. 12.

In one embodiment, the compositions for use in the conjugates and methods provided herein include:
(i) a fluorophore of Formula (I) or Formula (II); and
(ii) a chelating moiety covalently joined, optionally through a first linker, to the fluorophore, wherein Formula (I) is:

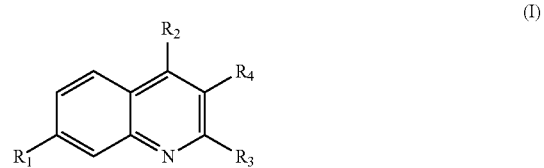

and wherein:
$R_1$ is the site of a covalent attachment, optionally through a linker, of the sensitizer moiety to the chelating moiety;
$R_2$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene, or alkoxylene moieties are optionally further substituted with from 1-4 halogen atoms;
$R_3$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene, or alkoxylene moieties are optionally further substituted with from 1-4 halogen atoms;
$R_4$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, alkylarene, or alkoxylene moieties are optionally further substituted with from 1-4 halogen atoms;
wherein $R_2$, $R_3$, or $R_4$ optionally further contain a cross-linking group selected from the group consisting of isothiocyanate, haloacetate, haloacetamide, nitrogen mustard, epoxide, maleimide, disulfide, activated ester, imidate, azide, acetylenic derivatives, aldehydes, sulfonyl chlorides, acylazides, and acylhydrazides;

and wherein Formula (II) is:

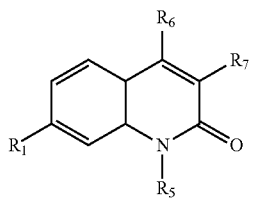

and wherein:
$R_1$ is the site of a covalent attachment, optionally through a linker, of the sensitizer moiety to the chelating moiety;
$R_5$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;
$R_6$ is a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;
$R_7$ is H; a linear alkylene ($C_1$-$C_{20}$), a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;
wherein $R_5$, $R_6$, or $R_7$ optionally further contain a cross-linking group selected from the group consisting of isothiocyanate, haloacetate, haloacetamide, nitrogen mustard, epoxide, maleimide, disulfide, activated ester, imidate, azide, acetylenic derivatives, aldehydes, sulfonyl chlorides, acylazides, and acylhydrazides.

In one embodiment, the composition of matter includes Formula (I) wherein $R_2$ is selected from the group consisting of $CF_3$, $CH_3$, and $OCH_2CH_3$. The composition can also have the Formula (I) where $R_3$ is selected from the group consisting of $CF_3$, $OCH_2CH_3$, and O—$(CH_2)_3$—$N_3$. The composition can also have the Formula (I) where $R_4$ is selected from the group consisting of H, $CH_2C(O)NH$—$(CH_2)_4$—N=C=S, and $CH_2C(O)NH$—$(CH_2)_4$—$NHC(O)CH_2Br$.

In other embodiments the composition of matter can have a fluorophore with the formula

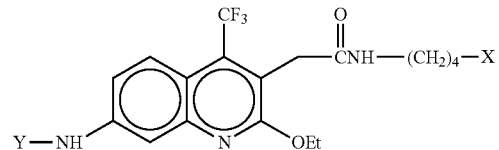

where Y is a chelating moiety and X is selected from the group consisting of N=C=S and $NHC(O)CH_2Br$.

In another embodiment, the composition of matter can have a fluorophore with the formula

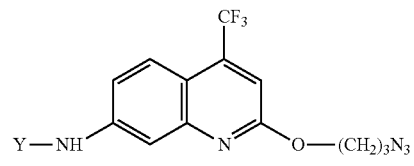

where Y is a chelating moiety.

In another embodiment, the composition of matter includes Formula (II) wherein $R_5$ is selected from the group consisting of H, $CH_2C(O)NH$—$(CH_2)_6$—N=C=S, $(CH_2)_3$—N=C=S,

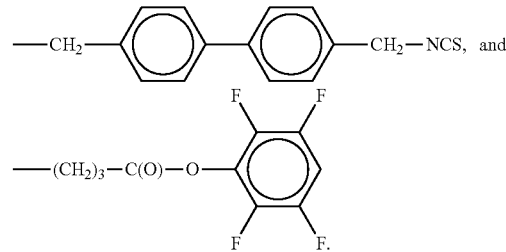

The composition of matter can also have the Formula (II) where $R_6$ is selected from the group consisting of $CH_3$, $CF_3$, $CH_2C(O)NH$—$(CH_2)_6$—N=C=S, and $CH_2C(O)NH$—$(CH_2)_6$—$NHC(O)CH_2Br$. The composition of matter can also have the Formula (II) where $R_7$ is selected from the group consisting of H and $CH_2C(O)NH$—$(CH_2)_6$—N=C=S, and $CH_2C(O)NH$—$(CH_6)$—$NHC(O)CH_2Br$.

In another embodiment, the composition of matter can have a fluorophore with the formula

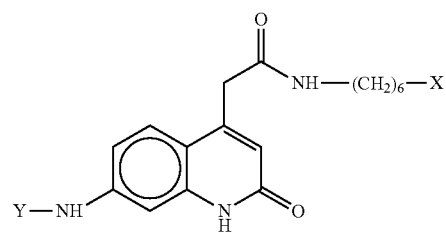

where Y is a chelating moiety, and X is selected from the group consisting of N=C=S and NHC(O)CH$_2$Br.

In another embodiment, the composition of matter can have a fluorophore with the formula

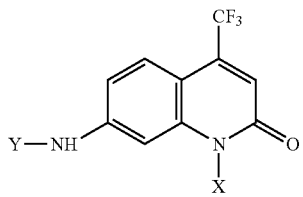

where Y is a chelating moiety, and X is CH$_2$C(O)NH—(CH$_2$)$_6$—N=C=S.

In another embodiment, the composition of matter can have a fluorophore with the formula

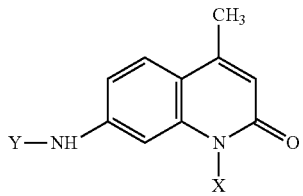

where Y is a chelating moiety, and X is selected from the group consisting of (CH$_2$)$_3$—NCS,

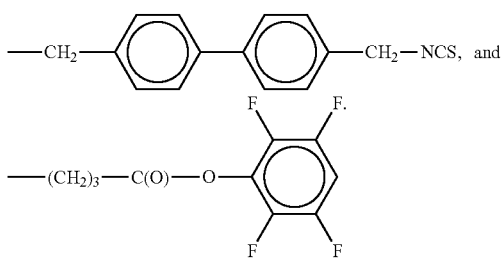

In some embodiments, the composition of matter can contain a chelating moiety including EDTA, DTPA, TTHA, DOTA, TAGA, DOTP, DTPA-BMA, DO2P, and HP-DO3A.

In certain embodiments, the conjugating group has the Formula —S=C=N— or —C(O)—CH$_2$—Br. In some embodiments, any of the above described compositions can further contain a metal ion. In certain embodiments, the metal ion is a trivalent metal ion. In certain embodiments, the metal ion can be, but is not limited to: Gd(III), Dy(III), Ho(III), Er(III), Eu(III), Tb(III), Sm(III), Ce(III), Pr(III), Yb(III), Tm(III), Nd(III), and Tb(IV). In certain embodiments, the metal ion is a lanthanide. In some embodiments, the metal ion is Tb(III) or Eu(III) (also referred to herein as Tb3+ or Eu3+ respectively).

In some embodiments, the above-described compositions have a linker moiety. In some embodiments, the above-described compositions have a linker moiety of the Formula —NH—. In another embodiment, the above-described compositions have a linker moiety that is a heterocyclic alkylene moiety having the formula N$_2$C$_4$H$_8$, and where the covalent linkages occur through the N atoms.

In some embodiments, the chelating moiety is covalently joined to the fluorophore moiety or to the linker moiety through a N atom of the chelating moiety. In other embodiments, the chelating moiety is covalently joined to the fluorophore moiety or to the linker moiety through a carbonyl group of the chelating moiety.

In some embodiments, the linker moiety has the chemical formula —(CH$_2$)$_n$—, and n is an integer from 1 to 20 (e.g., 1, 2, 3, 4, 5, 6, 7, 8, 9, 10, 11, 12, 13, 14, 15, 16, 17, 18, 19, or 20; 1-3, 1-4, 1-5, 1-8, 1-10, 5-10, 5-12, 5-15, 10-15, 15-20). In certain embodiments, the linker has Formula —(CH$_2$)$_n$— where n is 4. It is understood that the length of the linker moiety will depend on a variety of factors including, but not limited to, the macromolecule that can be covalently joined to the above described compositions.

In some embodiments, the compositions of matter can be conjugated to a macromolecule. The macromolecule can be a polypeptide (e.g., an antigen or antigen-binding fragment there, or a polypeptide ligand for a cellular receptor), or a nucleic acid (e.g., DNA or RNA). In certain embodiments, the polypeptide is conjugated to multiple luminescent compositions described herein at multiple conjugation sites. In some embodiments, the number of luminescent compositions conjugated to a polypeptide can be up to about 10, 20, or more. In certain embodiments, the polypeptide can be, but is not limited to, avedin or streptavidin (see Example 10 below).

Preparation of the Compounds

In another aspect the present invention provides new synthetic strategies that enable the preparation of highly luminescent probes with high yield. The resulting probes are ready-to-use, since they contain pre-bound lanthanides, unlike the lanthanide-labeled probes utilized in earlier applications, such as those disclosed in WO 2008/019403, in which the biomolecule of interest was first modified with metal-free chelates, followed by the addition of a lanthanide. The new compounds were tested in the form of molecular beacons, which are widely utilized nucleic acid hybridization probes. The Examples (below) demonstrate a higher sensitivity of detection than can be achieved with conventional fluorescence-based molecular beacons. Moreover, the detection sensitivity is 10 to 60 times better than previously reported for other lanthanide-based hybridization probes. In certain embodiments, the brightness of the probes significantly increases in heavy water, enabling the use of this medium to increase the sensitivity of detection. Because of the superior properties, these new compounds can also be used as luminescent labels in other biopolymers, such as proteins and polysaccharides, as well as labels for small compounds, such as drugs and cellular metabolites.

The compositions for use in the pharmaceutical compositions and methods provided herein can be prepared by the methods shown herein, or by routine modification of these methods using the appropriate starting materials. Specific methods for generating the compositions of matter described herein are detailed in the schemes below.

Scheme 1

Probes 1, and 1a. High brightness with $Eu^{3+}$

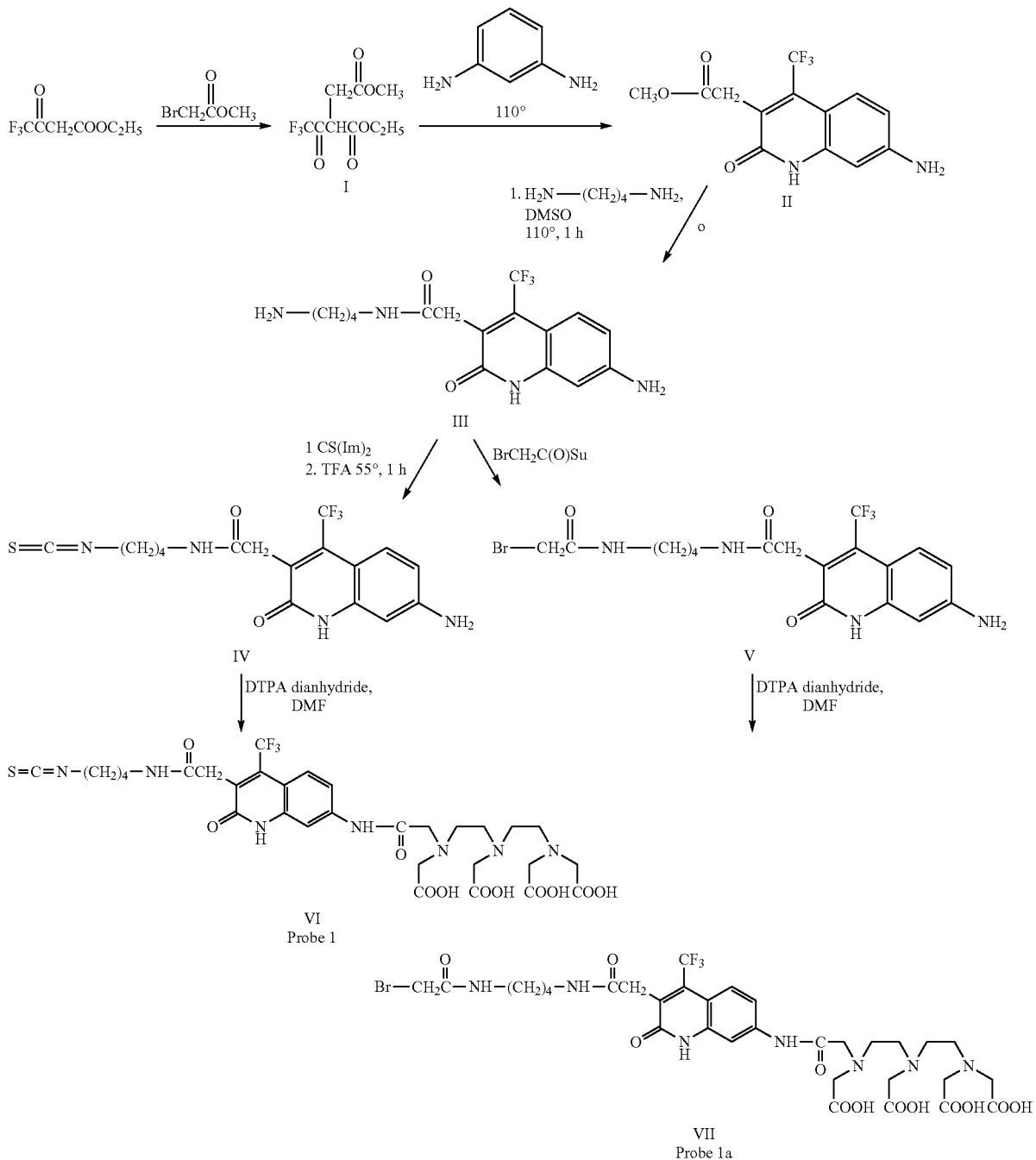

Scheme 1 represents the synthetic scheme for probes 1 (amine-reactive) and 1a (thiol-reactive). These probes are derivatives of previously described cs124 and cs124-CF$_3$ fluorophores, which can be converted to lanthanide chelates possessing highly bright $Eu^{3+}$ luminescence. This process provides reactive cross-linkable derivatives of this $Eu^{3+}$ chelate capable for coupling to biopolymers. The synthesis of these compounds is approached based on the condensation of 1,3-phenylenediamine with an ester of acetoacetic acid derivative. Alkylation of trifluoroacetoacetate by methylbromacetate in the presence of a proton acceptor produces trifluoroacetylmethylethylcuccinate I. Reaction of the latter with 1,3-phenylenediamine produces fluorescent quinolone derivative II, which is converted to aminoalkyl compound III by incubation with a corresponding diamine. This derivative is converted to isothiocyanate IV by subsequent treatment with thiocarbonyldiimidazole and trifluoroacetic acid. Under these conditions the aromatic aminogroup of the compound remains intact. Acylation of compound IV by DTPA anhydride in anhydrous medium followed by hydrolysis of the second anhydride group produces compound VI (probe 1) that is subsequently separated from the excess of DTPA by partitioning in butanol/water. Further addition of aqueous lanthanide trichloride to butanol extract leads to complexation of a lanthanide to the probe. The lanthanide complexes were analyzed and purified by HPLC or by TLC in an acetonitrile—water developing system that is highly efficient (see Scheme 2). Thiol-reactive probe 1a is obtained by essentially the same process through the reaction of III with 4-nitrophenylbromoacetate and subsequent acylation of the resulting compound V with DTPA anhydride.

Scheme 2

Probes 2, 2a, and 2b. Exceptional brightness with $Tb^{3+}$, good efficiency with $Eu^{3+}$

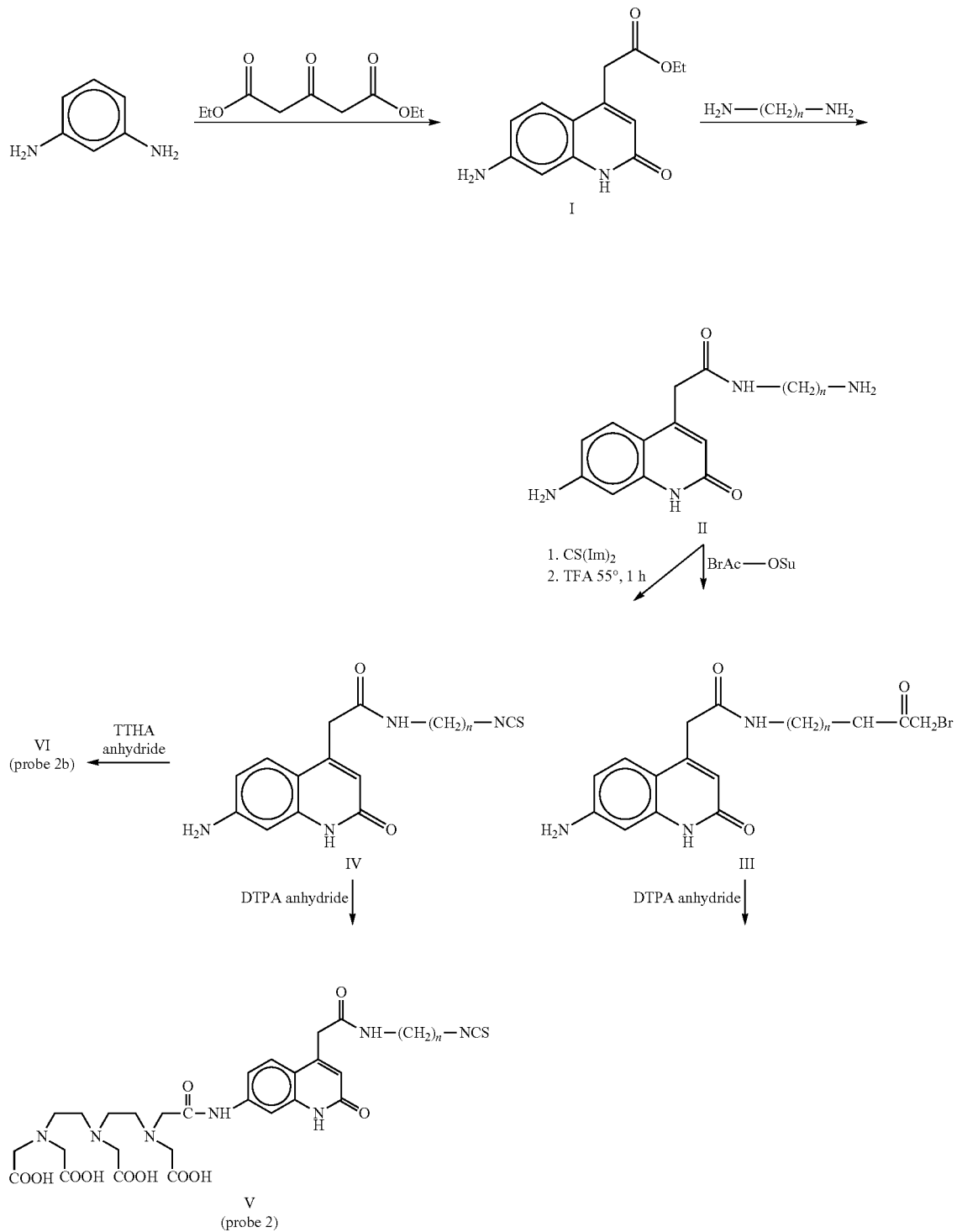

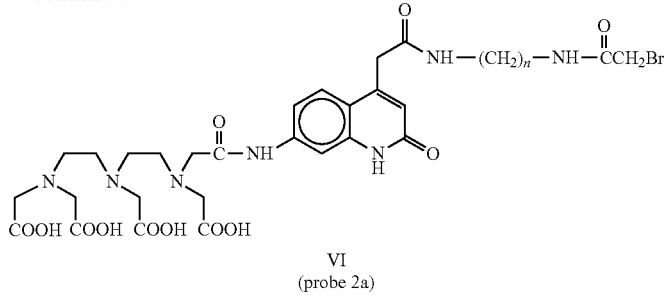

VI
(probe 2a)

For Probes 2, 2a and 2b (Scheme 2), the yield of principal synthetic intermediate, compound I (60%) is greatly increased compared to other protocols (<1%) by using a Lewis catalyst (e.g., $ZnCl_2$). The reaction of this product with a diamine (taken in few-fold excess to avoid cross-linked products) at high temperature results in formation of aminoalkyl derivative II with nearly quantitative yield. Cross-linkable DTPA derivatives (probes 2 and 2a) are obtained as in the case of probe 1. Treatment of compound IV by TTHA dianhydride produced probe 2b of Scheme 1.

The following synthetic reaction schemes (Schemes 3-6) take advantage of the newly discovered alkylation reaction of quinolones that readily proceeds at endocyclic aminogroup or exocyclic oxygen at alkaline conditions. This opens new previously unknown synthetic routes to introduce various cross-linking groups at the N-1 position. Thus, alkylation of $CF_3$cs124 by methylbromoacetate (Scheme 4) leads to compound I, which is converted to reactive probe 3 by treatment with diamine and subsequent reactions with thiocarbonyldi-imidazole and DTPA, anhydride as described above.

Scheme 3

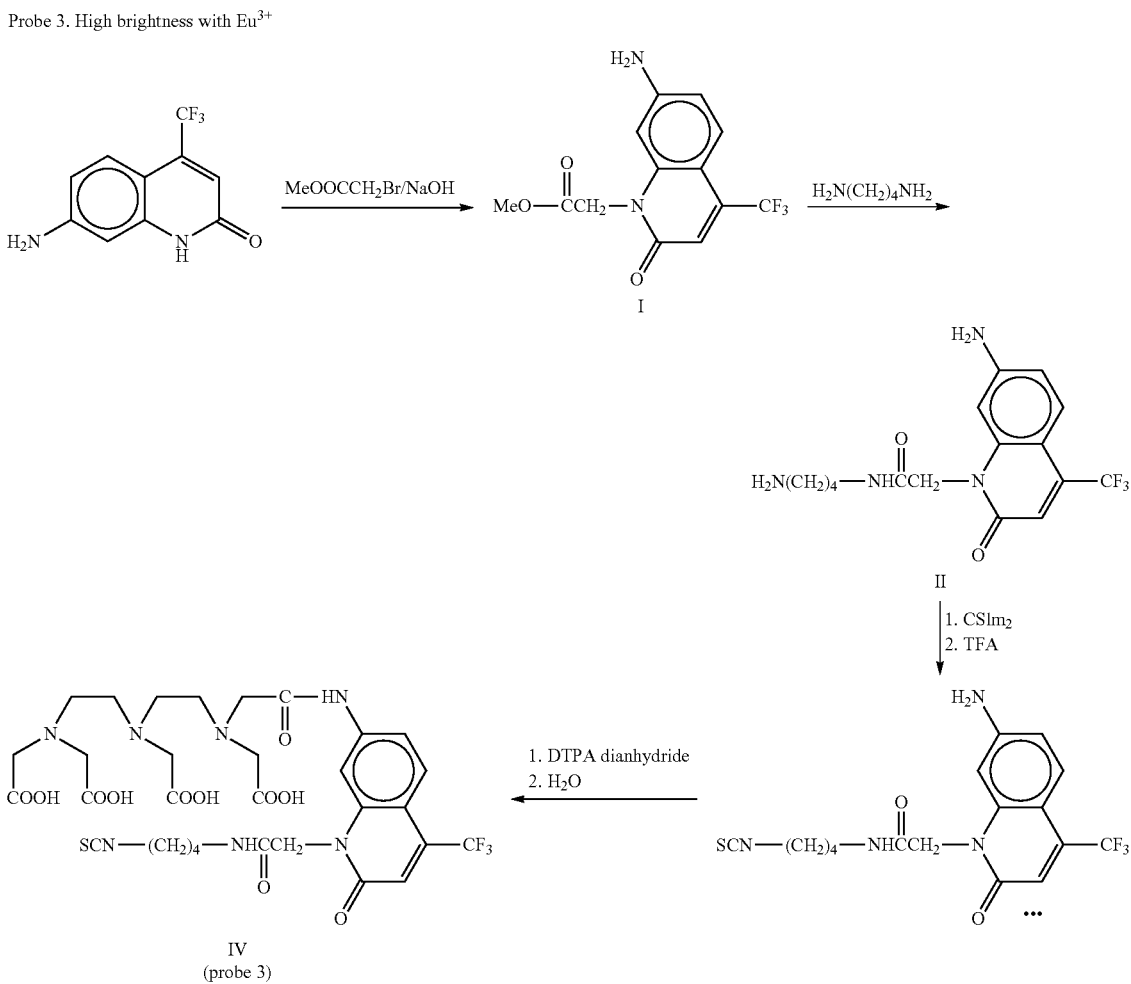

IV
(probe 3)

Attachment of lanthanide probes to nucleic acids strongly reduces the luminescence efficiency (up to 10 times). Without wishing to be bound by theory, this effect is most likely due to stacking of the antenna fluorophore of the probe to DNA (RNA) nitric bases, which effects the fluorescence properties of the antenna and energy transfer to lanthanide. To avoid this effect, a biphenyl moiety is introduced into the cross-linking spacer (Scheme 4), which can compete with stacking of the antenna fluorophore to nucleic acid nitric bases, displaying a "decoy" effect. Indeed, as demonstrated in the Examples below, this probe is much brighter (comparing to the same probe with linear non-aromatic spacer) after coupling to DNA. The biphenyl spacer is chosen because it cannot stack to antenna fluorophore, and therefore does not cause self-quenching.

Scheme 5 represents a synthetic scheme for probe 5, which is a variation of the strategy shown in Schemes 3 and 4. Scheme 5 takes advantage of alkylating compounds containing an azidogroup, which can be subsequently converted to a corresponding amino derivative, a synthetic intermediate for introduction of the cross-linking groups (e.g., isothiocyano group as shown in the scheme).

Scheme 4

Probe 4. Exceptional brightness with $Tb^{3+}$. Enhanced performance in the context of molecular beacon hybridization probe.

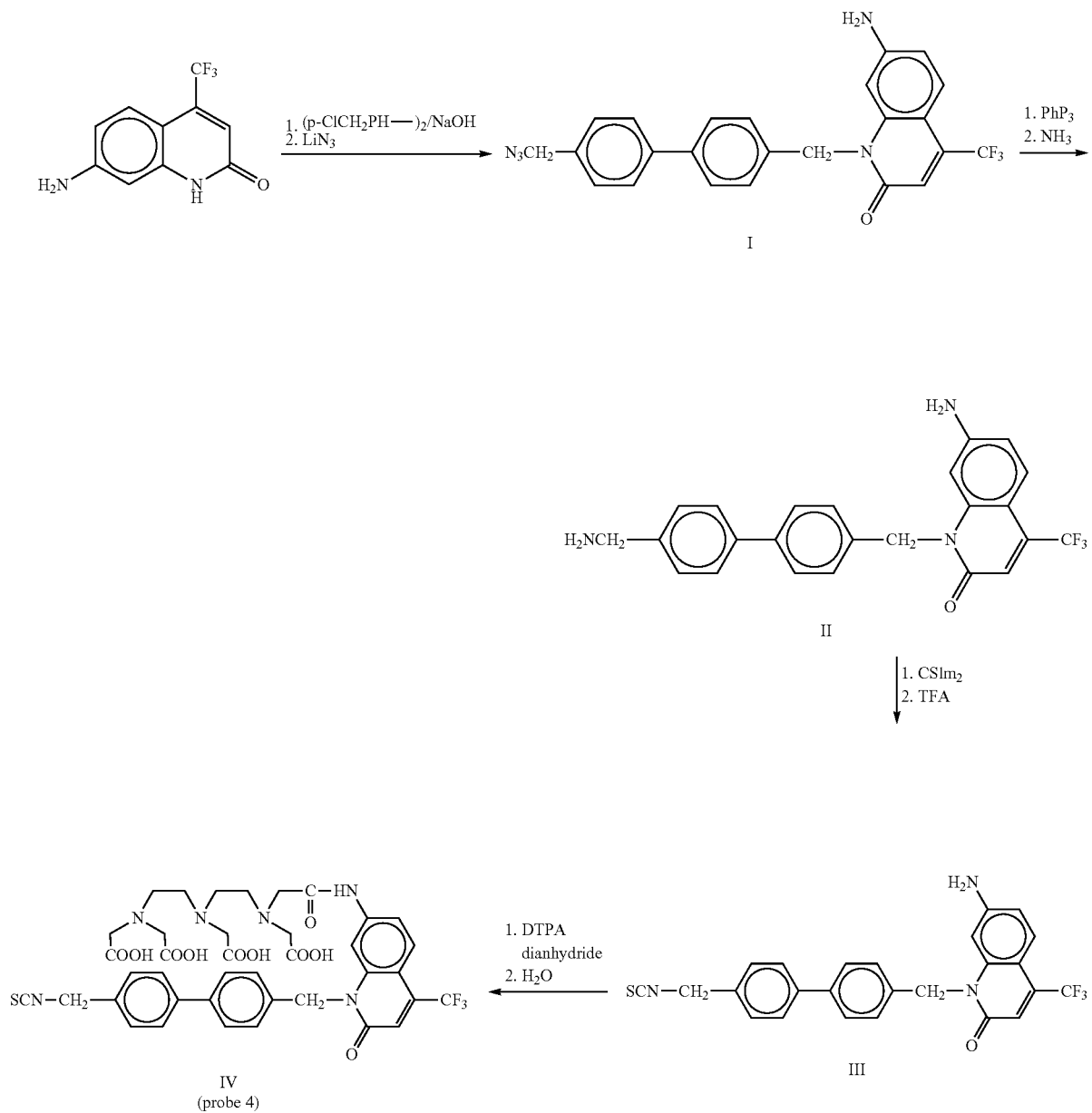

IV
(probe 4)

Scheme 5

Probe 5. Exceptional brightness with $Tb^{3+}$.

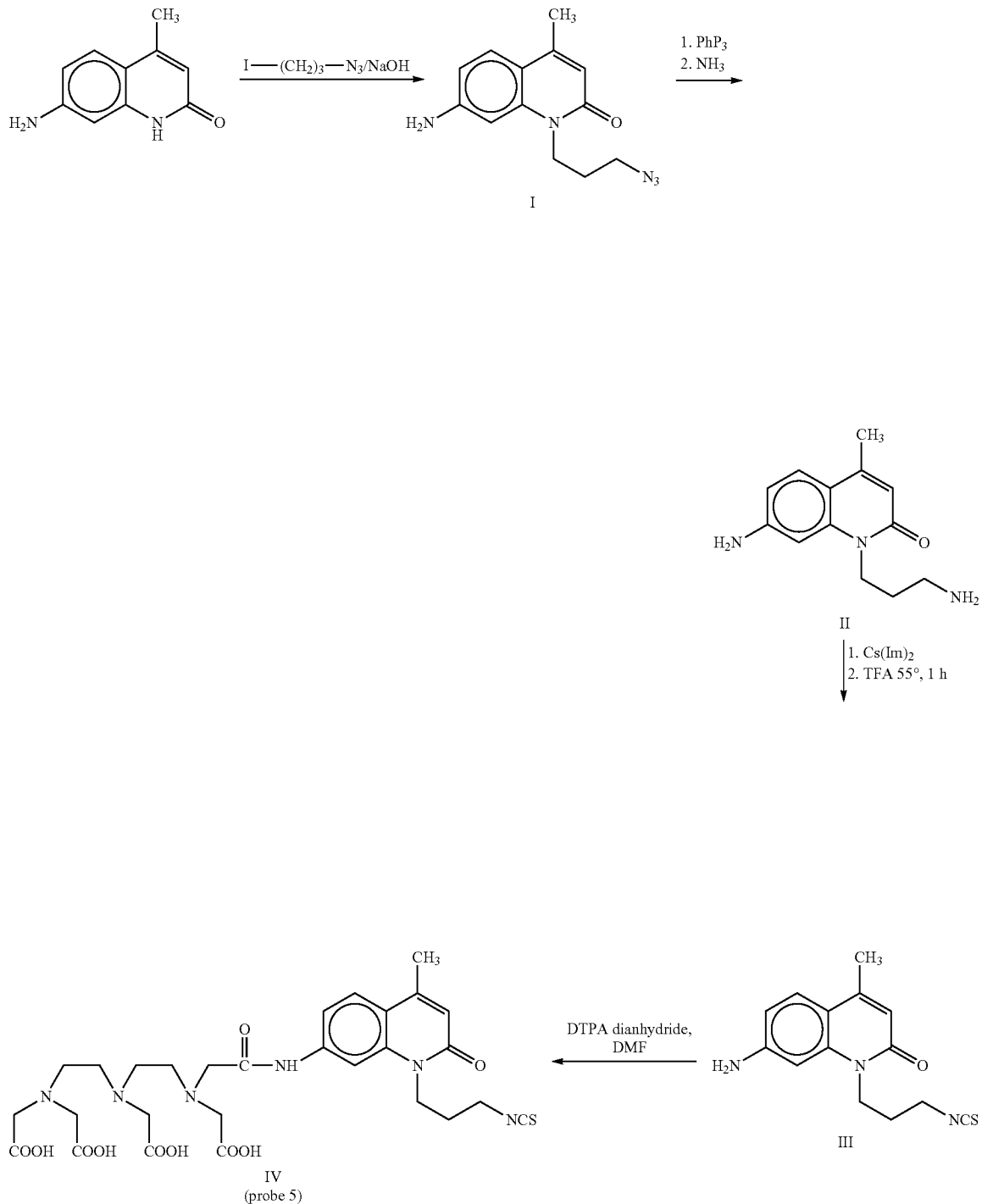

IV
(probe 5)

Probe 6 (Scheme 6) contains an amine-reactive acylating cross-linking group that enables coupling to biopolymers in mild conditions compared to the probes with a moderately reactive isothiocyano group. The synthetic strategy takes advantage of the alkylation of the fluorophore by reacting an iodoalkyl derivative of an esterified acid at the heterocyclic nitrogen followed by saponification of the alkylation product. The carboxyl group of the compound is further converted into amine-reactive ester, that is finally modified by dianhydride at conditions where the ester group remains essentially intact. Corresponding lanthanide-containing probes allow coupling to biopolymers at mild conditions, which is crucial when thermostability of the modified protein is an issue.

Scheme 6

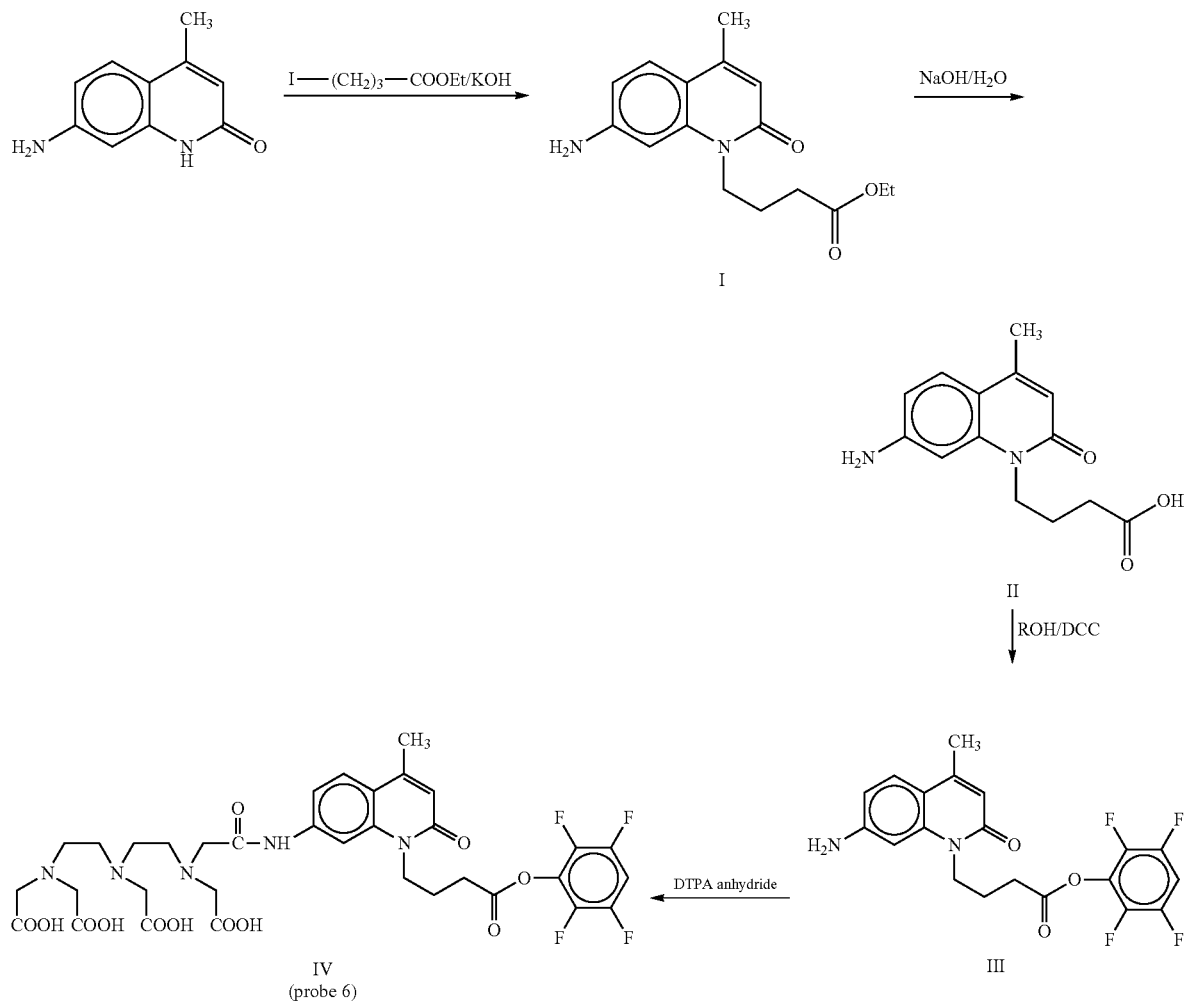

Probes 7 and 7a (Scheme 7) are based on newly discovered antenna fluorophores, which were found in the reaction mixture set up for the synthesis of the probe 1 fluorophore (see Scheme 1, step 2) at lower temperature, 50° C. (comparing to 110° C. for probe 1 fluorophore). The rest of synthetic steps are analogous to those for probe 1, and 1a of Scheme 2. This fluorophore is able to sensitize emission for both $Tb^{3+}$ and $Eu^{3+}$ with efficiency comparable to that of probe 1, which is advantageous in some biological applications (e.g., differential proteomics studies).

Scheme 7

Probes 7, and 7a. Nearly equal brightness with both $Tb^{3+}$ and $Eu^{3+}$

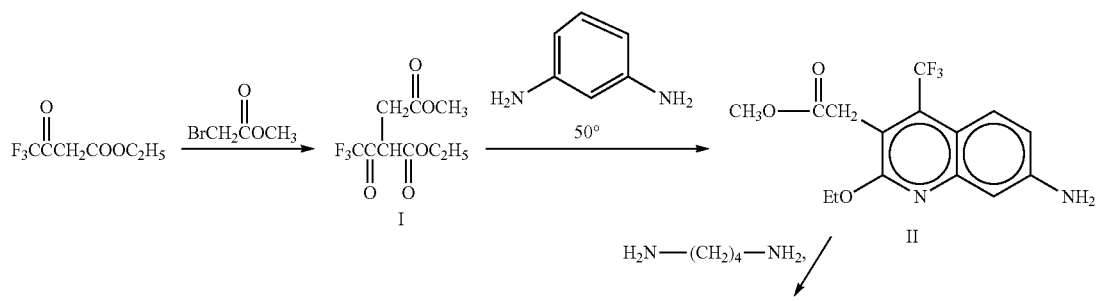

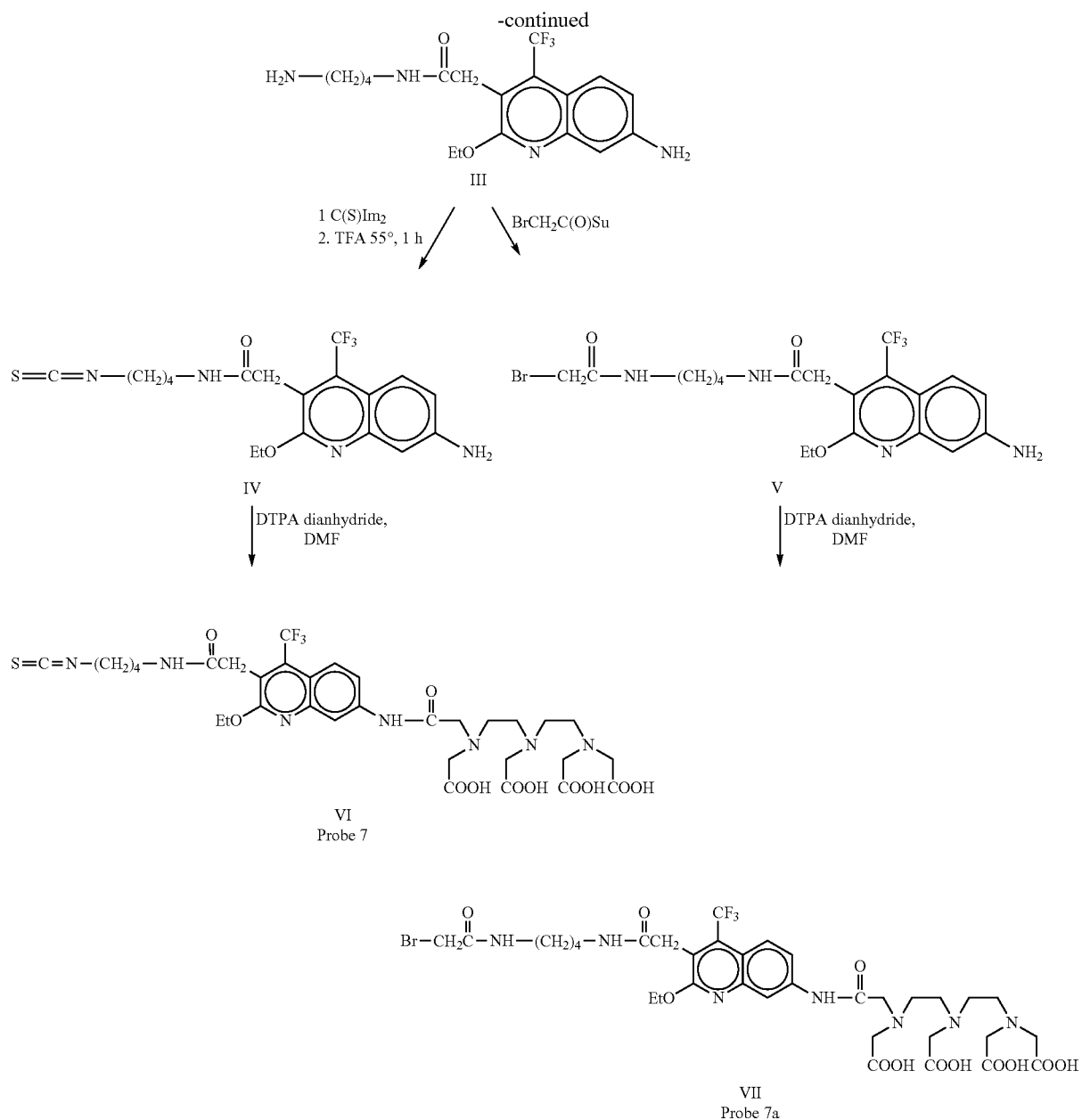

While the alkylation of fluoroquinolones mostly proceeds at the endocyclic nitrogen (75%), minor reaction products corresponding to the alkylation at exocyclic oxygen is also observed (Scheme 8). This product (probe 8) is useful as an antenna for sensitized lanthanide emission. The azido group of the compound is able to form a crosslink with acetylenic derivatives in Cu⁺-mediated reactions known as "click chemistry."

Scheme 8

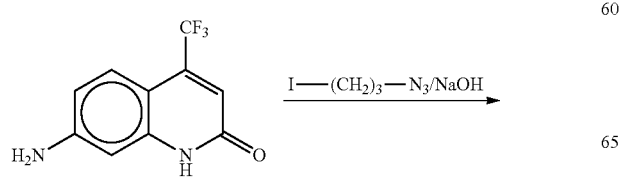

-continued

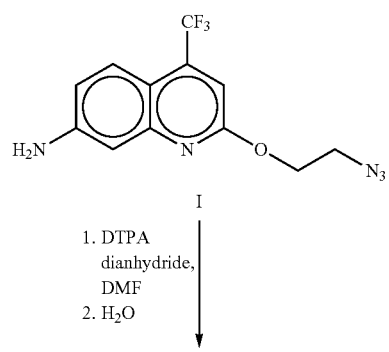

1. DTPA dianhydride, DMF
2. H₂O

-continued

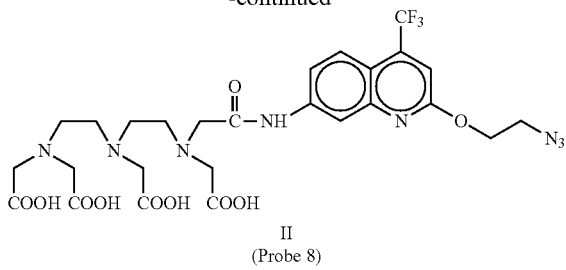

II
(Probe 8)

In Vitro Methods of Detection

Provided herein is an in vitro method of detecting a target with a probe as well as compositions useful in the in vitro detection methods. The method includes the steps of: (a) contacting a sample with a luminescent probe compositions, which includes a targeting-probe moiety having an affinity for a target, the targeting-probe moiety covalently conjugated to a luminescent chelate composition that includes (i) a fluorophore of Formula (I) or Formula (II), and (ii) a chelating moiety covalently joined, optionally through a first linker, to the fluorophore; and (b) detecting a signal produced from the luminescent probe composition.

In some embodiments, the $R_1$ chelating moiety is selected from the group consisting of EDTA, DTPA, TTHA, DOTA, TAGA, DOTP, DTPA-BMA, DO2P, and HP-DO3A. In other embodiments, the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV).

The sample can contain one or more cells, cellular material (e.g., a whole cell lysate), or can contain one or more purified and/or recombinant protein and/or cellular nucleic acid. The sample can also contain only buffer (e.g., phosphate-buffered saline) (e.g., where the sample is used as a negative control). The luminescent probe composition can contain any of the luminescent chelate compositions described herein. The subject can be any subject described herein (see below). Detection can include detecting luminescence emissions from the luminescent probe composition, detecting fluorescence emissions from the fluorophore of the luminescent probe composition, or detecting both luminescence and fluorescence emissions from the luminescent probe composition.

In some instances, the methods and compositions can be useful for scientific research, for example, for identifying the subcellular localization (e.g., nuclear or cytoplasmic localization) of a new protein or known protein (e.g., NF-KB or p53) or messenger RNA. The methods and compositions can also be used, for example, to detect the infection of a cell by a virus, bacterium, or other infectious microbe in studies of infectivity (or prevention of infection) (see, for example, Tardif et al. (2003) J. Virol. 77(22): 12299-309). Other research uses for the detection methods include detecting the presence of a particular polypeptide as expressed by a cell or by a tissue. Expression of the gene can be protein or mRNA expression, and their differential detection using the appropriate conjugates (e.g., conjugates of the luminescent chelates and an antibody or nucleic acid) is described in detail below. The methods and compositions can also be useful in conjunction with separation techniques including, but not limited to, cell-sorting (e.g., fluorescence-assisted cell sorting (FACS)), chromatography, or electrophoretic, osmotic, or centrifugal separations.

The in vitro detection methods and compositions can also be useful in diagnostic assays or tests to, for example, detect or screen for disease biomarkers present in a sample. Such compositions and methods can be used to diagnose patients through the analysis of patient samples (e.g., to detect evidence of viral or bacterial infection, or the presence of cancer cells) (see, for example, Boshell et al (2002) Biomedica 22(1):30-38). It is contemplated that samples (e.g., obtained or provided from a subject (e.g., a human patient)) can be blood, urine, lymph fluid, cerebral spinal fluid, amniotic fluid, vaginal fluid, semen and stool samples. Samples can also be obtained or provided from resected tissue or biopsy material including needle biopsy. Tissue section preparation for surgical pathology may be frozen and prepared using standard techniques. Immunohistochemistry and in situ hybridization binding assays on tissue sections are performed in fixed cells (see below). Cells may be isolated from fluid sample by various procedures such as centrifugation or filtration. Numerous other techniques are available for obtaining tissue samples, and are well known to those in the art, for example, test samples can be obtained by such methods as withdrawing fluid with a syringe or by a swab.

In some embodiments of the compositions and method, the probe moiety covalently joined to a luminescent moiety is an antibody, or antigen-binding fragment of an antibody, or DNA/RNA aptamer nucleic acid sequence having affinity to any biomolecule of interest. Antibodies or antibody fragments that bind to specific target antigens of interest can be generated by immunization, e.g., using an animal, or by in vitro methods such as phage display as well as aptamers obtained by the Systematic Evolution of Ligands by Exponential Enrichment (SELEX). As used herein, "target antigen" refers to the antigen bearing the epitope that a specific antibody or aptamer recognizes.

The imaging methods of the invention using the antibody- or aptamer-based probes, and their luminescent conjugates, embrace numerous modes of detection. In one embodiment, immunohistochemistry or SELEX techniques can be used to identify and essentially stain cells with one or more antigens or other targets recognized by the conjugated antibodies or aptamers. Such "staining" allows, for example, for analysis of viral or bacterial infection of a cell (e.g., if the antibody or aptamer specifically recognizes an epitope in a bacterial or viral antigen) or to identify a normal versus a cancer cell (e.g., if the antibody or aptamer recognizes an epitope specifically expressed in a normal or a cancer cell (e.g., a cancer cell expressing the Melanoma Antigen (MAGE)). Live or fixed cells can be contacted with antibodies or aptamers specific for the target antigen (e.g., anti-MAGE antibodies), wherein the target antigen (e.g., MAGE), if present in the target cells (e.g., the melanoma cells), are recognized and bound by the antibodies or aptamers. The primary antibodies (i.e., the antibodies that specifically recognize the antigen (e.g., the MAGE antigen) can be detectably labeled (covalently joined) directly with one or more of the luminescent moieties, or detection can occur using an secondary (anti-IgG) antibody or, for example, Protein-A or Protein-G that has been detectably labeled (covalently joined) with one or more luminescent moieties. In certain embodiments, the labeling can also be achieved through biotinylation of an antibody or aptamer followed by coupling with streptavidin/avidin derivatized with multiple luminescent residues.

Detection of a polypeptide in a test sample is routine and one of ordinary skill in the art can detect the presence or absence of a protein or an antibody using well known methods. In another embodiment, the antibody/aptamer probe conjugates described herein can be used in immunoassay methods to detect the presence of an antigen in a sample. According to some embodiments, immunoassays comprise allowing proteins in the sample to bind a solid phase support such as a plastic surface. Detectably-labeled antibodies (i.e., antibodies conjugated to the luminescent moieties) are then added and selectively bind to their cognate antigens. Detection of the detectable (i.e., luminescently-labeled) antibody indicates the presence of the antigen in the sample. The detectable antibody may be a labeled or an unlabeled antibody.

This same approach may be employed with aptamer arrays that are conventionally fabricated on microchip slides. The analyte containing a presumed pathogen, or a mixture of unknown pathogens, is labeled with luminescent probes and brought into contact with a microarray of aptamers specific to expected microbial pathogens. This results in the specific binding of a labeled pathogen with a particular segment of microarray, whose position on the slide will identify the pathogen, while the intensity of the luminescent signal of bound labeled cells indicates their quantity in the analyzed sample. In one embodiment, this approach is employed as a diagnostic platform for express pathogen detection in clinical and biodefense applications.

Unlabeled antibody may be detected using a second, labeled antibody that specifically binds to the first antibody or a second, unlabeled antibody which can be detected using labeled protein A, a protein that complexes with antibodies. Various immunoassay procedures are described, for example, in Voller et al., Eds., University Park, 1981, which is hereby incorporated by reference in its entirety. Immunoassays may be performed in which a solid phase support is contacted with the test sample. Any proteins present in the test sample bind the solid phase support and can be detected by a specific, detectable antibody preparations, examples of such techniques include the dot blot, Western blot and other similar assays variants. Western blot techniques, are described, for example, in Sambrook, J. et al., (1989) Molecular Cloning: A Laboratory Manual, Cold Spring Harbor Laboratory Press, Cold Spring Harbor, N.Y.

Other, more complex, immunoassays include, for example, "sandwich" assays for the detection of a protein in which a first anti-protein antibody bound to a solid phase support is contacted with the test sample. After a suitable incubation period, the solid phase support is washed to remove unbound protein. A second, different anti-protein antibody is then added which is specific for a portion of the specific protein not recognized by the first antibody. In this case, the secondary antibody is preferably detectably-labeled with the luminescent moiety. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds specifically to the second antibody (but not the first antibody) is added to the system.

The results from this type of assay can be a simple yes/no answer or can be expressed as, for example, (a) one or more of "excellent", "good", "satisfactory", "unsatisfactory", and/or "poor"; (b) one or more of "very high", "high", "average", "low", and/or "very low"; or (c) one or more of "+++++", "++++", "+++", "++", "+", "+/−", and/or "−". In this aspect, the assay is a qualitative assay. Alternatively, the assay results can be quantitative by comparing the amount of detectable antibody with that obtained in a control. Examples of such assays are described in Wide et al., Radioimmune Assay Method, Kirkham, Ed., E. & S. Livingstone, Edinburgh, 1970, pp. 199-206, which is incorporated by reference in its entirety. Other types of immunometric assays include "simultaneous," "reverse" assays.

The first component of the immunometric assay may be added to nitrocellulose or other solid phase support which is capable of immobilizing proteins. "Solid phase support" or "support" as used herein refers to any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead (e.g., agarose, sepharose, or magnetic beads), or cylindrical, as in the inside surface of a test tube or the external surface of a rod. One of skill in the art would know many other suitable "solid phase supports" for binding proteins. For example, a preferred solid phase support is a 96 or 386-well microtiter plate.

Detection of the protein-specific antibody, an antigen-binding-fragment thereof, or a derivative thereof can be accomplished using a fluorometer if, for example, one or both of the fluorescent sensitizer moieties are to be detected, or using a luminometer, if the emissions from the luminescent moiety is to be detected. Positive and negative controls may be performed in which known amounts of one or more antigens are added to assays being performed in parallel with the test assay. One skilled in the art would have the necessary knowledge to perform the appropriate controls.

Alternatively, in some embodiments, the probe moiety can be a ligand for a cellular receptor. Examples of such ligands that can be conjugated to a luminescent moiety described herein, and useful for the method include, but are not limited to: cytokines (e.g., Interferons (e.g., IFN-gamma), IL-2 subfamily cytokines, IL-10 subfamily cytokines, IL-1 subfamily cytokines, IL-17 subfamily cytokines, and Tumor Necrosis Factor); growth factors (PDGF, EGF, TGF-alpha, FGF, NGF, Erythropoetin, TGF-beta, IGF-I, IGF-II, G-CSF, GM-SCF, thrombopoietin, and myostatin); and viruses or viral proteins (e.g., viral surface or coat proteins, e.g., gp160 or p24 of HIV-I). In other embodiments, the ligand can also be a small molecule (e.g., an androgen (e.g., testosterone for binding to the androgen receptor), estrogen, progesterone, glucocorticoids, or corticosteroids). Where the small molecule is an orphan compound (i.e., a compound with a known function but no identified cellular target), the methods can be used to identify the cellular target of the orphan compound (e.g., the enzyme target of the compound). Suitable detection methods for ligand-based luminescent conjugates are well known to those in the art and include some of the methods described above. Briefly, a ligand conjugate can be added to a sample for an amount of time sufficient to allow for the binding of the ligand to its cognate receptor, followed by detecting the emissions from the luminescent moiety or fluorescent emissions from one or both fluorescent sensitizer moieties. Optionally, the ligand can be unlabeled and a detectably-labeled antibody (such as one described above) can be used to detect the presence of the ligand.

In some embodiments, the probe moiety is a nucleic acid (e.g., RNA or DNA). Suitable uses for luminescently conjugated nucleic acids include, for example, mRNA sequence-based methods of detection including, but are not limited to, Reverse-transcriptase-polymerase chain reaction (RT-PCR) technology, branched oligonucleotide technology, Northern and Southern blot technology, in situ hybridization technology (e.g., fluorescence in-situ hybridization (FISH)) and oligonucleotide hybridization technology.

One method of detecting a particular mRNA transcript in genetic material derived from a sample (e.g., human cancer patient sample) uses branched chain oligonucleotide hybridization analysis. Branched-chain oligonucleotide hybridization may be performed as described in U.S. Pat. Nos. 5,597,909, 5,437,977 and 5,430,138.

In another embodiment, detecting an mRNA transcript in a sample using a luminescently-conjugated-nucleic acid probe described herein uses Northern Blot analysis. The techniques for performing Northern blot analyses are well known by those having ordinary skill in the art and are described in Sambrook, J. et al., (1989) Molecular Cloning: A Laboratory Manual, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

Another method of detecting the presence of a given mRNA transcript, embraced by the invention, uses by oligonucleotide hybridization technology. Oligonucleotide hybridization technology is well known to those having ordinary skill in the art (and described in greater detail below). Briefly, detectable probes which contain a specific nucleotide sequence that will hybridize to nucleotide sequence of the mRNA transcript. In one embodiment, RNA or cDNA made from RNA from a sample is fixed to, for example, filter paper. The probes are then added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences. Probes useful in such methods include oligonucleotides at least 18 nucleotides of complementary DNA and may be as large as a complete complementary sequence to the target mRNA transcript. In some preferred embodiments the probes of the invention are 30-200 nucleotides, preferably 40-100 nucleotides. The probes preferably contain a sequence that is unique with respect to the target mRNA sequence. Hybridization conditions can be routinely optimized to minimize background signal by non-fully complementary hybridization. In some preferred embodiments, the probes are full length clones. Probes are at least 15 nucleotides, preferably 30-200, more preferably 40-100 nucleotide fragments and can be the entire mRNA transcript. Oligonucleotide hybridization techniques are useful for detecting an mRNA transcript in homogenized tissue samples and cells in body fluid samples. Furthermore, multiple methods of detection (including both described herein and other suitable detection techniques) can be combined in a given analysis. For example, techniques such as immunohistochemistry assays may be performed to determine whether one or more polypeptide products are present in cells in a sample as well as using, for example, RT-PCR or northern blot analysis to detect the presence of mRNA that encodes the polypeptide.

Additional embodiments of the luminescently-labeled nucleic acids are described in detail below under the section "Use of the Conjugates as Nucleic Acid Probes."

In Vivo Methods of Detection

This invention also features compositions and in vivo methods for detecting a target with a probe (e.g., a target in or on a subject). The methods include the steps of: (a) delivering to a subject a luminescent probe composition comprising a target-probe moiety having an affinity for a target, the targeting-probe moiety covalently conjugated to a luminescent chelate composition including that includes (i) a fluorophore of Formula (I) or Formula (II), and (ii) a chelating moiety covalently joined, optionally through a first linker, to the fluorophore; and (b) detecting a signal produced from the luminescent probe composition.

In some embodiments, the $R_1$ chelating moiety is selected from the group consisting of EDTA, DTPA, TTHA, DOTA, TAGA, DOTP, DTPA-BMA, DO2P, and HP-DO3A. In other embodiments, the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV).

The sample can contain one or more cells, cellular material (e.g., a whole cell lysate), or can contain one or more purified and/or recombinant protein and/or cellular nucleic acid. The sample can also contain only buffer (e.g., phosphate-buffered saline) (e.g., where the sample is used as a negative control). The luminescent probe composition can contain any of the luminescent chelate compositions described herein. The subject can be any subject described herein (see above). Detection can include detecting luminescence emissions from the luminescent probe composition, detecting fluorescence emissions from the fluorophore of the luminescent probe composition, or detecting both luminescence and fluorescence emissions from the luminescent probe composition.

Methods of detection can be any of those described herein (see "Detecting Luminescence and/or Fluorescence of the Compositions" and "Application of the Lanthanide-Based Probes for Tracing Analysis"), and be performed using, for example, a fluoriscope, a luminoscope, nuclear magnetic resonance imaging (MRI), or computed tomography (CT scan).

The methods can be useful in in vivo diagnostics of biomarkers including, for example, tumor antigens (e.g., MAGE-I, MAGE-3, MUC1, FAP-α, Tenascin, Epidermal Growth Factor Receptor (EGFR), $p185^{HER2}$, Her-2/Neu, or CA-125), biomarkers of cardiac disease (e.g., CK, CK-MB, myoglobin, cardiac troponin, LDH, AST, Hs-CRP, or BNP), or biomarkers of neurologic disorders (e.g., tau, transthyretin, or alpha-synuclein). Biomarkers include both nucleic acids (e.g., mRNA) or protein (e.g., expression of a protein by a cell). When the methods are used at one time point (i.e., for one independent measurement), the methods can be used to detect the presence of a disease (e.g., a cancer, a cardiac disease, a microbial infection, or a neurologic disorder). Alternatively, when the methods are repeated for a given subject over time (i.e., biomarker detection in the same subject at various points in time), the methods can be used to detect or quantify the progression of a disease state in a subject (e.g., detect the worsening or amelioration of the disease based on, for example, an increase or decrease in the biomarkers of the diseases). For example, when more MAGE-I is detected in a melanoma at a second time point as compared to the amount of MAGE-I detected on the melanoma initially, this could be an indication that the melanoma is progressing. The methods can also be useful in identifying or imaging in a subject the location of a given target to which the probe is drawn. For example, where the target of the probe is an antigen expressed on or in a tumor cell, or is a bona fide tumor antigen, the methods can be used to locate a tumor in the subject (e.g., find, detect, or identify a metastatic tumor cell or colony of cells). The methods can also be useful in detecting blood clots or thromboses in a subject, by for example, venographies.

Other uses for the method can be cardiac stress tests, lung scans, pulmonary angiograms, and spiral (helical) computerized tomography (CT) scans, as well as detection of microbial pathogens in human specimens, in food, or in environmental sources.

The subject can be any subject described herein.

All of the conjugated probes described herein can be used for the in vivo methods. For example, luminescent probe compositions useful in the method include compositions where the probe is, for example, an antibody, nucleic acid aptamer, ligand, small molecule, or nucleic acid. Suitable probes will vary upon the type of target molecule to which the probe is drawn.

Where the probe moiety is an antibody, it may be useful (e.g., when the intended subject is a human) to partially humanize or fully humanize the antibody probe. The conjugated antibody or antigen binding fragment of the invention may be modified in such a way as to make it more compatible for in vitro or in vivo use. EP 239 400 (Winter et al.) describes altering antibodies by substitution (within a given variable region) of their CDRs for one species with those from another. CDR-substituted antibodies can be less likely to elicit an immune response in humans compared to true chimeric antibodies because the CDR-substituted antibodies contain considerably less non-human components. See Riechmann et al., 1988, Nature 332, 323-327; Verhoeyen et al., 1988, Science 239, 1534-1536. Typically, CDRs of a murine antibody are substituted into the corresponding regions in a human antibody by using recombinant nucleic acid technology to produce sequences encoding the desired substituted antibody. Human constant region gene segments of the desired isotype (e.g., gamma I for CH and kappa for CL) can be added and the humanized heavy and light chain genes can be co-expressed in mammalian cells to produce soluble humanized antibody.

WO 90/07861 describes a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271 use, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from x-ray crystallography and thus specific interactions between CDRs and V region framework residues can be modeled. Non-human antibodies can be modified to include substitutions that insert human immunoglobulin sequences, e.g., consensus human amino acid residues at particular positions, e.g., at one or more (preferably at least five, ten, twelve, or all) of the following positions: (in the framework of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the framework of the variable domain of the heavy chain) 2H, 4H, 24H, 36H, 37H, 39H, 43H, 45H, 49H, 58H, 6OH, 67H, 68H, 69H, 7OH, 73H, 74H, 75H, 78H, 91H, 92H, 93H, and/or 103H (according to the Kabat numbering). See, e.g., U.S. Pat. No. 6,407,213.

Fully human monoclonal antibodies that bind to a V2-CND polypeptide can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798, 230. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; US 2003-0232333).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with a V2-CND polypeptide.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., heavy chain (HC) CDR1, HC CDR2, HC CDR3, light chain (LC) CDR1, LC CDR2, and LC CDR3, can be human. Each of the light chain CDRs can be human. HC CDR3 can be human. One or more of the framework regions (FR) can be human, e.g., FR1, FR2, FR3, and FR4 of the HC or LC. In some embodiments, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions. All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids) are similarly encoded by a variable region gene (about 116 amino acids) and one of the other aforementioned constant region genes, e.g., gamma (encoding about 330 amino acids).

The term "antigen-binding fragment" of a full length antibody refers to one or more fragments of a full-length antibody that retain the ability to specifically bind to a target of interest (i.e., GFRalpha3). Examples of binding fragments encompassed within the term "antigen-binding fragment" of a full length antibody include: (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

Pharmaceutical Compositions and Methods of Delivery of Compositions

The present invention also provides for pharmaceutical compositions containing any of the compositions described herein, or a pharmaceutically acceptable salt thereof, the composition covalently joined to a probe, together with a pharmaceutically acceptable carrier, diluent, or excipient therefor.

Any of the chemical compositions described herein can be incorporated into pharmaceutical compositions. Such pharmaceutical compositions typically include the chemical compositions and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A chemical composition of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds can also be incorporated into the pharmaceutical compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL3 (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating any of the chemical compositions described herein in the required amount in an appropriate solvent with one or a combination of ingredients enumerated above, as required, followed by filtered sterilization. Generally, dispersions are prepared by incorporating the chemical composition into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral pharmaceutical compositions generally include an inert diluent or an edible carrier. For the purpose of oral therapeutic administration, the chemical composition can be incorporated with excipients and used in the form of tablets, troches, or capsules, e.g., gelatin capsules. Oral pharmaceutical compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets contain from 1% to 95% (w/w) of the chemical composition. In certain embodiments, the chemical composition ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the chemical composition with encapsulating material as a carrier providing a capsule in which the chemical composition with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the chemical composition in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the chemical compositions are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The chemical compositions can also be prepared in the form of suppositories (e.g., with conventional suppository bases such as cocoa butter and other glycerides) or retention enemas for rectal delivery.

In one embodiment, the chemical compositions are prepared with carriers that will protect the chemical composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral pharmaceutical compositions in dosage unit form for ease of administration and uniformity of dosage. Dosage unit form as used herein refers to physically discrete units suited as unitary dosages for the subject to be treated; each unit containing a predetermined quantity of a chemical composition calculated to achieve the desired level of detection in association with the required pharmaceutical carrier. Dosage units can also be accompanied by instructions for use.

The dose administered to a subject, in the context of the present invention should be sufficient to achieve a desired level of detection in the subject over time. The dose will be determined by the efficacy of the particular chemical composition employed in detection, the accessibility of the particular target to which the probe is drawn, and the condition of the subject, as well as the body weight or surface area of the subject to be treated. The size of the dose also will be determined by the existence, nature, and extent of any adverse side effects that accompany the administration of a particular chemical composition in a particular subject. For administration, chemical compositions of the present invention can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses. The pharmaceutical compositions can be included in a container, pack, or dispenser together with instructions for administration.

Detecting Luminescence and/or Fluorescence of the Compositions

A variety of radiation sources and radiation wavelengths can be used to excite the luminescent compositions described herein. For example, lamps (e.g., high pressure, mercury, xenon, photodiode, and quartz lamps) and lasers generating radiation having suitable wavelengths can be employed for exciting the luminescent compositions.

Methods of assessing the luminescence intensity of a composition described herein can be quantitative, semi-quantitative, or qualitative. Thus, for example, the emission intensity of a given composition can be determined as a discrete value. Such quantitative methods are well known to those of ordinary skill in the art, and methods are described in the following Examples. Such methods involve, for example, placing a sample into a spectrophotometer, luminometer, or fluorimeter cable of exciting one or both of the sensitizer moieties of the compositions described herein, and detecting (e.g., determining, or measuring) the fluorescent emission from one or both of the sensitizer moieties, and/or detecting the luminescent emissions from the luminescent moiety (e.g., the metal chelate, e.g., the lanthanide). Where the detection occurs in vivo (e.g., in the whole animal), the detection can be performed using, for example, a fluoroscope, a luminoscope, nuclear magnetic resonance imaging (MRI), or computed tomography (CT scan). The excitation light can be constant, or preferably, the excitation light can be pulsed. Excitation of the one or more sensitizer moieties can occur at a range of 400-700 nm and is dependent on the absorption maxima of a particular sensitizer. A luminescent chelate described herein containing a lanthanide, $Tb^{3+}$ for example, can be excited at wavelengths of between 150 and 750 nm, usually between 200 and 650 nm, more usually between 250 and 550 nm, and most often between 300 and 450 nm. Generally, detected emissions are at least 50 nm, usually at least 100 nm, more usually at least 150 nm greater than the incident light. For example, preferred detected emissions for terbium and europium are 492 and 546 nm and 617 and 695 nm, respectively. One of ordinary skill in the art would know how to perform routine experimentation to determine optimal excitation wavelengths for the luminescent compositions depending on the particular sensitizer moiety. Examples of fluorescent emissions and excitation spectra for numerous fluorophore molecules can be found at, e.g., http://probes.invitrogen.corn/servlets/spectra/ (Invitrogen, Carlsbad, Calif., USA).

It is understood that for any of the methods described herein, detection can involve detecting luminescence emissions of the excited luminescent chelate moiety and/or the fluorescence emissions of one or both sensitizer moieties of the luminescent compositions. Fluorescence emissions of the sensitizers (i.e., the fluorophores) can range from 400-700, dependent on a particular sensitizer.

Additional embodiments related to the application of lanthanide-based probes for tracing analysis are described in detail below under the section "Application of the Lanthanide-Based Probes for Tracing Analysis."

Conjugation of the Compositions to Macromolecular Probes

Provided herein are conjugates of any of the chemical compositions described herein and a probe moiety. The macromolecular conjugates of the luminescent compositions described herein are useful for a variety of methods including: immunochemistry, fluorescence in situ hybridization (FISH), cell tracing, receptor labeling and fluorescent analog cytochemistry. In these applications, the stability of the chemical bond between the luminescent composition and macromolecule (i.e., the probe) is particularly important because the conjugate can typically be stored and/or used repeatedly over a relatively long period of time. Moreover, the conjugates can often be subjected to rigorous incubation, hybridization and washing steps that demand a strong composition-macromolecule linkage.

The preferred conjugate usually has a high luminescence and/or fluorescence yield (or, in the case of a haptenylated conjugate, a suitable degree of labeling) yet retains the critical parameters of the unlabeled biomolecule, such as solubility, selective binding to a receptor (e.g., where the probe is a ligand to a particular cognate receptor), a target antigen (e.g., where the probe is an antibody) or nucleic acid (e.g., where the probe is a complementary nucleic acid to the target nucleic acid), activation or inhibition of a particular enzyme or the ability to incorporate into a biological membrane. Following conjugation, it is very important to remove as much unconjugated labeling reagent as possible, usually by gel filtration, gel electrophoresis, dialysis, macromolecule precipitation and resolubilization, HPLC or a combination of these techniques. The presence of free dye, particularly if it remains chemically reactive, can greatly complicate subsequent experiments with the luminescent macromolecular conjugates.

Methods for conjugating any of the compositions described herein with a polypeptide are well known to those of ordinary skill in the art. For example, proteins may be labeled in a variety of ways to allow efficient detection or purification. The labeling methods make use of one or more common functional groups on the surface of protein molecules. Primary amine groups (—NH2), present at the N-terminus of each polypeptide chain and the side chain of lysine residues can be conjugated to a composition. Alternatively, sulfhydryl groups (—SH), present on cysteine residues can be made available by treating disulfide bonds with a reducing agent or by modifying lysine residues with a reagent such as SATA. Particularly useful for conjugation to antibodies, carbohydrate groups, usually present in the Fc region of polyclonal antibodies, may be oxidized to create active aldehydes (—CHO) for coupling (see, for example, Qu et al. (1998) J. Immunol. Meth. 213:131-144. In some embodiments, the chemical compositions described herein are covalently joined to "conjugating moieties." These conjugating moieties are molecules that contain chemically reactive groups that, when reacted with a probe moiety, are capable of joining the chemical composition and the probe moiety. Examples of such conjugating moieties include, but are not limited to, an amine reactive moiety having the chemical formula —N═C═S or a thiol-reactive moiety having the chemical formula —CO—CH2-Br.

Additional methods of conjugation of a composition to a macromolecule or probe include, e.g., succinimidyl esters, carbonyl azides, sulfonyl chlorides and aldehydes.

Succinimidyl esters are excellent reagents for amine modification because the amide bonds they form are as stable as peptide bonds. These reagents are generally stable during storage if well desiccated, and show good reactivity with aliphatic amines and very low reactivity with aromatic amines, alcohols, phenols (including tyrosine) and histidine. Succinimidyl esters will also react with thiols in organic solvents to form thioesters. If formed in a protein, a thioester may transfer the acyl moiety to a nearby amine. Succinimidyl ester hydrolysis can compete with conjugation, but this side reaction is usually slow below pH 9.

Carbonyl azides are active esters that can react with amines to yield amides; however, a more common application of carbonyl azides is thermal rearrangement to a labile isocyanate (which can react with both aliphatic and aromatic amines to form ureas) for derivatizing alcohols and phenols.

Sulfonyl chlorides, including the dansyl, pyrene, Lissamine rhodamine B and Texas Red derivatives, are highly reactive. These reagents are quite unstable in water, especially at the higher pH required for reaction with aliphatic amines. Protein modification, for example, with this reagent is best done at low temperature. Once conjugated, however, the sulfonamides that are formed are extremely stable; they even survive complete protein hydrolysis (for example, dansyl end-group analysis. Sulfonyl chlorides can also react with phenols (including tyrosine), aliphatic alcohols (including polysaccharides), thiols (such as cysteine) and imidazoles (such as histidine), but these reactions are not common in proteins or in aqueous solution. Sulfonyl chloride conjugates of thiols and imidazoles are generally unstable, and conjugates of aliphatic alcohols are subject to nucleophilic displacement.

Aldehydes react with amines to form Schiff bases. Notable aldehyde-containing reagents described include o-phthaldialdehyde (OPA), naphthalenedicarboxaldehyde (NDA) and the 3-acylquinolinecarboxaldehyde (ATTO-TAG) reagents CBQCA and FQ. In addition, certain arylating reagents such as NBD chloride, NBD fluoride and dichlorotriazines react with both amines and thiols, forming bonds with amines that are particularly stable.

It is understood that any methods for conjugating a composition to a probe moiety will vary depending on, for example, the composition to be conjugated and the particular probe moiety that the chemical composition is conjugated to.

Use of Conjugates as Nucleic Acid Probes

Conjugates of the luminescent compositions and nucleic acids (e.g., hybridization probes) of the invention can be made from DNA, RNA, or some combination of the two. The probes can include modified nucleotides. The links between nucleosides in the probes may include bonds other than phosphodiester bonds.

In one embodiment, the luminescent hybridization probes are "molecular beacon"-type probes that are interactively labeled, hairpin forming oligonucleotides comprising a stem-and-loop structure. The loop contains a probe sequence complementary to the probe's target. Nucleotide sequences ("arms") flank the probe sequence and a sequence in one arm is complementary to a sequence in the other arm. When the probe is not hybridized to a target, the arms hybridize to one another and form a stem hybrid, which is sometimes referred to as a stem-duplex. This is the closed conformation. When the probe hybridizes to its target sequence, the longer and stronger probe-target hybrid overcomes the stem hybrid and separates the arm sequences. This is the open conformation. In the open conformation an arm can also hybridize to the target. For some molecular beacon probes, only perfectly complementary strands are targets that cause this change under assay conditions; for other embodiments the probe will open despite the presence of one or a few internal mismatches with the target. The molecular beacon probes described herein have a luminescent composition (e.g., any of the luminescent compositions of matter described herein) attached (e.g., covalently conjugated) to one arm and a quencher (for definition, see below) attached to the other arm. When the arms form the stem, the quencher is very close to the fluorophore/luminophore and effectively quenches or suppresses its fluorescence, rendering it dark.

As used herein, a "quencher" refers to a molecule or moiety that, when placed very close to an excited fluorophore, causes there to be very little or no fluorescence. Similarly a quencher when placed close to an excited luminophore causes there to be little or no luminescence emitted from the luminophore. Where the quencher moiety quenches both a fluorophore and a luminophore (e.g., a fluorophore and luminophore in a luminescence resonance energy transfer (LRET) relationship, see below), the quencher is a double quencher or "doubly quenches." Suitable quenchers described in the art include DABCYL and variants thereof, such as DABSYL, DABMI, Methyl Red, and BlackBerry® quenchers (available from Berry & Associates of Dexter, Mich.). Some fluorophores can also be quenchers, for examples, fluorophores that touch certain other fluorophores. Preferred quenchers are DABCYL, malachite green, or fluorophores that do not fluoresce in the detection range when the probe is in the open conformation.

As described above, hybridization of the loop to a target nucleotide can cause the oligonucleotide to assume its open confirmation. In certain embodiments, the quencher moiety is selected from the group consisting of BHQ, DABCYL, and variants of DABCYL. The single-stranded loop and one strand of the stem duplex can be complementary to the target strand, whereby the oligonucleotide is capable of serving as a primer for DNA polymerase. The oligonucleotide can also include a terminal extension capable of serving as a priming region for a DNA polymerase when the oligonucleotide is in its closed conformation.

The oligonucleotide sequences of molecular beacon probes modified according to this invention may be DNA, RNA, peptide nucleic acid (PNA) or combinations thereof. Modified nucleotides may be included, for example nitropyrrole-based nucleotides or 2'-O-methylribonucleotides. Modified linkages also may be included, for example phosphorothioates. Modified nucleotides and modified linkages may also be incorporated in wavelength-shifting primers according to this invention, subject, as will be recognized, to the requirement that one arm be able to serve a primer for a nucleic acid polymerase.

For probes according to this invention, the length of the loop sequence that is target complementary, the length of the stem hybrid and the relation of the two is designed according to the assay conditions for which the probe is to be utilized. Lengths of target-complement sequence and stem hybrid for particular assay conditions can be estimated by known means, tried and adjusted, if necessary. Typical probe sequences for use in PCR assays are in the range of 16 to 25 nucleotides. Typical stem lengths are in the range of 3 to 8, more commonly 4 to 7 nucleotides. The strength of the stem hybrid is adjusted by routine experimentation to achieve proper functioning. In addition to length, the strength of the stem hybrid can be adjusted by altering the G-C content and insertion of destabilizing mismatches, as will be appreciated. One arm can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, as well as being free-floating.

Hairpin-forming probes according to this invention may be utilized in detection assays. They may also be used as detectors in amplifications assays, and may be added prior to amplification, in which case quantitative results as to the initial concentration of amplifiable target may be obtained. Amplification reactions include the polymerase chain reaction (PCR), strand displacement amplification (SDA), nucleic acid sequence based amplification (NASBA), transcription mediated amplification (TMA), the ligase chain reaction (LCR), rolling circle amplification, and RNA-directed RNA amplification catalyzed by an enzyme such as Q-beta replicase. Multiple probes for multiple targets may be used in a single reaction tube or other container for multiplex assays.

Hairpin-forming primers are used in those of the amplification reactions identified above that include one or more primers. They may be modified according to the present invention to have an arm sequence that binds to a nucleic acid target, such that the hairpin-containing primer can be extended by incubation with a nucleic acid polymerase. The loop portion may, but need not be, complementary to the original target strand. Hairpin-containing primers have a stem labeled with a fluorophore on one arm and a quencher on the other arm, similarly to molecular beacon detection probes. Embodiments of the instant invention will be described primarily in connection with molecular beacon detection probes. Those of skill in the art will understand that the concepts and teachings apply to hairpin primers as well, and will understand how to apply the concepts and particular teachings to hairpin-containing primers.

Further description of uses for the luminescent compositions as part of molecular beacons and the like, including quenchers and additional fluorophores, can be found in, e.g., U.S. Pat. No. 6,037,130; U.S. patent application Ser. Nos. 08/439,619 and 08/990,176, which are incorporated herein by reference in their entirety.

Assays that utilize the nucleic acid probes (e.g., conjugates of any of the compositions herein with nucleic acid) of this invention begin simply by addition of the probes to the material of interest under conditions that are conducive to hybridization. The methods of processing the samples and monitoring the fluorescence signal may vary with the nature of the samples. Tissues may be disrupted mechanically or by incubation with chaotropic salts. Most disrupted tissues may be used directly in the assays. Some tissues, however, contain naturally fluorescent materials that may interfere with the detection of signal. In such cases, the nucleic acids may be isolated from the fluorescent materials either before or after hybridization. The fluorescence of opened probes can be monitored by fluorometers. The luminescence of opened probes can be monitored by luminometer.

The conjugates of the composition and nucleic acids (e.g., DNA, e.g., probes) described herein are useful, for example, in field tests for certain infectious diseases. For example, a test for malaria or HIV-I may begin by addition of guanidine thiocyanate to a sample of blood to lyse the cells, detoxify the cells and denature the constituents. A large excess of a probe (relative to the expected maximal target concentration) which is complementary to, for example, a ribosomal RNA of the malarial parasite may then be added, and hybridization allowed to proceed. Luminescence or fluorescence of open probes may be monitored either visually or with help of a luminometer or fluorometer. Detection of a positive luminescent and/or fluorescent signal indicates an infection by the malarial parasite or HIV-I virus. Any of the probes described herein can be used to locate particular nucleic acid fragments in a gel or other medium, for example where information on the size of a specific nucleic acid is desired. The nucleic acids in the sample can first be fractionated by gel electrophoresis and then the gel itself bathed in a solution containing the probes. The location in the gel where the target nucleic acid migrates will be detectable by the characteristic signal as a result of hybridization. Production of nucleic acids in synthesis reactions may be monitored by including appropriately designed probes in the reaction mixture and monitoring the level of signal, e.g., luminescence, in real-time. The probes should be designed to be complementary to a segment of the nucleic acid that is produced. Examples of such reactions are RNA synthesis by DNA-dependent RNA polymerases and by Q-beta replicase. Unimolecular probes are particularly useful in tracking a polymerase chain reaction, since they open and close with a speed faster than the speed of thermal cycles used in this reaction. An additional temperature in each cycle, which is 5-12EC lower than the melting temperature of the stem of the probe, may be included as the detection temperature. In each cycle, the level of luminescence will indicate the amount of target DNA strand present. An excess of the probes, as an excess of PCR primers, in the reaction mixture should be used. The PCR may be asymmetric. Real-time monitoring of the correct products, as opposed to end-point detection, improves the precision and the dynamic range of the estimates of the target nucleic acid concentrations by polymerase chain reactions and obviates the need for post-amplification analysis.

In some embodiments, the hybridization analysis is related to methods of using luminescently labeled DNA/RNA hybridization probes that do not have a quencher and steam-loop structure, and simply hybridize to a complementary nucleic acid target. In some embodiments, an excess of hybridization probe is used. These probes are especially useful in the FISH method whereby after the binding the excess of the hybridization probe is removed by washing.

In some embodiments, the use of nucleic acid based detection probes takes advantage of aptamers nucleic acid sequences having high affinity to a wide variety of materials of biological origin as well as those obtained artificially. In principle, an aptamer can have a predetermined binding affinity for any target (e.g., molecule or supramolecular structure) of interest including proteins, polysaccharides, small molecules and their complexes. Generation of aptamers in achieved through Systematic Evolution of Ligands by Exponential Enrichment (SELEX) in which a random synthetic oligonucleotide pool is incubated with a target. Binding sequences are separated from the rest of nucleotide material, eluted and PCR amplified. The enriched pool is incubated again with the target. After several repetitive cycles the high affinity aptamers are cloned and sequenced. While having a specificity comparable to antibodies, aptamers can be easily synthesized in an automated mode and easily derivatized with labels, reporter groups, or affinity tags. Aptamers can be used in the same applications as antibodies.

The luminescent probes described herein can also be used for monitoring other nucleic acid amplification reactions, such as strand displacement amplification reactions and self-sustained sequence replication reactions. Useful probes are designed and used in a manner similar to the probes for polymerase chain reaction products.

Additional embodiments and examples of the use of such probes are described in U.S. Application Publication Ser. Nos. 08/152,006; 60/161,096; and 10/426,556, and U.S. Pat. Nos. 5,925,517; 6,150,097; 6,461,817; and 6,037,130, which are hereby incorporated by reference in their entirety.

Luminescence Resonance Energy Transfer and Assays

Any of the compositions or their conjugates can use, for example, Luminescence Resonance Energy Transfer (LRET) as a mechanism of signal generation. FRET can be used to measure the distances between two points that are labeled with fluorescent dyes and separated by approximately 10-75 angstroms. The technique is valuable because measurements can be made under physiological (or other) conditions with near-Angstrom resolution and with the exquisite sensitivity of fluorescence measurements. FRET relies on a distant-dependent transfer of energy from one fluorescent dye—the donor—to another absorbing or fluorescent dye—the acceptor. The donor and acceptor are site-specifically placed at the two points that one wishes to measure the distance between.

While lanthanides do not fluoresce, the use of any of the luminescent compositions (or conjugates thereof) described herein permits them to be efficiently excited. A non-fluorescent quantum transition of the lanthanide can then effect a non-radiative energy transfer to a suitable and appropriately distanced acceptor. To effect transfer, an acceptor absorption must overlap a lanthanide emission. The chelate-acceptor pair is selected for optimal overlap: for longer distance measurements, greater overlap is preferred. Since the lanthanides have lifetimes on the order of a millisecond, the signal-to-noise ratio of sensitized emission of the acceptor in LRET is improved by emission detection through time resolution (pulse delay) or phase modulation. Energy transfer can be detected by donor quenching or, preferably acceptor luminescence.

By using luminescent lanthanide chelators as donors (instead of conventional dyes), and conventional fluorescent dyes as acceptors, we have improved the signal to background of LRET by approximately 100-fold. This improvement allows measurements beyond 100 angstroms, a distance currently unmeasurable using small, conventional fluorescent dyes. This distance regime is important in many biological problems. Using lanthanide chelators as donors also makes distance measurements more accurate, because the chelators minimize the uncertainty in the orientation-dependence of energy transfer.

LRET is particularly useful to obtain structural and kinetic information about macromolecules in solution, in real time. For example, double-end labeled oligonucleotides provide detectable LRET signaling when bound by nucleic acid binding proteins, e.g., transcription factors. Accordingly, the methods are used to screen for potential therapeutics that alter the structure or interactions of biomolecules; for example, anti-viral agents are screened for the ability to alter vital transcription factor-induced alterations in nucleic acid conformation.

The general LRET-based method of detecting the distance between a first position and a second position in a portion of a sample involves: exposing a sample portion comprising the donor lanthanide-chelate complex located at the first position and the acceptor located at the second position to light at a first wavelength capable of inducing a first electronic transition in the donor. The spectral overlap of the donor emission and acceptor absorption is sufficient to enable energy transfer from the donor to the acceptor as measured by detectable quenching of donor luminescence intensity or lifetime or detectable increase in acceptor luminescence intensity or lifetime. Then the intensity of a first emission of light from the sample portion at a second wavelength is detected wherein the second wavelength is longer than the first wavelength and results from a second electronic transition in the donor, wherein the intensity of the first emission of light correlates with the distance between the first and second positions. In other words, the closer the positions, the greater the energy transfer and the greater the donor quenching. Alternatively, one can detect the intensity of a second emission of light from sample portion at a third wavelength, wherein the third wavelength is longer than the first wavelength and results from an electronic transition in the acceptor, wherein the intensity of the second emission of light inversely correlates with the distance between the first and second positions of the sample portion. In other words, the closer the positions, the greater the energy transfer and the greater the acceptor luminescence.

This general method has broad application whenever the static or dynamic distance between to positions, e.g., two atoms or molecules, is of interest. In one specific embodiment, the method is used to monitor the status of a polymerase chain reaction. Here, the sample portion comprises a target nucleic acid strand comprising a first strand portion and a diagnostic nucleic acid strand labeled proximal to one end with the acceptor and proximal to the other end with the donor (i.e., comprising a first atom covalently joined to the donor and a second atom covalently joined to the acceptor, the first and second atoms being separated by a second strand portion). The first and second strand portions are sufficiently complementary to hybridize under annealing conditions, and the second strand portion is of sufficient length to provide a detectable difference in the aggregate energy transfer from the donor to the acceptor when the first and second strand portions are hybridized as compared with the aggregate energy transfer from the donor to the acceptor when the first and second strand portions are not hybridized. The detectable difference is measured as at least one of a detectable quenching of donor luminescence or detectable increase in acceptor luminescence, and the distance between the first and second atoms indicates whether the nucleic acid strands have hybridized. Thus, as the reaction proceeds, the stepwise increase in the mount of target nucleic acid is reflected in a stepwise decrease in energy transfer.

Detection or imaging methods using LRET or FRET are useful for such varied applications as detection of epitope mapping, peptides association in membranes, lipid order in vesicles, membrane organization, lipid distribution, protein folding kinetics, transport systems, in vivo protein-protein interactions, protein subunit exchanges, DNA-protein interactions, tRNA-ribosomes, DNA triple helixes, and nucleic acid hybridization.

In general, the compositions and conjugates thereof described herein can be used to detect and/or quantify a target material of interest containing, or derivatized to contain, a target sequence. The target-sequence-containing target material is incubated with luminescent conjugates described herein for a time period sufficient to allow binding to and/or labeling of the target material. FRET from the conjugate is detected, thereby detecting the target material. The target material can be detected in any material, including, but not limited to, cuvettes, microtiter plates, capillaries, flow cells, test tubes, gels, blots, and biological samples. In some embodiments, the target material can be detected in the body of a subject. A FRET assay can also be used to monitor a reaction between analytes. For example, a kinase assay. Such methods are described in, for example, Von Ahsen et al. (2006) J. Biomol. Screen; Green et al. (2005) BMC Chem. Biol. 5:1; and Zhang et al. (2005) Anal Biochem. 343(10): 76-83.

The reaction can also be, for example, a protein folding event, a cleavage event, a protein self-association event, or rates thereof. The method can be an immunoassay, a DNA-protein binding assay, a protein-protein assay, a protein conformational assay, and rate studies thereof, many of which are described above.

Additional description of LRET and FRET and methods of use can be found in, for example, U.S. Pat. No. 5,622,821; and Selvin et al. (2002) Ann. Rev. Biophys. Biomol. Structure 31:275-302, both of which are incorporated herein by reference in their entirety.

Application of the Lanthanide-Based Probes for Tracing Analysis

The present invention also provides for a method for detecting an analyte in a sample including the steps of contacting a sample containing the analyte with a luminescent chelate composition to specifically bind the anlayte to form a luminescent-analyte complex, illuminating the sample with excitation radiation, and detecting emission radiation of at least one luminescent-analyte complex, wherein the luminescent chelate composition is any fluorophore and chelating moiety described herein.

In some embodiments, the composition of matter can contain a chelating moiety including, but not limited to, EDTA, DTPA, TTHA, DOTA, TAGA, DOTP, DTPA-BMA, DO2P, and HP-DO3A. In certain embodiments, the $R_2$, $R_3$, or $R_4$, and $R_5$, $R_6$, or $R_7$ cite of the fluorophore can further contain a cross-linking group selected from the group consisting of isothiocyanate, haloacetate, haloacetamide, nitrogen mustard, epoxide, maleimide, disulfide, activated ester, imidate, or acetylenic derivative.

In some embodiments, the luminescent-analyte complex is formed by physical mixing of the luminescent chelate composition and analyte in the sample. In other embodiments, the luminescent-analyte complex is formed by chemical cross-linking of the luminescent chelate composition with the composition.

In certain embodiments, the analyte is contacted with a first luminescent chelate composition and a second luminescent chelate composition, wherein the first luminescent chelate composition comprises a first lanthanide and the second luminescent chelate composition comprises a second lanthanide, wherein the first and second lanthanides are different.

In other embodiments, the analyte is contacted with a first luminescent chelate composition and a second luminescent chelate composition, wherein the first and second luminescent chelate compositions have the same emission spectra, but different emission lifetime.

In some embodiments, the $R_1$ chelating moieties of the first and second luminescent chelate compositions independently comprise at least one modifier selected from the group consisting of hydrazine, diamine, tetraamine, and cyclic tetraamine.

In other embodiments, the analyte is contacted with a first luminescent chelate composition and a second luminescent chelate composition, wherein the first and second luminescent chelate compositions can be selectively excited at different wavelengths.

In one aspect the present invention provides a method for non-invasive determination of the composition of multicomponent mixtures, not limited to optically transparent materials, employing sensitive luminescent lanthanide and ruthenium ion based tracers based on the spectral features of the lanthanide and ruthenium luminescence as well as on the temporal behavior of the luminescent signals. In some embodiments, ultra-high sensitivity is obtained by time gating of the signal as well as by the high luminescence quantum yield. In certain embodiments, the tracers, in very small amounts, are added to the components of the mixture before mixing of the components. This can be done either by physical mixing of the tracers with the components, or by chemical cross-linking of the tracer probes with the individual components. The mixture composition is then determined by measuring the luminescence of the mixture using proper optical instrumentation.

There are a variety of instrumentation configurations that employ the general approach, described above. In one embodiment of the present invention, light from a pulsed light source either of laser or conventional nature (such as flash lamps, chopped continues light beam, etc.), is directed on the material to be analyzed. The luminescence of the material (ether surface or bulk) is collected and spectrally and temporally analyzed. This is achieved using gaited ICCD or other CCD cameras, by gated photomultipliers or photodiodes, or their arrays, or even by mechanical means (shutters, choppers, etc.). As a result, a set of time-resolved spectra is acquired. The spectra are deconvoluted according to the spectra of individual lanthanides as well as their luminescence lifetimes. Accordingly, another aspect of the present invention provides a quantitative real-time highly sensitive analysis of the material of interest, non-invasive and remote, if required.

The detection methods described herein rely on spectral and temporal analysis of the cumulative luminescent signal of the analyte coming from the mixture of tracers. In some embodiments, the tracers include, but are not limited, lanthanide-based probes (shown in FIG. 4) in which the light absorbed by antenna is first transferred to coordinated lanthanide that emits the light (FIG. 1). Lanthanide emission is long lived, which allows elimination of short lived background fluorescence using time-delayed signal acquisition.

In certain embodiments, the tracing analysis includes tracers with various emission spectra. In some embodiments, such analysis includes the use of various lanthanides in the context of the same antenna-fluorophore.

Figure 2:
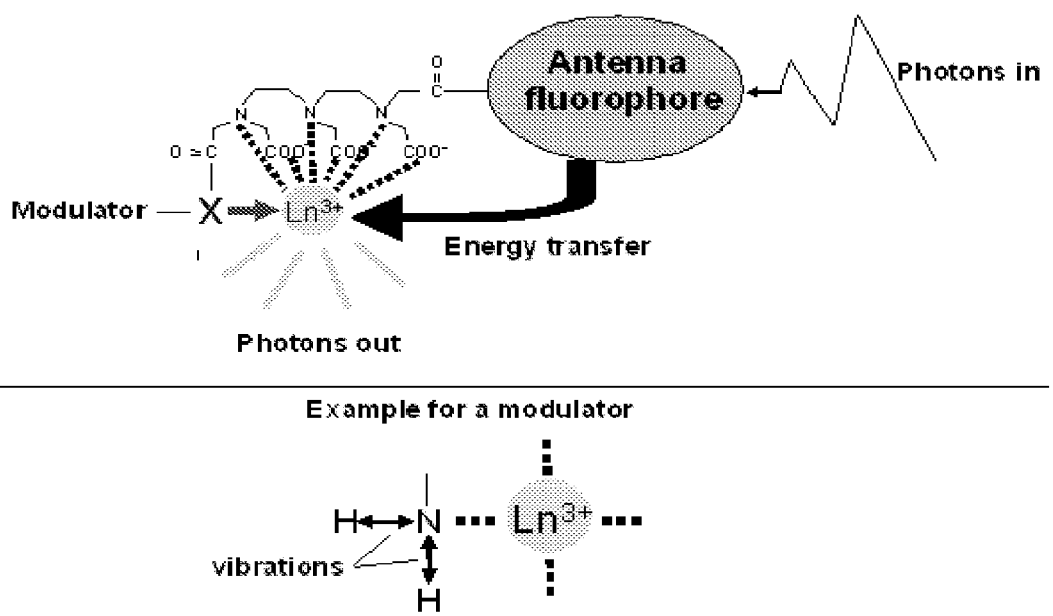
FIG. 2 is a schematic description of a design of luminescent probes with tunable life time.

In other embodiments, the tracing analysis includes tracers with the same emission spectra, but having different emission lifetime. In certain embodiments, the signal lifetime of the luminescent probe is tuned, as depicted in FIG. 2. Without wishing to be bound by theory, it is believed that specially designed groups (modulators) can effect the luminescence life time by coordinating to lanthanide. In certain embodiments, chelating groups containing N—H or O—H bonds can reduce the life time through a vibrational mechanism. In other embodiments, ligands containing various numbers of such groups can be attached to generate a set of compounds with broad range of signal lifetime. The structure of some of the suggested compounds is shown in Table 2.

In certain embodiments, the chelator group includes triethylenetetraminehexaacetic (TTHA) derivative (structure A), that saturates all nine coordination valences of lanthanide ion, leaving no room for water or other chelating molecules of the surrounding medium that can be coordinated by lanthanide. These embodiments beneficially minimize the influence of media effect on lanthanide lifetime. In certain embodiments, attached TTHA residues can be further modified by hydrazine, or diamine (structures B and C correspondingly) to introduce chelating groups containing adjacent hydrogens that are expected to shorten the lifetime of the coordinated lanthanide. The number of chelating groups in these structures is also nine. In another embodiments, diethylenetriaminepentaacetate (DTPA)-containing chelators can be used (structures D and E). In this subset of structures, the number of chelating groups is nine as well. In structures A-E, the number of hydrogen-containing chelating groups gradually increases from 0 to 3, which is expected to change the lanthanide lifetime in a broad range.

In certain embodiments, all of the chelating groups described herein can be used with various lanthanides (Tb, Eu, Dy, Sm) in the context of different antennae-sensitizers, examples of which are given in Table 2 (right).

TABLE 2

Structures of suggested lanthanide-based probes with variable lifetime

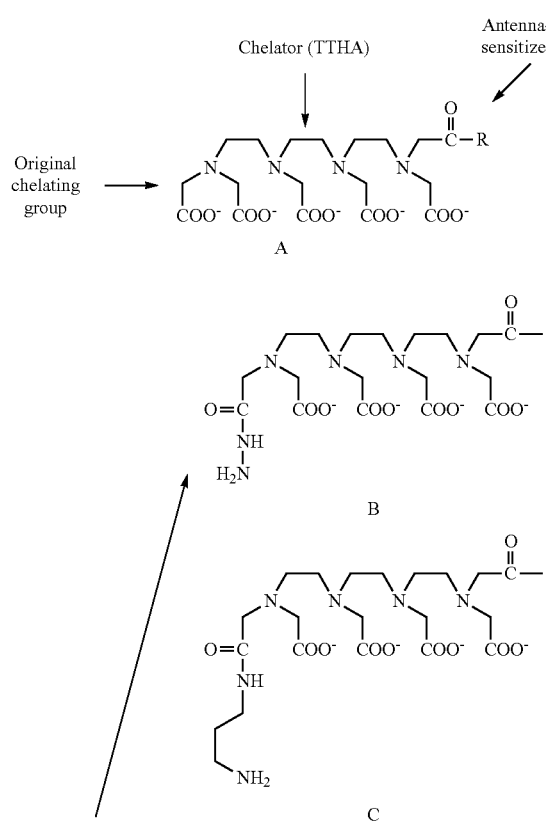

TABLE 2-continued

Structures of suggested lanthanide-based probes with variable lifetime

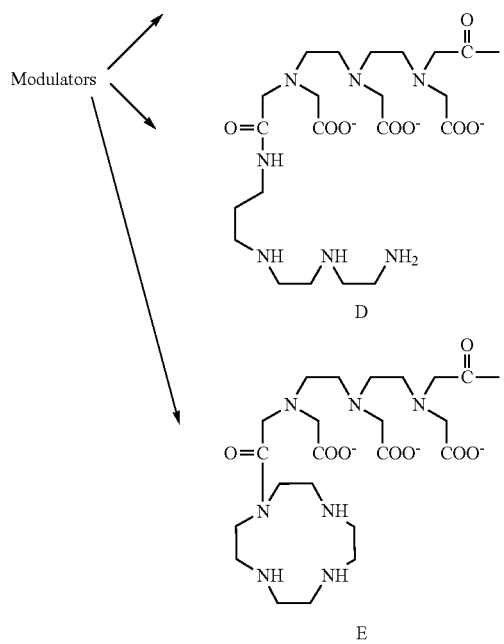

D

E

R =
Examples of known sensitizers

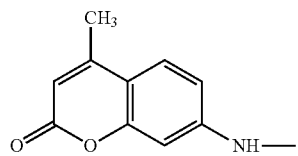
I

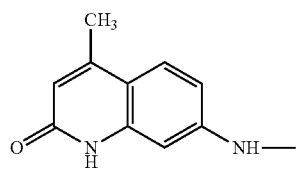
II

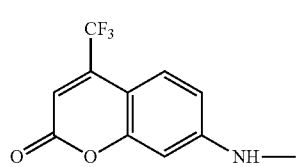
III

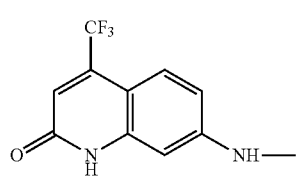
IV

TABLE 2-continued

Structures of suggested lanthanide-based probes with variable lifetime

Suggested sensitizers

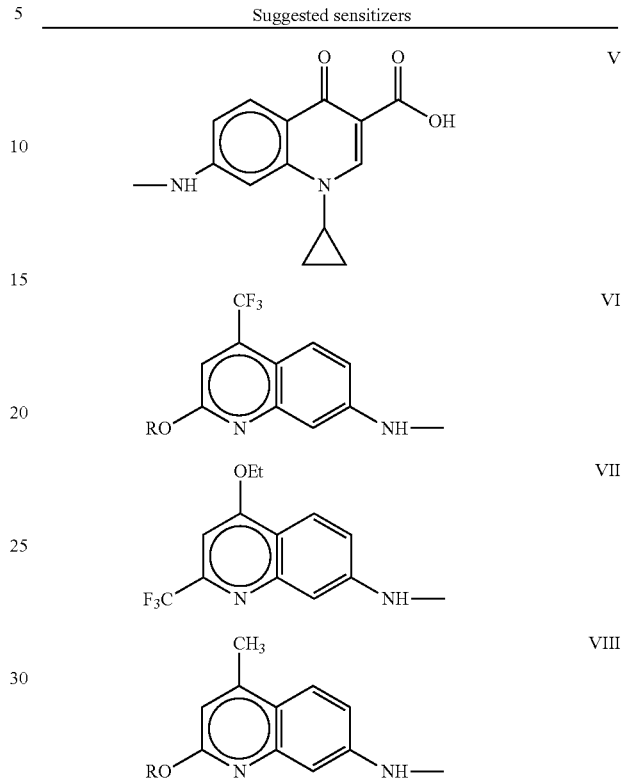

In certain embodiments, this generates a variety of luminescent probes with desired spectral and temporal properties suitable for multi-component mixture analysis.

Figure 3:
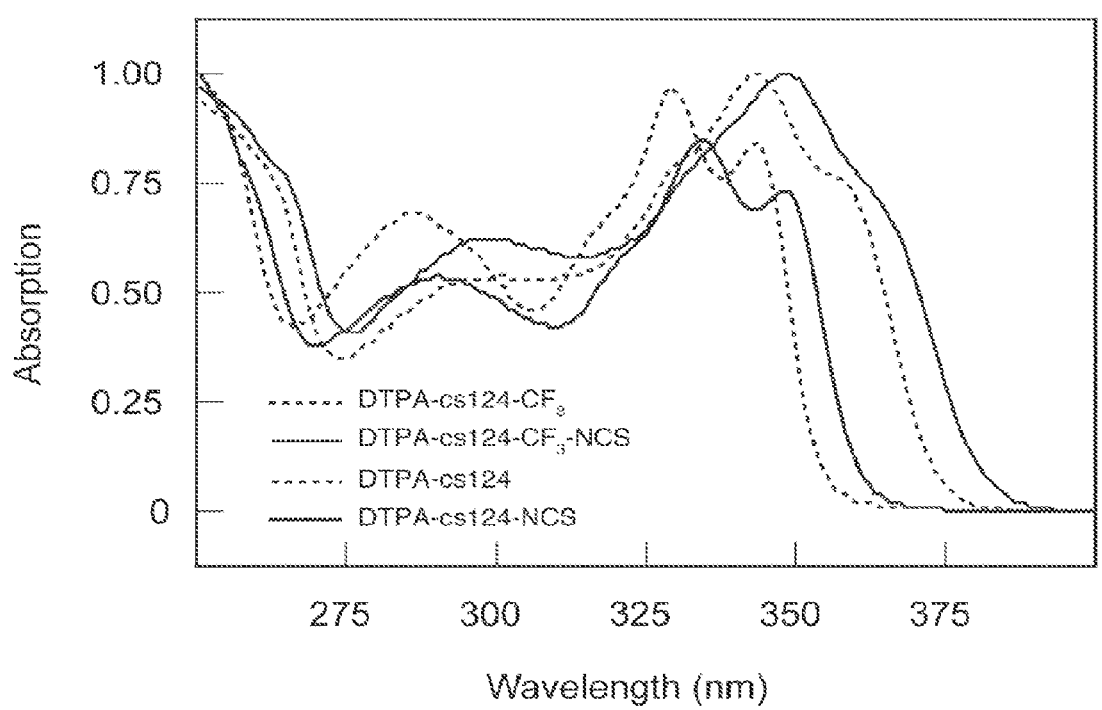
FIG. 3 demonstrates absorption spectra of representative fluorophores of the invention.

In some embodiments, an increase in the spectral discrimination of the used probes is obtained with the use of antenna fluorophores that can be selectively excited at different wavelengths. FIG. 3 shows absorption spectra of representative fluorophores. The spectral difference allows selective excitation of some fluorophores in the presence of others by using different light sources in the range 350-380 nm.

Figure 4:
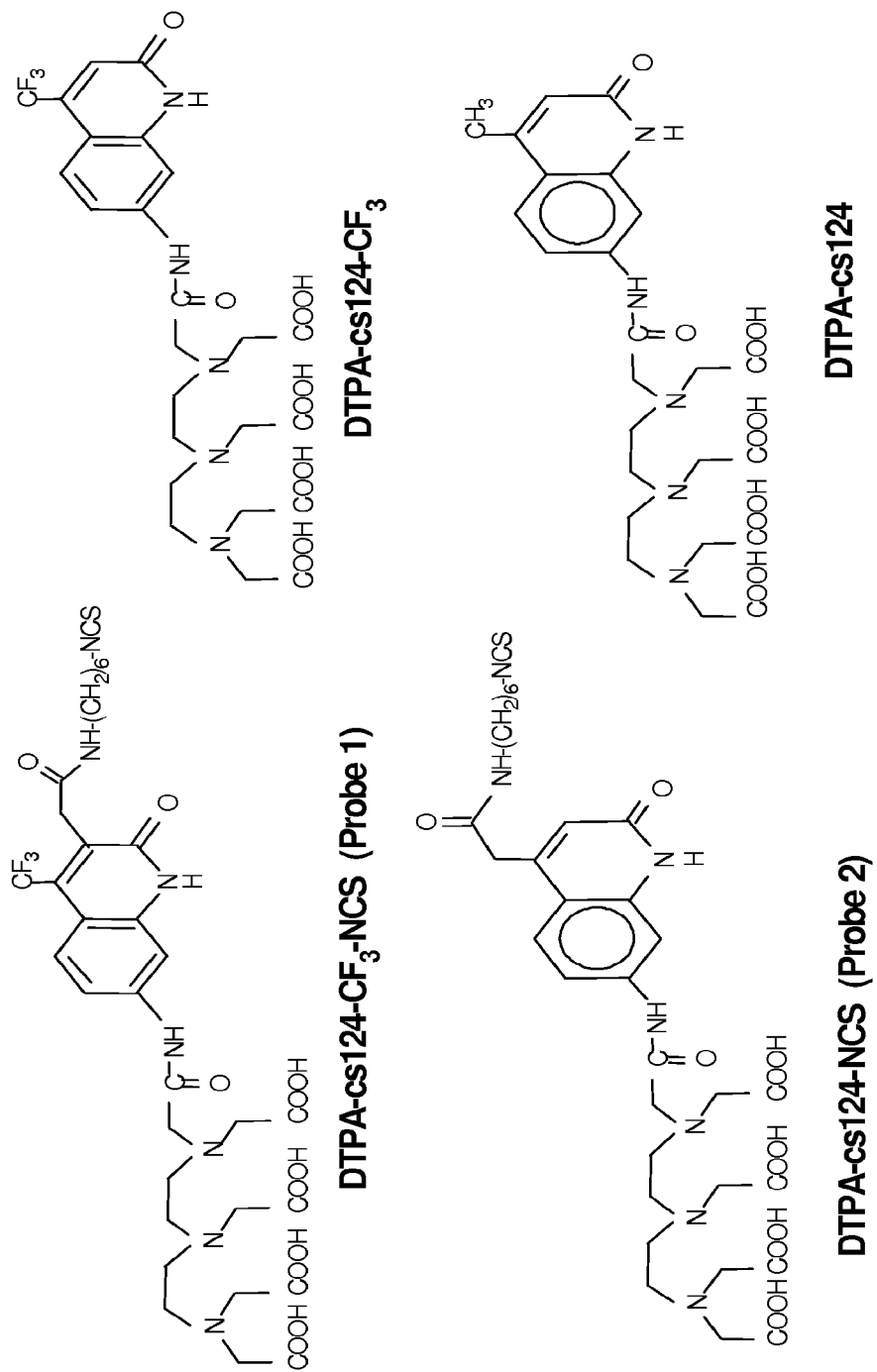
FIG. 4 demonstrates the structures of representative compounds of the present invention.

The structures of these compounds are presented in FIG. 4.

Figure 5:
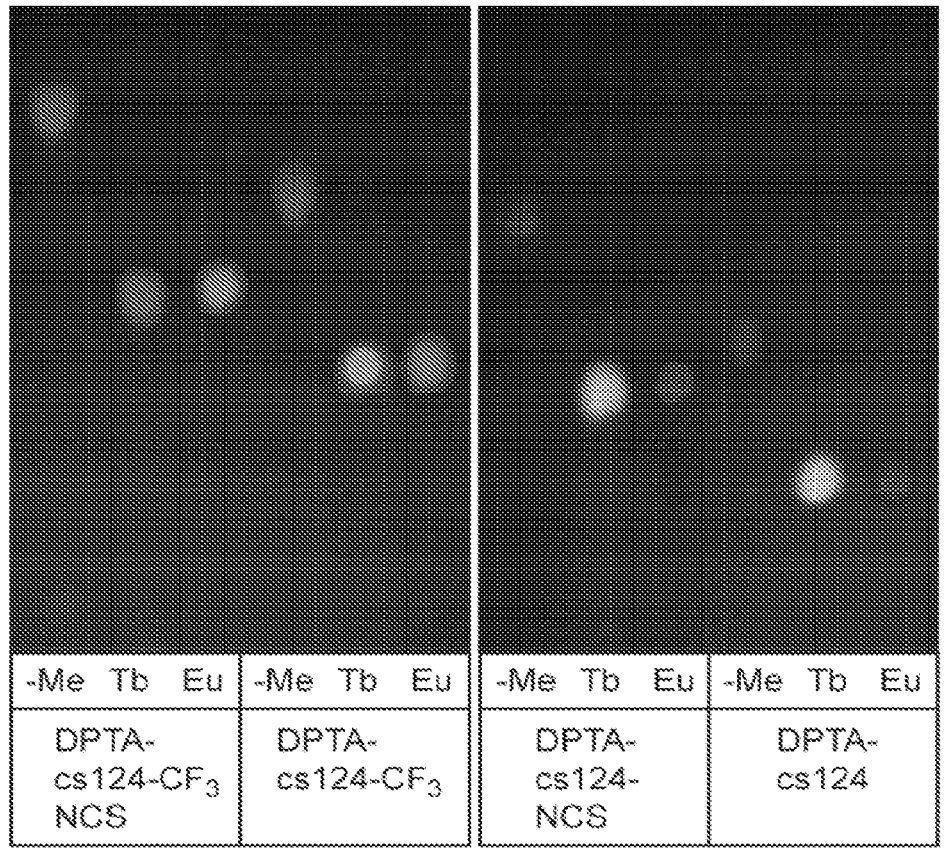
FIG. 5 demonstrates an example of a TLC separation of the present invention.

In some embodiments, the fluorophores can be added by modification of the structure that preserves the optical properties, but changes their physical properties (e.g., chromatographic mobility) through chemical modification (which includes, but is not limited to, covalent, ionic, and hydrogen bonds, electrostatic interactions, coordination interactions, or donor-acceptor interactions). In certain embodiments, various lanthanide compounds can be easily separated by chromatography. An example of fast efficient thin-layer chromatography (TLC) separation (FIG. 5) is shown for some compounds. These compounds can be easily modified (e.g., by introduction of different substitutions in position 3, 2, or 1 of the quinolone ring) to generate a variety of new tracers.

In certain embodiments, analysis of such TLC images in both spectral and temporal modes enables deconvolution of a much larger number of tracers and analysis of highly complex mixtures.

The following examples are meant to illustrate, not limit, the scope of the invention.

EXAMPLES

Example 1

Synthesis

The following reagents were purchased from Aldrich: diethylenetriaminepentaacetic acid dianhydride (DTPA), triethylamine, 1,3-phenylenediamine, ethyl 4,4,4-trifluoroacetoacetate, ethylacetoacetate, 1,3-dicyclohexylcarbodiimide (DCC), ethylenedianime, N-trityl-1,4-diaminobutane, N-trityl-1,6-diaminobutane, triphenylmethylchloride, methylbromacetate, anhydrous dimethylformamide and dimethylsulfoxide, 1-butanol ethylacetate, chloroform, acetonitrile, ethanol, sodium and potassium hydroxide, $ZnCl_2$, $Na_2SO_4$, $Na_2CO_3$, acetic acid, citric acid, thiocarbonyldiimadazole, $TbCl_3$ and $EuCl_3$, silica gel TLC plates on aluminum foil (200 μm layer thick with a fluorescent indicator). Only distilled and deionized water (18 $M\Omega cm^{-1}$) were used. All experiments, including the preparation and use of lanthanide complexes, were performed either in glassware washed with mixed acid solution and rinsed with metal-free water, or in metal-free plasticware purchased from Bio-Rad. All chemicals were the purest grade available.

Probe 1 (Scheme 1A)

1. 7-amino-4-trifluoromethyl-3-carbomethoxymethyl-2(1H) quinolone (II) ($cs124CF_3$—$CH_2COOCH_3$)

4,4,4-Trifluoroacetoacetate (2.2 ml, 15 mmol) and KOH (0.86 g, 15 mmol) were mixed in 7 ml of dimethylformamide and stirred at 40° C. until dissolved. To this mixture, 1.5 ml of methylbromoacetate was added and the solution was incubated overnight at room temperature. Three hundred milligrams (5.2 mmol) of KOH was then added, and incubation continued at 60° C. for 1 h. This mixture was diluted by the addition of 20 ml of water and was then extracted with chloroform. The organic layer was collected, dried over anhydrous sodium sulfate, and then evaporated in vacuo, first at 30° C., and then at 70° C. for 30 min. The residue (1.9 g, product I) was dissolved in 3.5 ml of DMSO, and then 0.76 g (7 mmol) of 1,3-phenylenediamine was added, followed by incubation at 110° C. for 6 h. Under these conditions, four fluorescent products were detected by thin layer chromatography in ethylacetate as developing solvent: Rf=0.90 (green-blue fluorescence); Rf=0.45 (blue fluorescence); Rf=0.30 (blue fluorescence), and Rf=0.03 (green-blue fluorescence). This mixture was diluted with 30 ml of 0.05 M aqueous NaOH and extracted with ether (2×40 ml). The aqueous layer was separated and treated as described below (Section 2). The organic layer was extracted with 1 volume 0.1 M citric acid, and then collected, dried over anhydrous sodium sulfate, and evaporated in vacuo. The residue was subjected to silica gel chromatography on a 40 ml column, using a hexane: acetone mixture (3:1) as eluent. Fractions corresponding to the products migrating with Rf=0.45 (product II) were collected and evaporated to dryness. The residue was then washed with chloroform and dried. Yield~130 mg. UV: $\lambda_{max}$=365 nm ($\epsilon$=14,300 $M^{-1} cm^{-1}$), $\lambda_{min}$=295 nm ($\epsilon$=2,800 $M^{-1} cm^{-1}$). $^1$H NMR chemical shifts (d) in DMF were: 3.65 (3H, methyl), 3.94 (q, 2H, 3-methylene, J=3.6), 6.24 (broad, 7 amine), 6.72 (m, 1H, 6H), 6.72 (m, 1H, 8H), 7.48 (1H, 5H), and 11.9 (broad, amide).

2. 7-amino-4-trifluoromethyl-3-carboxy-2(1H) quinolone (III) ($cs124CF_3$—$CH_2COOH$)

One ml of 1 M aqueous NaOH was added to 100 mg of product II dissolved in 2 ml dioxane. After 4 h incubation at 50° C., the mixture was diluted by the addition of 15 ml water and extracted with ether. The product (III) was precipitated from the aqueous phase by the addition of citric acid to pH 3-3.5, collected by centrifugation, washed a few times with water until neutral reaction, and dried in vacuo. Yield~70 mg.

The aqueous phase obtained after ether extraction (see previous section), containing product III, was acidified by the addition of citric acid to pH 3-3.5; the precipitate was collected, washed a few times with water, dried, and then combined with the above. Re-crystallization from ethylacetate resulted in the isolation of pure product III (total yield~200 mg). $^1$H NMR chemical shifts (d) in DMF were: 3.93 (2H, 4 methylene), 6.19 (2H broad, 7 amine), 6.71 (1H, 6H), 6.71 (1H, 8H), 7.48 (1H, 5H), 11.85 (broad, amide), and 12.75 (broad, carboxyl).

3. $cs124CF_3$—$CH_2C(O)$—$NH(CH_2)_6NH$-Tr (IV)

One hundred milligrams (~0.3 mmol) of product III were dissolved in 8 ml of THF and supplemented with 210 mg (1 mmol) of DCC. After one hour incubation, thin layer chromatographic analysis in ethylacetate:ethanol (10:1) revealed a single product (Rf=0.80) with intense blue fluorescence. Four hundred fifty micromoles of N-trityl-1,6-diaminobutane were added and incubation continued for another 30 min at 20° C. Thin layer chromatography in ethylacetate:ethanol (10:1) revealed the main reaction product ($R_f$=0.70). This mixture was diluted with 20 ml of 0.1 M aqueous $Na_2CO_3$ and extracted with an equal volume of chloroform. The organic phase was then collected and rinsed with 1 volume 0.2 M citric acid, dried over anhydrous sodium sulfate, and the solvent was removed by evaporation under reduced pressure. The product was purified by silica gel chromatography, using ethylacetate:ethanol (10:1) mixture as eluent. Yield ~160 mg. $^1$H NMR chemical shifts (d) in DMF were: 1.45 (m, 8H), 1.65 (m, 2H), 1.78 (m, 2H), 2.03 (q, 2H, J=7.25), 2.41 (t, 1H, J=7.2), 3.08 (q, 2H, J=7.2), 3.82 (q, 2H, 4-CH2-, J=4.0), 6.14 (s, 2H, broad, 7 amine), 6.7 (1H, 8H), 6.7 (1H, 6H), 7.18 (t, 3H, p-ArH, J=7.2), 7.30 (t, 6H, m-ArH, J=7.4), 7.48 (d, 6H, o-ArH, J=7.4), 7.48 (1H, 5H), and 11.75 (1H, broad, amide).

4. $cs124CF_3$—$CH_2C(O)$—$NH(CH_2)_6N$=$C$=$S$ (V)

One hundred forty milligrams of compound IV were dissolved in 2 ml of 90% acetic acid and incubated at 90° C. for 15 min. After evaporation in vacuo, the resulting residue was suspended in water and extracted with ether to remove triphenylcarbinol. The aqueous phase was then evaporated to dryness. The resulting residue was dissolved in 2 ml of methanol, and 80 mg of thiocarbonyldiimadazole were then slowly added to this solution under rigorous agitation. After 10 min incubation at room temperature, the mixture was supplemented with 100 μl of trifluoroacetic acid and kept at 50° C. Thin layer chromatographic analysis in ethylacetate:ethanol (12:1) revealed near quantitative conversion of the original compound (Rf=0.05) to an isothiocyanate (Rf=0.40). This product was purified by column chromatography using the same eluent. Yield~60 mg. $^1$H NMR chemical shifts (d) in DMF were: 1.35 (m, 4H), 1.46 (m, 2H), 1.65 (m, 2H), 3.13 (m, 2H, J=7.25), 3.69 (t, 1H, J=7.2), 3.08 (q, 2H, J=7.2), 3.82 (q, 2H, 3CH2-, J=3.7), 6.14 (s, 2H, broad, 7 amine), 6.7 (1H, 8H), 6.7 (1H, 6H), 7.48 (m, 1H, 5H), 7.76 (t, 1H, J=5.5), and 11.77 (1H, broad, amide).

5. Lanthanide Complexes of DTPA-cs124-$CF_3$—NCS (Probe 1)

Thirty milligrams (0.1 mmol) of compound V were added to a solution of 80 mg (0.3 mmol) of DTPA dianhydride in 0.8 ml of DMSO. After incubation (45 min at 50° C.), the mixture was supplemented with 10 ml of ether, and the resulting precipitate was spun down, washed with ether, air dried, dissolved in 1 ml of DMF, and mixed with 0.3 ml of water. After incubation for 10 min at 45° C., the mixture was diluted with 5 ml of water and extracted with 40 ml of butanol. The organic phase was separated and divided into four equal parts.

Each portion was mixed with 0.3 ml of a 0.1 M solution of a lanthanide trichloride ($Tb^{3+}$, europium ($Eu^{3+}$), dysprosium ($Dy^{3+}$), and samarium ($Sm^{3+}$)). After vigorous agitation, the organic phase was collected and concentrated by co-evaporation with water in vacuo at 30° C. Analytical thin layer chromatography, using an acetonitrile:water system (3:1) as the developing solvent, revealed two main $Ln^{3+}$ products (Rf=0.25 and 0.50). The products with Rf=0.50 (desired compound) were purified using preparative thin layer chromatography under the same conditions. The fluorescent material was eluted with 50% aqueous ethanol, and was recovered as a colorless powder after evaporation in vacuo. UV:$\lambda_{max}$=347 nm ($\epsilon$=14,800 $M^{-1}$ $cm^{-1}$), $\lambda_{min}$270 nm ($\epsilon$=4,700 $M^{-1}$ $cm^{-1}$). MS: $Eu^{3+}$DTPA-cs124-$CF_3$—$CH_2C(O)$—$NH(CH_2)_6N$=C=S (—$H^+$) 950.1 (found), 950.0 (calculated). $Ln^{3+}$ complexes of DTPA-cs124-$CF_3$ were obtained using the same protocol.

Probe 2 (Scheme 1B)

1. 7-amino-4-carboethoxymethyl-2(1H) quinolone (VII)

A suspension of 1.36 g (10 mmol) of $ZnCl_2$ in 5 ml of DMSO was supplemented with 1.08 g (10 mmol) of 1,3-phelylenediamine and 2.02 g (10 mmol) of diethyl-1,3-acetonedicarboxylate. The mixture was kept at 95 to 100° C. for 24 h. Thin layer chromatography in chloroform:ethanol (10:1) isolated one main fluorescent product (Rf=0.35). This mixture was diluted with 8 ml of ethanol, poured into 150 ml of ice-cold 0.1 M citric acid, and left for 3 h at 4° C. The residue was filtered and successively washed with water (2×10 ml), and with hot acetonitrile (2×5 ml), and then dried in vacuo. Yield~1.4 g (60%). $^1$H NMR chemical shifts (d) in DMSO were: 1.17 (t, 3H, —$OCH_2CH_3$, J=7.2), 3.76 (s, 2H, 3-methylene), 4.06 (q, 2H, —$OCH_2CH_3$, J=7.2), 5.81 (2H, broad, 7 amino), 6.01 (s, 1H, 3H), 6.37 (d, 1H, 8H, J=2.4), 6.43 (dd, 1H, 6H, J=7.2, J2=2.4), 7.25 (d, 1H, 5H, J=7.2), and 11.28 (1H, broad, amide).

2. 7-amino-4-carboxamido(6-aminohexyl)methyl-2(1H) quinolone (VIII)

Pre-melted 1,6-diaminohexane (2 g, 17 mmol) was mixed with 7-amino-4-carboethoxymethyl-2(1H) quinolone (0.5 g, 2 mmol). After incubation (15 h, 90° C.), the mixture was poured into 30 ml of water. The precipitate was washed with water (3×30 ml), and ethylacetate (3×20 ml), and then stirred with hot methanol (50 ml), filtered, and the filtrate was evaporated to dryness in vacuo. The product appeared as light-brown crystals. Yield~0.5 g. $^1$H NMR chemical shifts (d) in DMSO were: 1.2-1.4 (m, 10H), 3.04 (q, 2H, α-$CH_2$, J=7.2), 3.49 (s, 2H, 4-methylene), 5.75 (2H, broad, 7 amino), 5.98 (s, 1H, 3H), 6.36 (d, 1H, 8H, J=2.4), 6.43 (dd, 1H, 6H, J1=7.2, J2=2.4), 7.38 (d, 1H, 5H, J=7.2), 8.07 (t, 1H, amide, J=7.2), and 11.3 (1H, broad, amide quinolone).

3. 7-amino-4-carboxamido (6-isothiocyanohexyl)methyl-2(1H) quinolone (IX)

Forty-four milligrams (0.22 mmol) of 1,1'-thiocarbonyldiimidazole were added to a solution of 63 mg (0.2 mmol) of product XIII dissolved in 4 ml methanol. After 5 min, this mixture was supplemented with 10 μl of TFA and incubated for 40 min at 50° C. The solvent was removed by evaporation in vacuo, and the product was then washed with water and purified by column chromatography on silica gel using a chloroform:ethanol mixture (4:1) as eluent. Yield~40 mg. $^1$H NMR chemical shifts (d) in DMSO were: 1.2-1.5 (m, 6H), 1.60 (m, 2H, e-$CH_2$, J=7.2), 3.04 (m, 2H, α-$CH_2$, J=7.2), 3.49 (s, 2H, 4-methylene), 3.64 (t, 2H, ζ-$CH_2$, J=7.2), 5.75 (2H, broad, 7 amine), 5.98 (s, 1H, 3H), 6.36 (d, 1H, 8H, J=2.4), 6.43 (dd, 1H, 6H, J$_1$=7.2, J$_2$=2.4), 7.38 (d, 1H, 5H, J=7.2), 8.07 (t, 1H, amide, J=7.2), and 11.20 (1H, broad, amide quinolone).

4. Lanthanide complexes of DTPA-cs124 and DTPA-cs124-NCS (probe 2)

These products were obtained and purified essentially as described for the synthesis of analogous Probe 1 compounds in Section 5 above, except that the incubation time of the corresponding isothiocyano compound (IX) with DTPA dianhydride was 15 min at 20° C. UV: $\lambda_{max}$=341 nm ($\epsilon$=18,900 $M^{-1}$ $cm^{-1}$), $\lambda_{min}$=308 nm ($\epsilon$=10,000 $M^{-1}$ $cm^{-1}$). MS: Tb-DTPA-cs124-NCS (-1) 888.3 (found), 888.0 (calculated); and Eu-DTPA-cs124-NCS (-1) 882.3 (found), 882.0 (calculated)

Synthesis of Luminescent Hybridization Probes

A 10 μl water solution containing 3 to 7 nmol of an oligonucleotide (5' amino-CTTCGTCCACAAACACAACTCCT-GAAG-3' (SEQ ID NO. 1) Blackhole Quencher 2), prepared according to protocols described previously (Tyagi, S., Marras, S. A. E., Vet, J. A. M., and Kramer, F. R. (2000) Molecular beacons: hybridization probes for detection of nucleic acids in homogeneous solutions, in *Nonradioactive Analysis of Biomolecules, second edition* (Kessler, C., Ed.) pp 606-16, Springer Verlag, Berlin, Germany) was supplemented with 5 μl of $Na_2B_4O_7$ (pH 10.0), and 15 μl of a 10 to 20 mM aqueous solution of luminescent probe 1 or probe 2. After incubation for 3.5 h at 56° C., the probe conjugated oligonucleotide was precipitated by the addition of 200 μl of ethanol, and then collected by centrifugation after cooling at -80° C. for 15 min. This procedure was repeated 3 to 4 times. Finally, the residue was dissolved in water and purified by HPLC chromatography, as described in supplemental materials. Yield 40 to 80%.

Physical Methods

Figure 9:
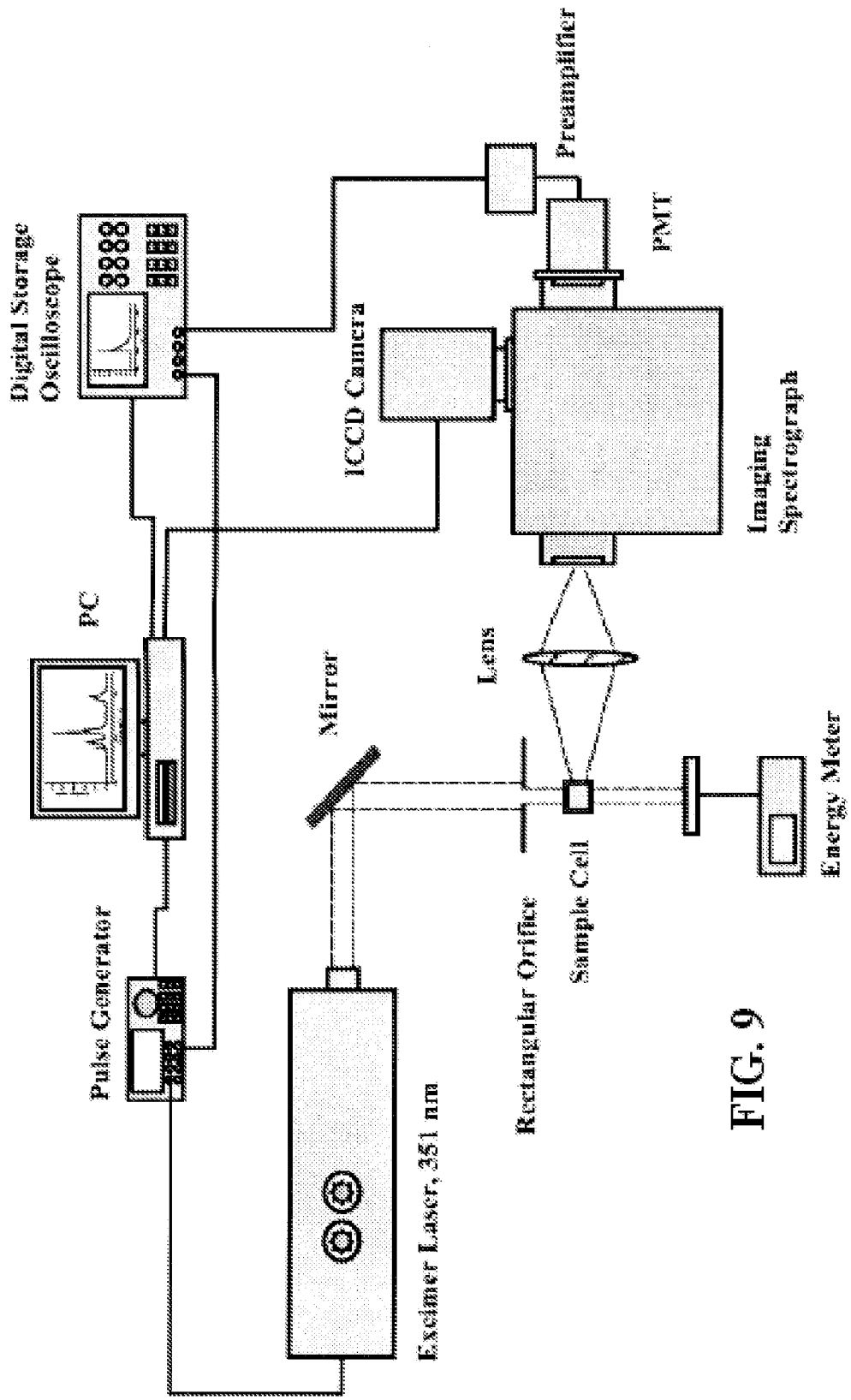
FIG. 9 is a schematic diagram of the experimental set up for time-resolved and gated luminescence measurements.

Excitation and emission fluorescence spectra in a steady state mode were recorded using a QuantaMaster 1 (Photon Technology International) digital fluorometer at ambient temperature. Time-resolved and gated luminescence measurements were performed using a home-built experimental set-up (FIG. 9). A Suprasil fluorescence cell filled with sample solutions was irradiated by pulsed (ca. 15 ns) UV light from an excimer laser (351 nm, XeF). Before passing through the cell, the laser beam was formed by a rectangular aperture 0.5 cm×1.0 cm (width×height). Fluorescence from the cell collected at 90° C. was focused onto the entrance slit of a grating spectrograph (SpectraPro-300i, Acton Research Corp., diffraction grating 150 grooves/mm blazed at 500 nm) using a fused silica lens with a focal distance of 2.5 cm. The spectrograph was equipped with a gated intensified CCD Camera (ICCD-MAX, Princeton Instruments) to record transient spectra. A slit width of 0.5 mm was used for time-resolved luminescence measurements, which corresponds to a spectral resolution of 5 nm. Time-gated spectra were recorded with a spectral resolution of 0.3 nm (a slit width of 0.01 mm in combination with a pixel size on the ICCD camera of 0.026 mm). ICCD gating, with a delay after the laser pulse, was used to determine the temporal behavior of the transient fluorescence. For measurements of luminescence lifetimes, the light was diverted to a photomultiplier tube mounted on the exit slit of the spectrograph. The PMT signal was preamplified and averaged, using a digital storage oscilloscope (LeCroy 9310A). High-resolution spectra were recorded with a time delay of 1 μs and a gate width of 1 ms for probe 1 chelated with Eu and Sm and for probe 2 chelated with Tb and Dy.

Steady-State Fluorescence Measurements

Hybridization experiments of the lanthanide-based molecular beacon with its complementary target DNA (5' TTAGGAGTTGTGTTTGTGGACTT 3' (SEQ ID NO. 2)) were performed in a measuring cell (150 μl) in a hybridization buffer containing 50 mM KCl, 3 mM $MgCl_2$, and 10 mM Tris-HCl (pH 8.0). The concentrations of the molecular beacon and the complementary DNA oligonucleotide (target) were 300 nM and 1,000 nM, respectively. Water-based or deuterium oxide-based solutions were used.

Time-Resolved Luminescence Measurements

Protocol A. 10 μl of various concentrations (0-100 nM) of target DNA (see previous section) was added to 3 ml of a 1 nM solution of molecular beacons in hybridization buffer (see previous section), and was then transferred to a measuring cell. The luminescence of the sample was measured at different time intervals.

Protocol B. Different concentrations (0-3 nM) of target DNA target was added to 3 ml of 10 pM molecular beacons hybridization buffer in a glass tube, and this solution was left for 3 days at room temperature. The solution was then transferred to the measuring cell. The glass tube was washed with 1 ml of the same hybridization buffer containing 30% ethanol and this solution was also transferred to the measuring cell. The resulting luminescent signal was then measured as described above.

Example 2

Absorption Spectra

Figure 10:
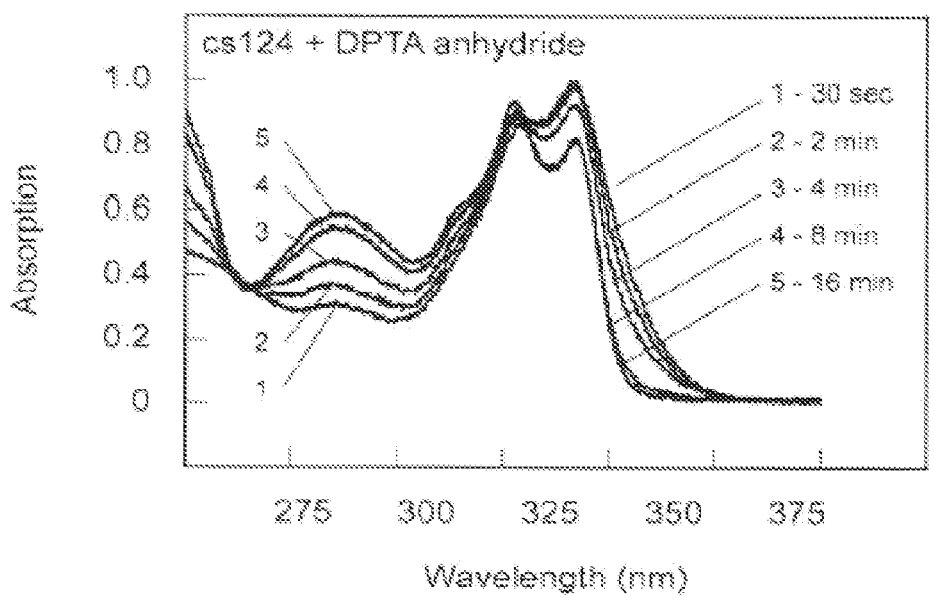
FIG. 10 demonstrates UV spectra of a reaction mixture containing Cs124+DTPA anhydride (A) or cs124-CF$_3$+DTPA anhydride (B) recorded during the course of reaction.
Figure 10:
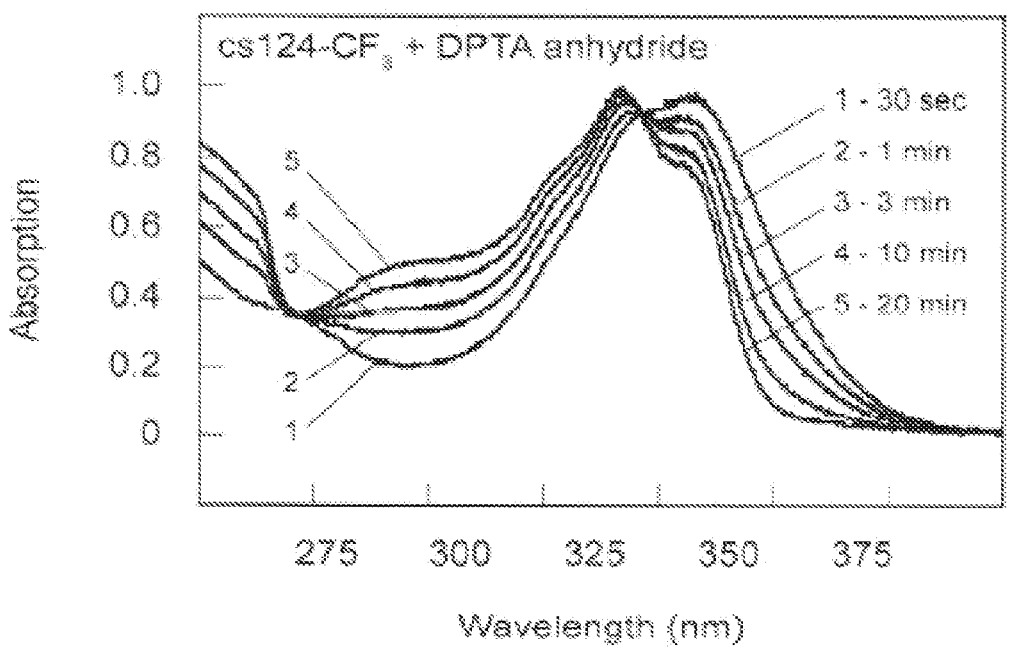

Absorption spectra of the synthesized cs124 and cs124-$CF_3$ derivatives are shown in FIG. 3. They were nearly identical to published spectra for analogous compounds. A small red shift of 6 nm was observed for probe 1 (comparing to the reference compound cs124-$CF_3$) and probe 2 (comparing to the reference compound cs124). The molar extinction coefficients for DTPA-cs124 and DTPA-cs124-$CF_3$ were determined by direct comparison of the absorption spectra of the original compounds ($\epsilon_{max}$=18,900 $M^{-1}$ $cm^{-1}$ at 341 nm for cs124 and $\epsilon_{max}$=14,500 $M^{-1}$ $cm^{-1}$ at 360 nm for cs124-$CF_3$) to their acylated derivatives, which was achieved by monitoring spectral changes in the reaction mixture during the course of the reaction (see FIG. 10). The presence of isosbestic points in both cases was indicative of the conversion of the original compounds to a single reaction product. Indeed, chromatographic analysis confirmed the formation of single acylation products in both cases. Thus, values of $\epsilon_{max}$=18,200 $M^{-1}$ $cm^{-1}$ at 328 nm and $\epsilon_{max}$=14,800 $M^{-1}$ $cm^{-1}$ at 341 nm, were obtained for DTPA-acylated derivatives of cs124 and cs124-$CF_3$, respectively. Essentially the same values were obtained for probes 1 and 2 (data not shown). A significant difference in the absorption spectra of probes 1 and 2 (18 nm) allows selective excitation by common sources (at 351 nm by excimer XeF laser for probe 2, and at 365 nm by mercury UV lamp for probe 2). Such selective excitation is important for applications relying on simultaneous monitoring of two independent processes in the same sample.

Example 3

Emission Spectroscopy of Lanthanide Complexes

Figure 6:
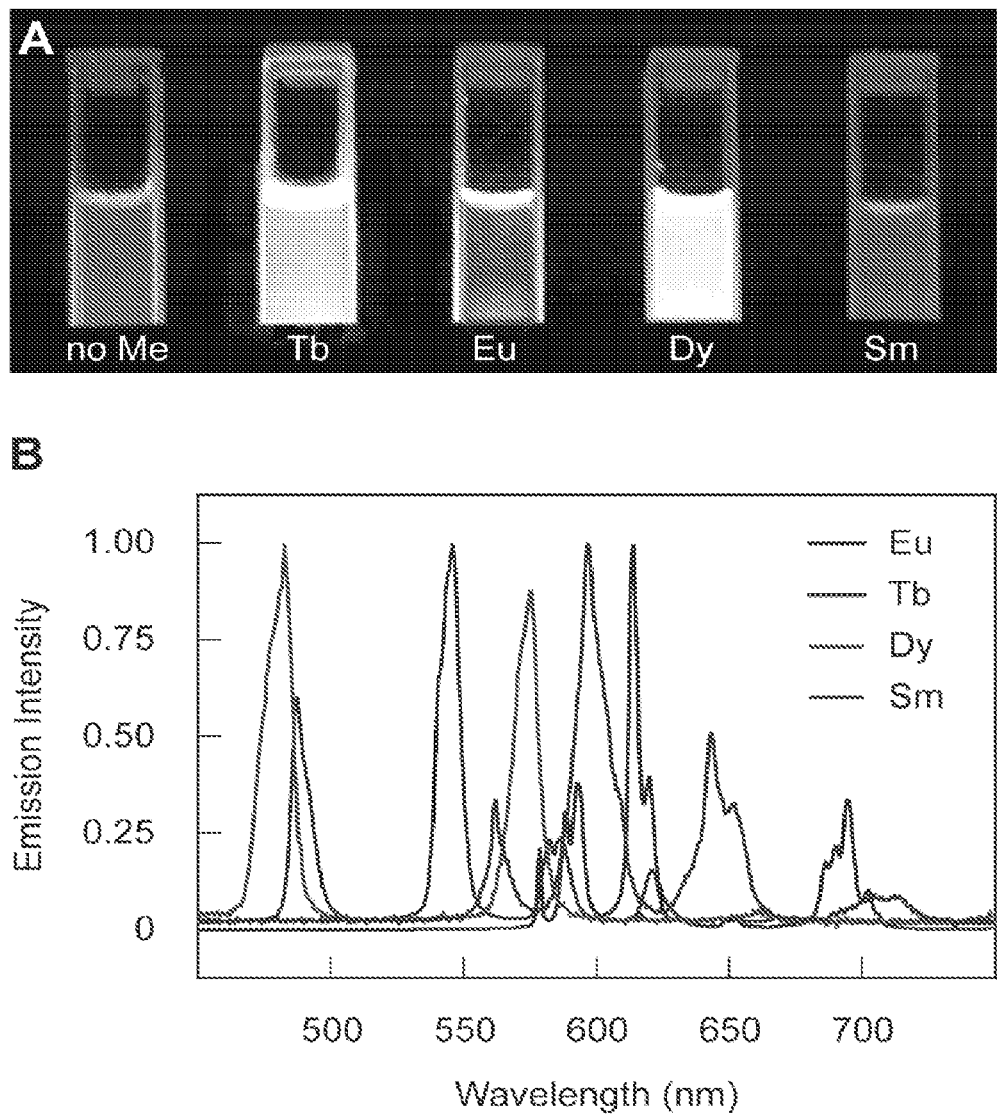
FIG. 6 demonstrates luminescence of probes of the present invention.

The ease of observing the luminescence of these lanthanide complexes is illustrated in FIG. 6A for probe 2. All complexes displayed the narrow emission spectrum typical of luminescent lanthanide chelates (FIG. 6B). Table 3 shows the luminescence intensities of the synthesized reactive lanthanide chelates, as well as for the intensities obtained for the reference compounds, cs124 and cs124-$CF_3$ described earlier. The process of antenna-mediated lanthanide emission includes the transfer of energy from the antenna fluorophore to the coordinated metal, and the subsequent emission of photons by the excited lanthanide. The first step is the most crucial part of the process, because even slight modifications of chromophore-antenna structure dramatically affect lanthanide luminescence. In this work, we explored a synthetic approach that allows the introduction of a cross-linking group in position 3 (probe 1) or position 4 (probe 2) of quinolone-based antenna fluorophores. Comparison with reference fluorophores (with a non-substituted quinolone at position 3, or a methyl-substituted quinolone at position 4) demonstrates that the structural modification affected the brightness of the lanthanide chelates in different ways. For cs124-$CF_3$-based antennae, a significant decrease in brightness was observed for $Tb^{3+}$ chelates (ca. 20-fold) and for $Dy^{3+}$ chelates (>30-fold), while the emission of $Eu^{3+}$ and $Sm^{3+}$ chelates was not significantly affected. A similar effect of substitution was previously observed for the analogous Tb-cs124 chelates. In the case of probe 2, the substitution of a cross-linking group for a methyl group in position 4 did not significantly alter the brightness of all lanthanide complexes. Moreover, a detectable increase in the brightness for Eu (1.5 fold), Dy (1.7 fold), and Sm (1.6 fold) complexes was observed. This is consistent with the results previously obtained for the analogous Tb and Eu derivatives of cs124 containing a carboxymethyl group at position 4. Surprisingly, significant luminescence was detected for $Tb^{3+}$-DTPA-cs124-$CF_3$ chelates, which were previously reported to be non-luminescent. We do not know the reason for this discrepancy. As seen in Table 3, comparing the emission of probe 1 and probe 2, probe 1 gives brighter complexes with Eu and Sm, while probe 2 is optimal for Tb and Dy. Time resolved measurements indicated that there is a single-exponential decay mode for the luminescent signal from probe 1 chelates and from probe 2 chelates (not shown), which is indicative of the homogeneity of the complexes.

TABLE 3

Emission and relative brightness of lanthanide chelates under various conditions.

| Compound | Emission in $H_2O$, counts | Emission in $D_2O$, counts | Relative brightness $D_2O/H_2O$ | Relative brightness in $H_2O$ (%) | Life time in $H_2O$ (ms) | Life time in $D_2O$ (ms) | Number of coordinated $H_2O$ molecules |
|---|---|---|---|---|---|---|---|
| Dysprosium ($Dy^{3+}$) Complexes (emission at 482 nm) | | | | | | | |
| DTPA-cs124-$CF_3$** | 555 | 917 | 1.75 | 20 | 0.0023 | 0.0045 | |
| DTPA-cs124-$CF_3$-NCS (probe 1) | — | — | — | — | — | — | |
| DTPA-cs124** | 2,720 | 10,522 | 3.87 | 100 | 0.011 | 0.033 | — |
| DTPA-cs124-NCS (probe 2) | 4,550 | 13,000 | 2.86 | 167 | 0.009 | 0.027 | — |
| Terbium ($Tb^{3+}$) Complexes (emission at 545 nm) | | | | | | | |
| DTPA-cs124-$CF_3$** | 12,200 | 14,170 | 1.16 | 7.2 | 0.2 | 0.2 | |
| DTPA-cs124-$CF_3$-NCS (probe 1) | 833 | 790 | 0.95 | 0.5 | — | — | — |

TABLE 3-continued

Emission and relative brightness of lanthanide chelates under various conditions.

| Compound | Emission in $H_2O$, counts | Emission in $D_2O$, counts | Relative brightness $D_2O/H_2O$ | Relative brightness in $H_2O$ (%) | Life time in $H_2O$ (ms) | Life time in $D_2O$ (ms) | Number of coordinated $H_2O$ molecules |
|---|---|---|---|---|---|---|---|
| DTPA-cs124** | 169,000 | 260,000 | 1.53 | 100 | 1.5 (1.55*) | 2.3 (2.63*) | 0.97 (1.1*) |
| DTPA-cs124-NCS (probe 2) | 137,000 | 190,000 | 1.40 | 81 | 1.2 | 1.7 | 1.03 |
| Samarium ($Sm^{3+}$) Complexes (emission at 598 nm) | | | | | | | |
| DTPA-cs124-$CF_3$** | 192 | 764 | 3.98 | 168 | 0.0080 | 0.036 | |
| DTPA-cs124-$CF_3$-NCS (probe 1) | 230 | 900 | 3.91 | 200 | 0.0092 | 0.042 | |
| DTPA-cs124** | 114 | 513 | 4.50 | 100 | 0.0082 | 0.023 | — |
| DTPA-cs124-NCS (probe 2) | 180 | 1010 | 6.60 | 158 | 0.0082 | 0.034 | — |
| Europium ($Eu^{3+}$) Complexes (emission at 615 nm) | | | | | | | |
| DTPA-cs124-$CF_3$** | 10,350 | 41,000 | 3.96 | 205 | 0.5 | 1.9 | 1.54 |
| DTPA-cs124-$CF_3$-NCS (probe 1) | 9,450 | 35,000 | 3.70 | 187 | 0.5 | 1.7 | 1.47 |
| DTPA-cs124** | 5,050 | 22,000 | 4.36 | 100 | 0.6 (0.62*) | 1.6 (2.42*) | 1.1 (1.26*) |
| DTPA-cs124-NCS (probe 2) | 7,300 | 25,000 | 3.42 | 145 | 0.6 | 2.0 | 1.19 |

*Determined in Ge, P., and Selvin, P. R. (2004) Carbostyril derivatives as antenna molecules for luminescent lanthanide chelates. *Bioconj. Chem.* 15, 1088-94,
**model compounds Example 4

Effect of Heavy Water on Lanthanide Chelate Emission

The quantum yield of the excited lanthanide ion (defined as the probability of the excited state emitting a photon) in the antenna-chelate complex depends strongly on the number of coordinated water molecules, due to non-radiative dissipation of the energy of the excited state through the vibration of O—H bonds. This process does not occur with heavy water due to the different frequency of O-D bond vibration. This effect accounts for the enhanced brightness of lanthanide luminescence in heavy water. Indeed, as seen from Table 3 for DTPA ligands in $D_2O$, the brightness of the $Tb^{3+}$ chelates was 1.3 to 1.5 fold higher than in $H_2O$-based solutions. As expected, the effect was more pronounced for DTPA-$Eu^{3+}$ chelates (~3- to 3.8-fold), as well as for $Dy^{3+}$ and $Sm^{3+}$ complexes (~4- to 6-fold). The number of coordinated water molecules in $Tb^{3+}$ and $Eu^{3+}$ complexes can be calculated from the luminescence life-time in water and in deuterium oxide-based solutions. For our probes, the number of coordinated water molecules was close to unity (see Table 3), which is in agreement with the results reported for similar compounds. The same is expected for $Dy^{3+}$ and $Sm^{3+}$ chelates, since they have analogous coordination chemistry.

Example 5

Effect of EDTA on the Rate of Lanthanide Chelate Decay

The ability to retain the chelated metal ion is an important characteristic of lanthanide probes. This property is especially crucial for intracellular applications, due to the abundance of metal scavengers in living cells (such as free amino acids, amino acid residues in proteins, nucleoside triphosphates, nucleic acids, etc.). To this end, we investigated the decay rates of the lanthanide chelates used in our probes and in those probes described previously. Reaction of cs124 with excess of DTPA dianhydride yields a primary adduct possessing a preserved acylation function. In previous studies, this function was used to attach the cross-linking group to the chelate constructed by subsequent treatment with diamine, which yielded aminoalkylamide derivatives whose amino group was converted to amine reactive isothiocyanates. This modification of the chelating group is likely to weaken the retention of metal. To this end, as a model, we synthesized analogous, but non-reactive, compounds containing a butylamide group. In accordance with expectations, the lanthanide complexes were about 10 times less stable (comparing to those possessing non-modified chelating groups) when challenged with EDTA.

Example 6

Chemical Reactivity of Synthesized Luminescent Probes

The chemical reactivity of the synthesized probes was evaluated first in reactions with aliphatic diamines and with cysteine, because the resulting reaction products (corresponding thioureas and thiocarbamates) can easily be identified by thin layer chromatography, due to the strong retardation effect. Under the incubation conditions that were used, a nearly quantitative conversion of the probes to the corresponding reaction products was observed, either immediately upon mixing (with 0.1 M cysteine), or after 2 to 3 h at 56° C. (with 10 mM diamine), suggesting that the isothiocyanate groups in the probes survived purification. At the same time, non-reactive control chelates ($Ln^{3+}$-DTPA-cs124, and $Ln^{3+}$-DTPA-cs124-$CF_3$) did not change their mobility after incubation under the same conditions (see supplemental materials).

Example 7

Synthesis of Luminescent-Based Molecular Beacon Probes

With conventional strategies, the nucleic acids are first coupled with metal-free probe derivatives, followed by the addition of a lanthanide to the probe conjugated products, which is not convenient. To this end, we obtained metal-chelated, ready-to-use luminescent tags. This was especially important for probe 1, since a metal-free compound is not stable.

For the attachment of the luminescent tags to the oligonucleotides, we obtained aliphatic isothiocyanate-reactive probes, as opposed to their more reactive aromatic counterparts that are typically used for modification of biopolymers. Partially, this choice was due to a synthetic strategy that required survival of the reactive cross-linking group during acylation by DTPA dianhydride (see Scheme 1), and during subsequent purification. Also, a closely positioned aromatic moiety of isothiocyanate could affect the energy transferred to the lanthanide by the occurrence of stacking interactions with antenna fluorophores. Under optimized reaction conditions, we were able to achieve a 70% coupling efficiency with amine-containing oligonucleotide constructs. The resulting hybridization probes were purified by ethanol precipitation, followed by size-exclusion chromatography and HPLC. Comparison of the absorption spectra of 3' BHQ-2 labeled oligonucleotides, with and without probe 2 attached to their 5' terminal (FIG. 7B), revealed additional absorption in the range of 300 to 350 nm due to the presence of the luminescent label. The survival of the lanthanide chelates during all of these operations is indicative of the extraordinarily high chemical stability of these probes.

Example 8

Steady-State Fluorescence Measurements of Molecular Beacon Probes

Figure 7:
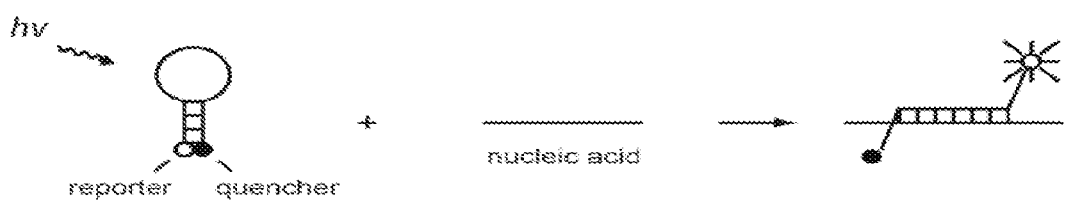
FIG. 7 demonstrates detection of cDNA oligonucleotide targets using luminescence-based molecular beacons labeled by probe 1 Eu chelate.
Figure 7:
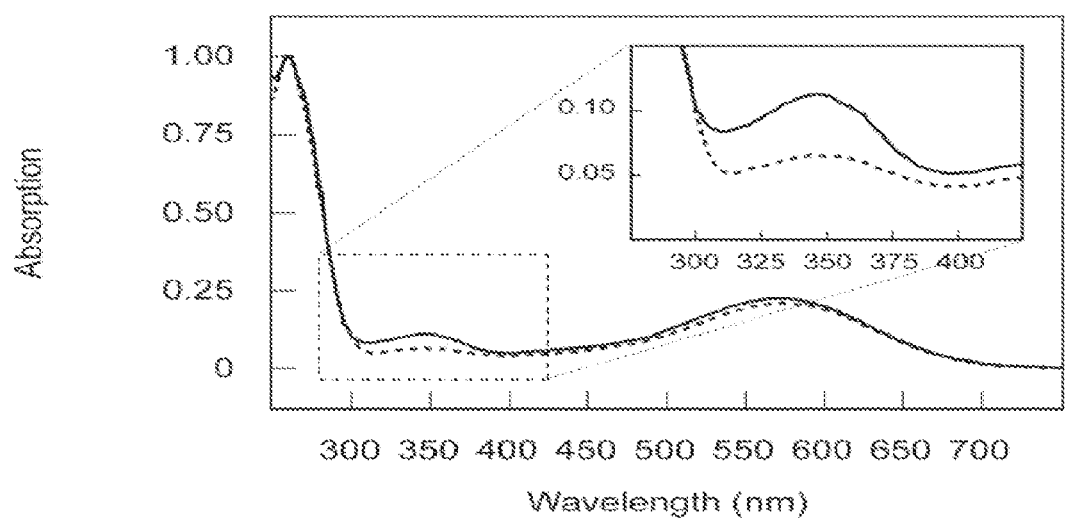
Figure 7:
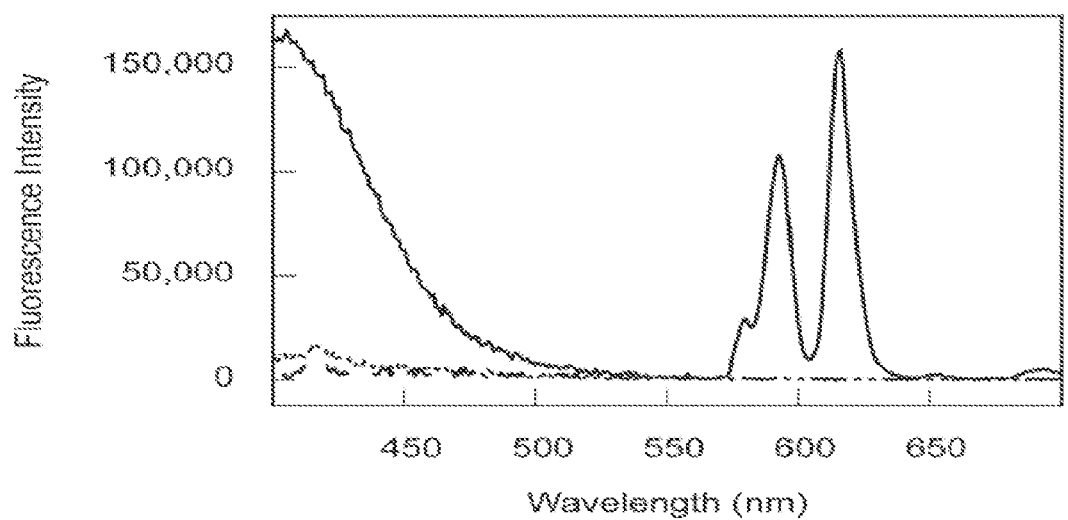
Figure 8:
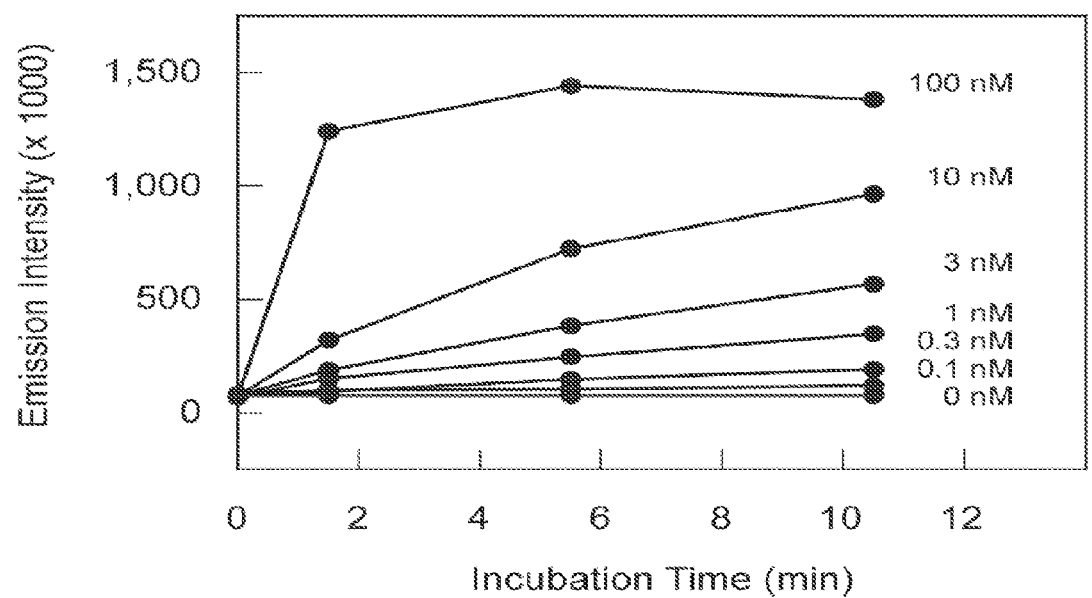
FIG. 8 shows time-resolved detection of a cDNA oligonucleotide.
Figure 8:
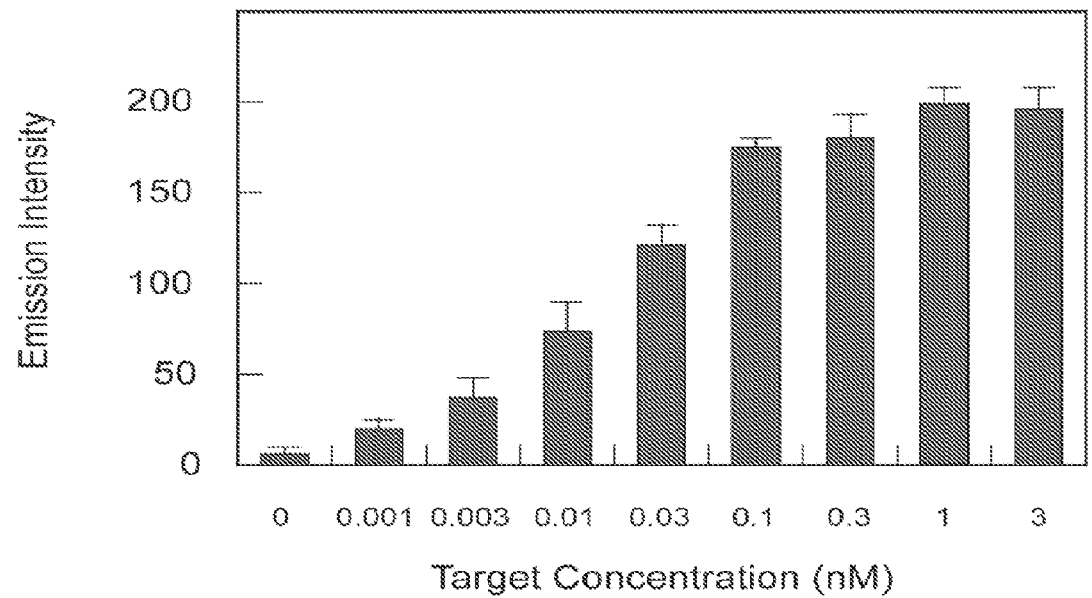

Molecular beacon probes are nucleic acid hybridization probes that fluoresce when they bind to a target DNA or RNA sequence. When they are free in solution and not hybridized to a target nucleic acid they remain non-fluorescent. FIG. 7A illustrates the principle of molecular beacon probes. The probes are single-stranded oligonucleotides that form a stem-and-loop structure. The loop portion of the oligonucleotide is a probe sequence that is complementary to a target sequence in a nucleic acid. The probe sequence is embedded between two "arm" sequences, which are complementary to each other. Under assay conditions, the arms bind to each other to form a double-helical stem hybrid that encloses the probe sequence, forming a hairpin structure. A reporter fluorophore is attached to one end of the oligonucleotide and a non-fluorescent quencher is attached to the other end of the oligonucleotide. The stem hybrid brings the fluorophore and quencher in close proximity, allowing energy from the fluorophore to be transferred directly to quencher through contact quenching. At assay temperatures, when the probe encounters a target nucleic acid, it forms a relatively rigid probe-target hybrid that is longer and more stable than the stem hybrid. Consequently, the molecular beacon probe undergoes a conformational reorganization that forces the stem hybrid to dissociate, and results in the separation of the fluorophore and the quencher, restoring fluorescence.

Currently, most molecular beacon probes are labeled with organic fluorophore labels. To increase the sensitivity of detection, we explored the performance of lanthanide-based molecular beacons by using the novel luminescent probes described in this study, instead of probes possessing conventional fluorophores. An example is shown in FIG. 4C. In this case, we used a europium complex of probe 1 as the luminophore for molecular beacon. As expected, the addition of a complementary DNA target resulted in the development of a signal that is distinguished by the narrow emission peaks that occur in lanthanide luminescence. Remarkably, the ratio of the intensity of the luminescence signal to the intensity of the background fluorescence of the molecular beacon (which is due to the fluorescence of the molecular beacon after subtraction of the background fluorescence of the medium) was >400, which is significantly higher than the signal-to-background ratio typically obtained for fluorophore-based hybridization probes, including molecular beacons. This higher signal-to-background ratio is due to both the suppression of the fluorescence of the antenna and the luminescence of the lanthanide in the "closed" form of the molecular beacon by the quencher. As expected, the signal that occurs upon hybridization of the probe to its target is significantly brighter in heavy water-based solutions.

Example 9

Time-Resolved Luminescence Measurement of Molecular Beacons Probes

FIG. 7A shows the time-course for the development of the luminescence signal that is detected in the time-resolved mode from hybridization mixtures that contain probe 1-based molecular beacons and various concentrations of complementary target DNA. The results demonstrate that when 1 nM hybridization probe is present, sub-nanomolar concentrations of the target can be detected after only 20 min of incubation at ambient temperature. As seen from the time-course results at low concentrations of the target, the hybridization rate decreases significantly, suggesting that the sensitivity of the detection can be improved by increasing the incubation time. Indeed, by lowering the concentration of the hybridization probe to 10 pM (to reduce background emission), and by prolonging the incubation time, we were able to achieve detection limits as low as 1 pM (FIG. 7B), which is about 50- to 100-fold more sensitive than the results that are obtained in the same system using conventional fluorescein-based molecular beacons. Moreover, these detection limits are better than those reported previously for other lanthanide-based hybridization probes.

Example 10

Cell Labeling Using Streptavidin Modified with Multiple Luminescent Probes

1. Cell Labeling Protocol

Figure 11:
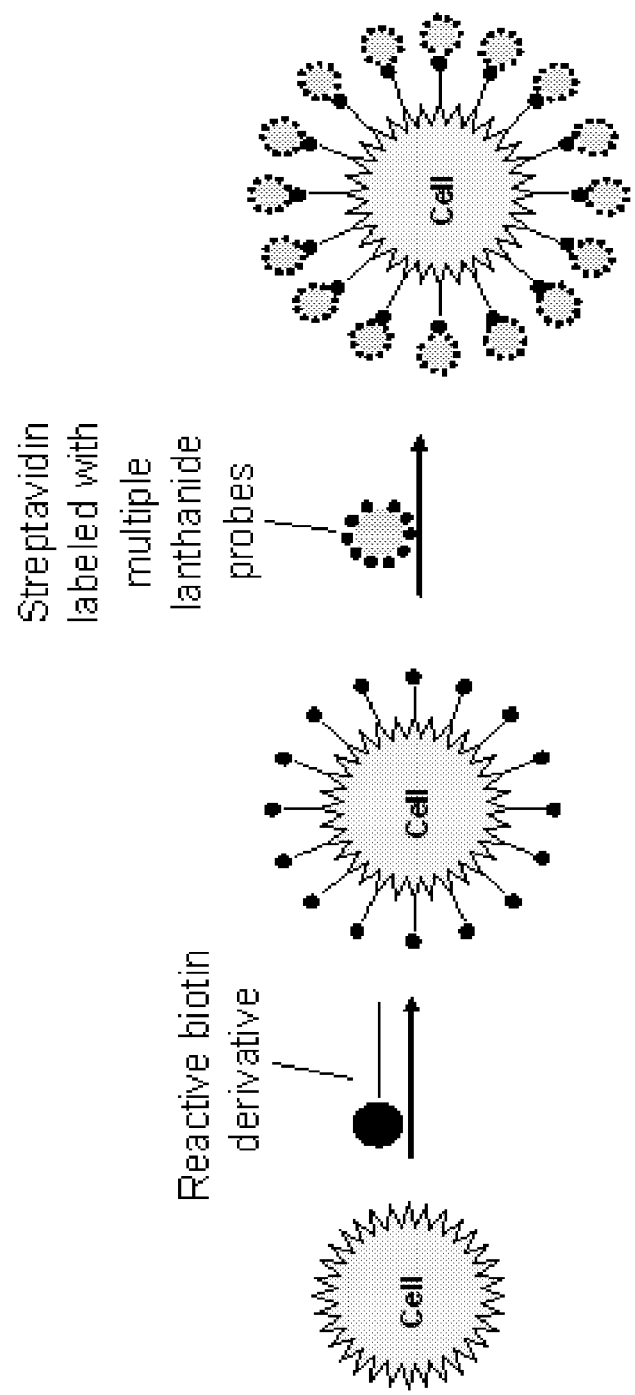
FIG. 11 demonstrates an example of cell labeling using the biotinylation approach, in which reactive biotin derivatives bind to a target cell, and streptavidin labeled with multiple lanthanide probes bind to the bound biotin.

An aliquot (1 ml) of E. coli cells grown to the concentration $10^9$ CFU/ml was centrifuged and the cells washed by water and suspended in 0.1 ml of 0.1 M sodium borate pH 9.0. A succinimide ester of biotin derivative with long carbon spacer (15 carbons) was added to a final concentration of 10 mM. After 30 min incubation at room temperature the cells were washed with water (5×1 ml), re-suspended in water and mixed with streptavidin derivatized with multiple luminescent labels (ca. 20 labels per streptavidin molecule). After 10 min incubation the cells were washed a few times to remove unbound labeled streptavidin and suspended in PBS. This experiment was repeated with preparations of streptavidin, labeled with probes 1, 2, and 5. Samples demonstrating a labeling efficiency of about 6,000 biotin residues per cell can result in a labeling density of 60,000 lanthanides probes per cell (FIG. 11).

2. Time-Resolved Detection of the Labeled Cells

Serial dilutions were made out of the cell suspension and luminescence of each dilution measured in time-resolved mode as described above in Example 1. The best detection limit of about 5 to 6 cells per sample was achieved with probe 5. A detection limit in microscopic mode is capable of achieving 1 cell per sample.

What is claimed is:

1. A composition comprising:
(i) a fluorophore of Formula (I) or Formula (II); and
(ii) a chelating moiety covalently joined, to the fluorophore,
wherein Formula (I) is:

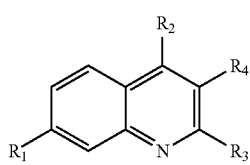

and wherein:
$R_1$ is the site of a covalent attachment, optionally through a linker, of the sensitizer moiety to the chelating moiety;
$R_2$ is a linear alkylene ($C_1$-$C_{20}$) a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene, or alkoxylene moieties are optionally further substituted with from 1-4 halogen atoms;
$R_3$ is a linear alkylene ($C_1$-$C_{20}$) a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N or O; and wherein the linear, branched, or cyclic alkylene, alkenylene, alkynylene, heteroalkylene, arene, alkylarene, or alkoxylene moieties are optionally further substituted with from 1-4 halogen atoms;
$R_4$ is H; a linear alkylene ($C_1$-$C_{20}$) a branched alkylene ($C_3$-$C_{20}$), a cyclic alkylene ($C_3$-$C_{10}$), a linear alkenylene ($C_2$-$C_{20}$), a branched alkenylene ($C_3$-$C_{20}$), a cyclic alkenylene ($C_3$-$C_{10}$), a linear alkynylene ($C_2$-$C_{20}$), a branched alkynylene ($C_3$-$C_{20}$), a cyclic alkynylene ($C_3$-$C_{10}$), an arene ($C_6$-$C_{19}$), an alkylarene having a $C_1$-$C_{20}$ alkyl portion and a $C_6$-$C_{19}$ arene portion, a linear ($C_1$-$C_{20}$) alkoxylene, a branched ($C_3$-$C_{20}$) alkoxylene, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, alkylarene, or alkoxylene moieties are optionally further substituted with from 1-4 halogen atoms;
wherein $R_2$, $R_3$, or $R_4$ optionally further contain a cross-linking group selected from the group consisting of nitrogen mustard, epoxide, maleimide, disulfide, activated ester, imidate, azide, acetylenic derivatives, aldehydes, sulfonyl chlorides, acylazides, and acylhydrazides;
and wherein Formula (II) is:

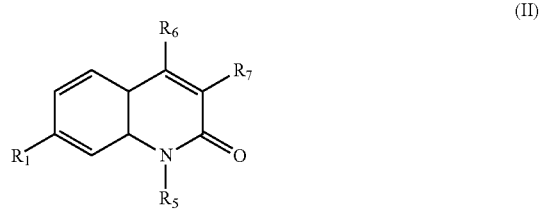

and wherein:

R$_1$ is the site of a covalent attachment, optionally through a linker, of the sensitizer moiety to the chelating moiety;

R$_5$ is H; a linear alkylene (C$_1$-C$_{20}$) a branched alkylene (C$_3$-C$_{20}$), a cyclic alkylene (C$_3$-C$_{10}$), a linear alkenylene (C$_2$-C$_{20}$), a branched alkenylene (C$_3$-C$_{20}$), a cyclic alkenylene (C$_3$-C$_{10}$), a linear alkynylene (C$_2$-C$_{20}$), a branched alkynylene (C$_3$-C$_{20}$), a cyclic alkynylene (C$_3$-C$_{10}$), an arene (C$_6$-C$_{19}$), an alkylarene having a C$_1$-C$_{20}$ alkyl portion and a C$_6$-C$_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;

R$_6$ is a linear alkylene (C$_1$-C$_{20}$) a branched alkylene (C$_3$-C$_{20}$), a cyclic alkylene (C$_3$-C$_{10}$), a linear alkenylene (C$_2$-C$_{20}$), a branched alkenylene (C$_3$-C$_{20}$), a cyclic alkenylene (C$_3$-C$_{10}$), a linear alkynylene (C$_2$-C$_{20}$), a branched alkynylene (C$_3$-C$_{20}$), a cyclic alkynylene (C$_3$-C$_{10}$), an arene (C$_6$-C$_{19}$), an alkylarene having a C$_1$-C$_{20}$ alkyl portion and a C$_6$-C$_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;

R$_7$ is H; a linear alkylene (C$_1$-C$_{20}$) a branched alkylene (C$_3$-C$_{20}$), a cyclic alkylene (C$_3$-C$_{10}$), a linear alkenylene (C$_2$-C$_{20}$), a branched alkenylene (C$_3$-C$_{20}$), a cyclic alkenylene (C$_3$-C$_{10}$), a linear alkynylene (C$_2$-C$_{20}$), a branched alkynylene (C$_3$-C$_{20}$), a cyclic alkynylene (C$_3$-C$_{10}$), an arene (C$_6$-C$_{19}$), an alkylarene having a C$_1$-C$_{20}$ alkyl portion and a C$_6$-C$_{19}$ arene portion, a linear heteroalkylene (2-20 atoms), a branched heteroalkylene (3-20 atoms), or a cyclic heteroalkylene (3-10 atoms), wherein at least one atom of the heteroalkylene is N, O, or S; and wherein the linear, branched, or cyclic alkylene, alkenylene, alkynylene, heteroalkylene, arene, or alkylarene moieties are optionally further substituted with from 1-4 halogen atoms;

wherein R$_5$, R$_6$, or R$_7$ optionally further contain a crosslinking group selected from the group consisting of nitrogen mustard, epoxide, maleimide, disulfide, activated ester, imidate, azide, acetylenic, aldehydes, sulfonyl chlorides, acylazides, and acylhydrazides.

2. The composition of claim 1, wherein R$_2$ is selected from the group consisting of CF$_3$, CH$_3$, and O—CH$_2$CH$_3$.

3. The composition of claim 1, wherein R$_3$ is selected from the group consisting of O—CH$_2$CH$_3$ and O—(CH$_2$)$_3$—N$_3$.

4. The composition of claim 1, wherein R$_4$ is selected from the group consisting of H, CH$_2$C(O)NH—(CH$_2$)$_4$—N=C=S, and CH$_2$C(O)NH—(CH$_2$)$_4$—NHC(O)CH$_2$Br.

5. The composition of claim 1, wherein R$_5$ is selected from the group consisting of alkylene, heteroalkylene and alkylarylene groups, which further contain a crosslinking group selected from the group consisting of maleimide, disulfide, activated ester, azide and acetylene.

6. The compostion of claim 5, wherein R$_5$ is

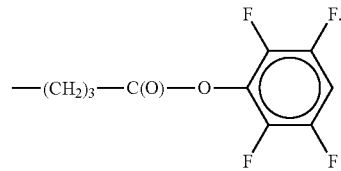

7. The composition of claim 1, wherein R$_6$ is selected from the group consisting of alkylene, heteroalkylene and alkylarylene groups, which further contain a crosslinking group selected from the group consisting of maleimide, disulfide, activated ester, azide and acetylene.

8. The composition of claim 1, wherein R$_7$ is selected from the group consisting of alkylene, heteroalkylene and alkylarylene groups, which further contain a crosslinking group selected from the group consisting of maleimide, disulfide, activated ester, azide and acetylene.

9. The composition of claim 1, wherein the fluorophore has the formula:

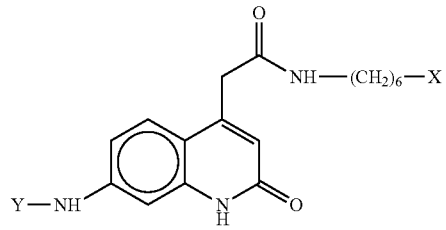

and wherein:

Y is a chelating moiety; and

X is selected from the group consisting of maleimide, disulfide, activated ester, azide, and acetylene groups, optionally linked via a heteroalkylene group.

10. The composition of claim 1, wherein the fluorophore has the formula:

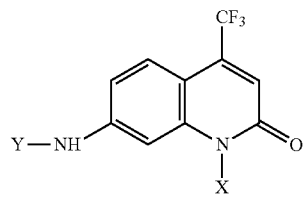

and wherein:

Y is a chelating moiety; and

X is selected from the group consisiting of alkylene, heteroalkylene and alkylarylene groups, which further contain a crosslinking group selected from the group consisting of maleimide, disulfide, activated ester, azide and acetylene.

11. The composition of claim 1, wherein the fluorophore has the formula:

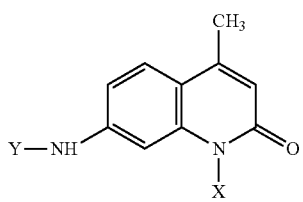

and wherein:
Y is chelating moiety; and
X is selected from the group consisiting of alkylene, heteroalkylene and alkylarylene groups, which further contain a crosslinking group selected from the group consisting of maleimide, disulfide, activated ester, azide and acetylene.

12. The compostion of claim 11, wherein X is

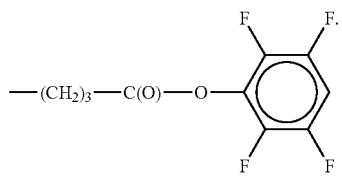

13. The luminescent probe composition of claim 1, wherein the chelating moiety is selected from the group consisting of EDTA, DTPA, TTHA, DOTA, TAGA, DOTP, DTPA-BMA, DO2P, and HP-DO3A.

14. The composition of claim 1 further comprising a metal ion chelated to the chelating moiety, wherein the metal is a lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV).

15. The composition of claim 1, wherein the composition is conjugated to a macromolecule, wherein the macromolecule is selected from the group consisting of a polypeptide and an aptamer with binding affinity to a predetermined peptide target.

16. The composition of claim 15, wherein the macromolecule is a polypeptide selected from the group consisting of an antibody or antigen-binding fragment thereof, a ligand for a cellular receptor, avidin, and streptavidin.

17. The composition of claim 15, wherein the macromolecule is a nucleic acid.

18. A pharmaceutical composition comprising the composition of claim 1 and a pharmaceutically acceptable carrier.

19. A luminescently labeled hairpin-forming oligonucleotide consisting of:

(a) the luminescent composition of claim 1;
wherein the $R_1$ chelating moiety is selected from the group consisting of EDTA, DTPA, TTHA, DOTA, TAGA, DOTP, DTPA-BMA, DO2P, and HP-DO3A; and
wherein the luminescent composition further comprises a lanthanide chelated to the chelating moiety, the lanthanide selected from the group consisting of: Gd(III), Dy(III), Ho(III), Er(III), Eu(III), Tb(III), Sm(III), Ce(III), Pr(III), Yb(III), Tm(III), Nd(III), and Tb(IV);
the luminescent composition covalently conjugated to a hairpin-forming oligonucleotide; and
(b) a quencher moiety capable of quenching the fluorescence of the fluorophore or the luminescence of the lanthanide moiety, wherein the quencher moiety is covalently conjugated to the hairpin-forming oligonucleotide;
the oligonucleotide having a closed conformation including a single-stranded loop and a stem duplex formed by complementary 3' and 5' arms, wherein the quencher moiety is in a quenching relationship to at least one of the lanthanide moiety or the fluorophore; wherein, when excited at the maximum excitation wavelength of the fluorophore, emission at the maximum emission wavelength of the fluorophore is substantially suppressed relative to the unquenched magnitude and emission at the maximum emission wavelength of the fluorophore; and
the oligonucleotide having an open conformation, not including the stem duplex, in which the quencher moiety is not in a quenching relationship with the lanthanide or the fluorophore;
wherein, when excited at the maximum excitation wavelength of one or both of the first and second sensitizer moieties, the luminescence of the lanthanide moiety increases due to fluorescence resonance energy transfer from the fluorophore.

20. The oligonucleotide of claim 19, wherein hybridization of said loop to a target nucleotide sequence causes the oligunucleotide to assume its open configuration.

21. The oligonucleotide of claim 20, wherein the quencher moiety is selected from the group consisting of BHQ, DABCYL, and variants of DABCYL.

22. The oligonucleotide of claim 20, wherein the single-stranded loop and one strand of the stem duplex is complementary to the target strand, whereby the oligonucleotide is capable of serving as a primer for DNA polymerase.

23. The oligonucleotide of claim 19, wherein said oligonucleotide includes a terminal extension capable of serving as a priming region for a DNA polymerase when the olignucleotide is in its closed conformation.

* * * * *

SEQUENCE LISTING

<160> NUMBER OF SEQ ID NOS: 2

<210> SEQ ID NO 1
<211> LENGTH: 27
<212> TYPE: DNA
<213> ORGANISM: artificial
<220> FEATURE:
<223> OTHER INFORMATION: Molecular beacon probe

<400> SEQUENCE: 1
cttcgtccac aaacacaact cctgaag                27

<210> SEQ ID NO 2
<211> LENGTH: 23
<212> TYPE: DNA
<213> ORGANISM: artificial
<220> FEATURE:
<223> OTHER INFORMATION: cDNA target of molecular beacon probe

<400> SEQUENCE: 2
ttaggagttg tgtttgtgga ctt                23